US007241731B2

(12) United States Patent
Hirai et al.

(10) Patent No.: US 7,241,731 B2

(45) Date of Patent: Jul. 10, 2007

(54) OLIGOPEPTIDES FOR PROMOTING HAIR GROWTH

(75) Inventors: Yohei Hirai, Yokohama (JP); Yumiko Oka, Yokohama (JP); Kyoko Takebe, Yokohama (JP); Hokari Tsuda, Yokohama (JP); Keiko Tochigi, Yokohama (JP); Toko Shinagawa, Yokohama (JP); Kayoko Murakami, Yokohama (JP); Shogo Koshida, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 10/155,922

(22) Filed: May 23, 2002

(65) Prior Publication Data

US 2003/0086893 A1 May 8, 2003

Related U.S. Application Data

(63) Continuation-in-part of application No. PCT/JP01/04691, filed on Jun. 4, 2001.

(30) Foreign Application Priority Data

| | | |
|---|---|---|
| Jun. 5, 2000 | (JP) | 2000-166903 |
| Nov. 13, 2001 | (JP) | 2001-347338 |
| Nov. 13, 2001 | (JP) | 2001-347340 |
| Dec. 5, 2001 | (JP) | 2001-371175 |
| Dec. 5, 2001 | (JP) | 2001-371366 |

(51) Int. Cl.
*A61K 31/00* (2006.01)

(52) U.S. Cl. .............................. 514/2; 435/183; 514/52

(58) Field of Classification Search .................... 514/15
See application file for complete search history.

(56) References Cited

U.S. PATENT DOCUMENTS

| | | | | |
|---|---|---|---|---|
| 3,755,560 | A | 8/1973 | Dickert et al. | |
| 4,254,105 | A | 3/1981 | Fukuda | |
| 4,421,769 | A | 12/1983 | Dixon et al. | |
| 4,861,764 | A | 8/1989 | Samour et al. | |
| 4,960,764 | A | 10/1990 | Figueroa, Jr. et al. | |
| 5,082,866 | A | 1/1992 | Wong et al. | |
| 5,196,410 | A | 3/1993 | Francoeur et al. | |
| 5,616,471 | A | 4/1997 | Yuspa | |
| 5,726,298 | A | 3/1998 | Hirai et al. | |
| 5,837,239 | A | 11/1998 | Hirai et al. | |
| 6,299,900 | B1 | 10/2001 | Reed et al. | |
| 6,333,057 | B1 | 12/2001 | Crandall | |
| 6,358,541 | B1 | 3/2002 | Goodman | |
| 6,372,890 | B1 * | 4/2002 | Koshida | 530/350 |
| 6,376,557 | B1 | 4/2002 | Zaveri | |
| 2002/0048558 | A1 | 4/2002 | Niemiec et al. | |
| 2002/0051760 | A1 * | 5/2002 | Hirai et al. | 424/70.14 |

FOREIGN PATENT DOCUMENTS

| | | | | |
|---|---|---|---|---|
| EP | 0 698 666 | A2 | | 2/1996 |
| EP | 0 698 666 | A3 | | 2/1996 |
| EP | 1 008 603 | A1 | | 6/2000 |
| EP | 1156334 | A2 | | 11/2001 |
| EP | 1156334 | A3 | | 11/2001 |
| EP | 1 288 221 | | | 3/2003 |
| EP | 1310511 | A2 | | 5/2003 |
| EP | 1310511 | A3 | | 5/2003 |
| JP | 6-25295 | | | 2/1994 |
| JP | 6-25295 | A | | 2/1994 |
| JP | 9-12432 | | | 1/1997 |
| WO | WO 93/08213 | | * | 4/1993 |
| WO | WO 98/22505 | A1 | | 5/1998 |
| WO | WO 01/94382 | | | 12/2001 |

OTHER PUBLICATIONS

Goyal, A. et al. (1998). "Characterization of Rat Epimorphin/Syntaxin 2 Expression Suggests a Role in Crypt-Villus Morphogenesis," *Am. J. Physiol.* 275: G114-G124.

Hirai, Y. et al. (1992). "Epimorphin: A Mesenchymal Protein Essential for Epithelial Morphogenesis," *Cell.* 69:471-481.

Hirai, Y. et al. (1998). "Epimorphin Functions as a Key Morhporegulator for Mammary Epithelial Cells," *Journal of Cell Biololgy* 140(1):159-169.

Hirai, Y.et al. (1994). "Sodium-Dodecyl-Sulfate-Resistant Complex Formation of Epimorphin Monomers and Interaction of the 150-kDa Complex with the Cell Surface," *European Journal of Biochemistry* 225: 1133-1139.

Koshida, S. and Hirai, Y. (1997). "Identification of Cellular Recognition Sequence of Epimorphin and Critical Role of Cell-Epimorphin Interaction in Lung Branching Morphogenesis," *Biochemical and Biophysical Research Communications* 234(2):522-525.

Lehnert, L. et al. (2001). "Autocrine Stimulation of Human Pancreatic Duct-like Development by Soluble Isoforms of Epimorphin In Vitro," *The Journal of Cell Biology* 152(5):911-922.

Matsuki, Y. et al. (1995). "Gene Expression of Epimorphin in Rat Incisor Ameloblasts," *Archs. Oral. Biol.* 40(2): 161-164.

Mezei, M. (1985). "Liposomes As A Skin Drug Delivery System," *Topics in Pharmaceutical Sciences, Proceedings of the 45th International Congress of Pharmaceutical Sciences of F.I.P.*, held in Montreal, Canada, Breimer, et al. (eds.), Elsevier Science Publishers, pp. 345-358.

(Continued)

*Primary Examiner*—Michael Meller
(74) *Attorney, Agent, or Firm*—Morrison & Foerster, LLP

(57) ABSTRACT

The present invention provides oligopeptides having morphogenesis promoting activity and in particular, hair promoting activity. The oligopeptides may be in monomer form, monomer having a reactive substance bound form or as a polymer, such as a dimer including a homodimer; heterodimer; homotrimer; or heterodimer. The present invention also provides monoclonal antibodies that specifically recognize a 220 kDa antigen of epithelial new hair follicles; hybridomas producing such antibody; and methods and kits for assaying hair growth in mammalian subjects.

42 Claims, 14 Drawing Sheets

OTHER PUBLICATIONS

Mori, M. and Miyazaki, K. 2000). "Factors Affecting Morphogenesis of Rabbit Gallbladder Epithelial Cells Cultured in Collagen Gels," *Cell Tissue Res.* 300: 331-344.

Nakajima, H. et al. (2000). "Expression of Random Peptide Fused to Invasin on Bacterial Cell Surface for Selection of Cell-Targeting Peptides," *Gene* 260:121-131.

Oka, Y. and Hirai, Y. (1996). "Inductive Influences of Epimorphin on Endothelial Cells *In Vitro,*" *Experimental Cell Research* 222: 189-198, Article No. 0024.

Terasaki, Y. et al. (2000). "Increased Expression of Epimorphin in Bleomycin-Induced Pulmonary Fibrosis in Mice," *Am. J. Respir. Cell Mol. Biol.* 23: 168-174.

Watanabe, S. et al. (1998). "A Novel Hepatic Stellate (Ito) Cell-Derived Protein, Epimorphin, Plays a Key Role in the Late Stages of Liver Regeneration," *Biochemical and Biophysical Research Communications* 250: 486-490, Article No. RC989339.

Zhang, L. et al. (1998). "Immunohistochemical Distribution of Epimorphin in Human and Mouse Tissues," *Histochemical Journal* 30: 903-908.

Hirai, Y. (1993) "Molecular Cloning of Human Epimorphin: Identification of Isoforms and Their Unique Properties," *Biochemical and Biophysical Research Communications* 191(3):1332-1337.

Akiyama, M. et al., (1999) "Epimorphin expression during human foetal hair follicle development" *British Journal of Dermatology*, 141:447-452.

Hirai, Y. et al., (May 14, 2001) "Epimorphin mediates mammary luminal morphogenesis through control of C/EBPβ" *The Journal of Cell Biology*, 153(4):785-794.

Supplementary European Search Report mailed on Jan. 26, 2006 for EP Application No. 04700512.9, 3 pages.

Takebe, K. et al. (Nov. 2003). "Epimorphin Acts to Induce Hair Follicle Anagen in C57BL/6 Mice," *The FASEB Journal* 17:2037-2047.

* cited by examiner

Quality of the prepared library

| | S | I | E | Q | S | C | D | Q | D | E |
|---|---|---|---|---|---|---|---|---|---|---|
| F | 2.273% | 5.682% | 0.000% | 0.000% | 5.682% | 5.682% | 0.000% | 0.000% | 0.000% | 0.000% |
| L | 2.273% | 7.955% | 4.545% | 4.545% | 0.000% | 2.273% | 0.000% | 10.227% | 0.000% | 1.136% |
| I | 1.136% | 45% | 0.000% | 0.000% | 0.000% | 0.000% | 0.000% | 0.000% | 0.000% | 0.000% |
| M | 0.000% | 4.545% | 1.136% | 0.000% | 0.000% | 0.000% | 0.000% | 0.000% | 0.000% | 1.136% |
| V | 0.000% | 5.682% | 5.682% | 0.000% | 1.136% | 0.000% | 18.182% | 0.000% | 6.818% | 6.818% |
| S | 58% | 7.955% | 0.000% | 1.136% | 65% | 18.182% | 0.000% | 0.000% | 2.273% | 2.273% |
| P | 9.091% | 3.409% | 0.000% | 12.500% | 6.818% | 1.136% | 1.136% | 10.227% | 2.273% | 1.136% |
| T | 6.818% | 9.091% | 2.273% | 0.000% | 4.545% | 0.000% | 1.136% | 0.000% | 2.273% | 0.000% |
| A | 6.818% | 2.273% | 12.500% | 0.000% | 4.545% | 2.273% | 7.955% | 3.409% | 6.818% | 6.818% |
| Y | 2.273% | 0.000% | 0.000% | 0.000% | 3.409% | 4.545% | 2.273% | 0.000% | 4.545% | 0.000% |
| STOP | 1.136% | 0.000% | 6.818% | 6.818% | 2.273% | 0.000% | 0.000% | 5.682% | 1.136% | 10.227% |
| H | 0.000% | 1.136% | 1.136% | 2.273% | 1.136% | 0.000% | 9.091% | 1.136% | 7.955% | 1.136% |
| Q | 0.000% | 0.000% | 13.636% | 52% | 0.000% | 0.000% | 1.136% | 57% | 2.273% | 9.091% |
| N | 0.000% | 3.409% | 0.000% | 0.000% | 0.000% | 1.136% | 5.682% | 0.000% | 5.682% | 0.000% |
| K | 0.000% | 0.000% | 4.545% | 4.545% | 0.000% | 0.000% | 1.136% | 2.273% | 1.136% | 2.273% |
| D | 1.136% | 1.136% | 1.136% | 0.000% | 0.000% | 2.273% | 36% | 0.000% | 47% | 4.545% |
| E | 0.000% | 1.136% | 38% | 1.136% | 0.000% | 0.000% | 7.955% | 4.545% | 2.273% | 45% |
| C | 7.955% | 0.000% | 0.000% | 0.000% | 2.273% | 39% | 0.000% | 0.000% | 0.000% | 1.136% |
| W | 0.000% | 0.000% | 1.136% | 1.136% | 1.136% | 6.818% | 0.000% | 1.136% | 0.000% | 0.000% |
| R | 0.000% | 1.136% | 0.000% | 12.500% | 2.273% | 11.364% | 1.136% | 4.545% | 1.136% | 1.136% |
| G | 1.136% | 0.000% | 7.955% | 1.136% | 0.000% | 5.682% | 6.818% | 0.000% | 5.682% | 5.682% |
| | 100.000% | 100.000% | 100.000% | 100.000% | 100.000% | 100.000% | 100.000% | 100.000% | 100.000% | 100.000% |

Fig. 2

Quality of the prepared library (theory value)

| | S | I | E | Q | S | C | D | Q | D | E | |
|---|---|---|---|---|---|---|---|---|---|---|---|
| Phe(F) | 6.475 | 6.475 | 0.075 | 0.075 | 6.475 | 6.475 | 0.925 | 0.075 | 0.925 | 0.075 | Phe(F) |
| Leu(L) | 1.525 | 7.525 | 1.925 | 7.925 | 1.525 | 1.025 | 1.075 | 7.925 | 1.075 | 1.925 | Leu(L) |
| Ile(I) | 0.925 | **45.325** | 0.075 | 0.075 | 0.925 | 0.925 | 0.925 | 0.075 | 0.925 | 0.075 | Ile(I) |
| Met(M) | 0.075 | 3.675 | 0.925 | 0.925 | 0.075 | 0.075 | 0.075 | 0.925 | 0.075 | 0.925 | Met(M) |
| Val(V) | 1.000 | 7.000 | 7.000 | 1.000 | 1.000 | 1.000 | 7.000 | 1.000 | 7.000 | 7.000 | Val(V) |
| Ser(S) | **49.925** | 7.475 | 1.075 | 1.075 | **49.925** | 13.975 | 1.925 | 1.075 | 1.925 | 1.075 | Ser(S) |
| Pro(P) | 7.000 | 1.000 | 1.000 | 7.000 | 7.000 | 1.000 | 1.000 | 7.000 | 1.000 | 1.000 | Pro(P) |
| Thr(T) | 7.000 | 7.000 | 1.000 | 1.000 | 7.000 | 1.000 | 1.000 | 1.000 | 1.000 | 1.000 | Thr(T) |
| Ala(A) | 7.000 | 1.000 | 7.000 | 1.000 | 7.000 | 1.000 | 7.000 | 1.000 | 7.000 | 7.000 | Ala(A) |
| Tyr(Y) | 6.475 | 0.925 | 0.525 | 0.525 | 6.475 | 6.475 | 6.475 | 0.525 | 6.475 | 0.525 | Tyr(Y) |
| STOP | 0.525 | 0.075 | 6.475 | 6.475 | 0.525 | 0.525 | 0.525 | 6.475 | 0.525 | 6.475 | STOP |
| His(H) | 0.925 | 0.925 | 0.525 | 3.675 | 0.925 | 0.925 | 6.475 | 3.675 | 6.475 | 0.525 | His(H) |
| Glu(Q) | 0.075 | 0.075 | 6.475 | **45.325** | 0.075 | 0.075 | 0.525 | **45.325** | 0.525 | 6.475 | Glu(Q) |
| Asn(N) | 0.925 | 6.475 | 0.525 | 0.525 | 0.925 | 0.925 | 6.475 | 0.525 | 6.475 | 0.525 | Asn(N) |
| Lys(K) | 0.075 | 0.525 | 6.475 | 6.475 | 0.075 | 0.075 | 0.525 | 6.475 | 0.525 | 6.475 | Lys(K) |
| Asp(D) | 0.925 | 0.925 | 3.675 | 0.525 | 0.925 | 0.925 | **45.325** | 0.525 | **45.325** | 3.675 | Asp(D) |
| Glu(E) | 0.075 | 0.075 | **45.325** | 6.475 | 0.075 | 0.075 | 3.675 | 6.475 | 3.675 | **45.325** | Glu(E) |
| Cys(C) | 6.475 | 0.925 | 0.075 | 0.075 | 6.475 | **45.325** | 0.925 | 0.075 | 0.925 | 0.075 | Cys(C) |
| Trp(W) | 0.525 | 0.075 | 0.925 | 0.925 | 0.525 | 3.675 | 0.075 | 0.925 | 0.075 | 0.925 | Trp(W) |
| Arg(R) | 1.075 | 1.525 | 1.925 | 7.925 | 1.075 | 7.525 | 1.075 | 7.925 | 1.075 | 1.925 | Arg(R) |
| Gly(G) | 1.000 | 1.000 | 7.000 | 1.000 | 1.000 | 7.000 | 7.000 | 1.000 | 7.000 | 7.000 | Gly(G) |
| | 100.000 | 100.000 | 100.000 | 100.000 | 100.000 | 100.000 | 100.000 | 100.000 | 100.000 | 100.000 | |

Fig. 3

Analysis of modified sample using gel permeation column

| | | | | | | | | | | | | | | |
|---|---|---|---|---|---|---|---|---|---|---|---|---|---|---|
| Met | Arg | Asp | Arg | Leu | Pro | Asp | Leu | Thr | Ala | Cys | Arg | Lys | Asn | Asp |
| 1 | | | | 5 | | | | | 10 | | | | | 15 |
| Asp | Gly | Asp | Thr | Val | Val | Val | Val | Glu | Lys | Asp | His | Phe | Met | Asp |
| 16 | | | | 20 | | | | | 25 | | | | | 30 |
| Asp | Phe | Phe | His | Gln | Val | Glu | Glu | Ile | Arg | Asn | Ser | Ile | Asp | Lys |
| 31 | | | | 35 | | | | | 40 | | | | | 45 |
| Ile | Thr | Gln | Tyr | Val | Glu | Glu | Val | Lys | Lys | Asn | His | Ser | Ile | Ile |
| 46 | | | | 50 | | | | | 55 | | | | | 60 |
| Leu | Ser | Ala | Pro | Asn | Pro | Glu | Gly | Lys | Ile | Lys | Glu | Glu | Leu | Glu |
| 61 | | | | 65 | | | | | 70 | | | | | 75 |
| Asp | Leu | Asn | Lys | Glu | Ile | Lys | Lys | Thr | Ala | Asn | Lys | Ile | Arg | Ala |
| 76 | | | | 80 | | | | | 85 | | | | | 80 |
| Lys | Leu | Lys | Ala | Ile | Glu | Gln | Ser | Phe | Asp | Gln | Asp | Glu | | |
| 91 | | | | 95 | | | | | 100 | | | | | |

Fig. 14

| | | | | | | | | | | | | | | |
|---|---|---|---|---|---|---|---|---|---|---|---|---|---|---|
| Met | Arg | Asp | Arg | Leu | Pro | Asp | Leu | Thr | Ala | Cys | Arg | Thr | Asn | Asp |
| 1 | | | | 5 | | | | | 10 | | | | | 15 |
| Asp | Gly | Asp | Thr | Ala | Val | Val | Ile | Val | Glu | Lys | Asp | His | Phe | Met |
| 16 | | | | 20 | | | | | 25 | | | | | 30 |
| Asp | Gly | Phe | Phe | His | Gln | Val | Glu | Glu | Ile | Arg | Ser | Ser | Ile | Ala |
| 31 | | | | 35 | | | | | 40 | | | | | 45 |
| Arg | Ile | Ala | Gln | His | Val | Glu | Asp | Val | Lys | Lys | Asn | His | Ser | Ile |
| 46 | | | | 50 | | | | | 55 | | | | | 60 |
| Ile | Leu | Ser | Ala | Pro | Asn | Pro | Glu | Gly | Lys | Ile | Lys | Glu | Glu | Leu |
| 61 | | | | 65 | | | | | 70 | | | | | 75 |
| Glu | Asp | Leu | Asn | Lys | Glu | Ile | Lys | Lys | Thr | Ala | Asn | Arg | Ile | Arg |
| 76 | | | | 80 | | | | | 85 | | | | | 90 |
| Gly | Lys | Leu | Lys | <u>Ser</u> | <u>Ile</u> | <u>Glu</u> | <u>Gln</u> | <u>Ser</u> | <u>Cys</u> | <u>Asp</u> | Gln | Asp | Glu | |
| 91 | | | | 95 | | | | | 100 | | | | | |

Fig. 15

SEQUENCE LISTING

```
<160> NUMBER OF SEQ ID NOS: 156

<210> SEQ ID NO 1
<211> LENGTH: 103
<212> TYPE: PRT
<213> ORGANISM: Artificial Sequence
<220> FEATURE:
<223> OTHER INFORMATION: Synthetic Construct

<400> SEQUENCE: 1

Met Arg Asp Arg Leu Pro Asp Leu Thr Ala Cys Arg Lys Asn Asp Asp
 1               5                  10                  15
```

-continued

```
Gly Asp Thr Val Val Val Val Glu Lys Asp His Phe Met Asp Asp Phe
            20                  25                  30

Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Ala Glu
            100


<210> SEQ ID NO 2
<211> LENGTH: 104
<212> TYPE: PRT
<213> ORGANISM: Artificial Sequence
<220> FEATURE:
<223> OTHER INFORMATION: Synthetic Construct

<400> SEQUENCE: 2

Met Arg Asp Arg Leu Pro Asp Leu Thr Ala Cys Arg Thr Asn Asp Asp
 1               5                  10                  15

Gly Asp Thr Ala Val Val Ile Val Glu Lys Asp His Phe Met Asp Gly
            20                  25                  30

Phe Phe His Gln Val Glu Glu Ile Arg Ser Ser Ile Ala Arg Ile Ala
        35                  40                  45

Gln His Val Glu Asp Val Lys Lys Asn His Ser Ile Ile Leu Ser Ala
    50                  55                  60

Pro Asn Pro Glu Gly Lys Ile Lys Glu Glu Leu Glu Asp Leu Asn Lys
65                  70                  75                  80

Glu Ile Lys Lys Thr Ala Asn Arg Ile Arg Gly Lys Leu Lys Ser Ile
                85                  90                  95

Glu Gln Ser Cys Asp Gln Asp Glu
            100


<210> SEQ ID NO 3
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Thr or Tyr
<220> FEATURE:
<221> NAME/KEY: VARIANT
<222> LOCATION: 2
<223> OTHER INFORMATION: Xaa = Ser or Asn
<220> FEATURE:
<221> NAME/KEY: VARIANT
<222> LOCATION: 1, 2
<223> OTHER INFORMATION: Xaa = Any Amino Acid

<400> SEQUENCE: 3

Xaa Xaa Glu Gln Ser Cys Ala
 1               5


<210> SEQ ID NO 4
<211> LENGTH: 7
<212> TYPE: PRT
<213> ORGANISM: Artificial Sequence
```

-continued

<220> FEATURE:
<223> OTHER INFORMATION: Synthetic Construct

<400> SEQUENCE: 4

Ser Ile Glu Gln Cys Ser Asp
1 5

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ser Ile Glu Cys Gln Ser Asp
1 5

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Ser Ile Cys Glu Gln Ser Asp
1 5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Tyr Asn Glu Gln Ser Cys Asp
1 5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Thr Ser Asp Gln Cys Cys Asp
1 5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Ser Ile Glu Gln Ser Cys Gly
1 5

<210> SEQ ID NO 10
<211> LENGTH: 7
<212> TYPE: PRT
<213> ORGANISM: Artificial Sequence -continued
<220> FEATURE:
<223> OTHER INFORMATION: Synthetic Construct

<400> SEQUENCE: 10

Ser Ser Ala Gln Ser Cys Leu
1 5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Tyr Ile Glu Gln Tyr Cys Asp
1 5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Thr Ile Trp Gln Ser Cys Asp
1 5

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Thr Thr Glu Gln Ser Cys Ala
1 5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Pro Ser Glu Gln Ser Cys Ala
1 5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Ser Asn Glu Gln Ser Cys Ala
1 5

<210> SEQ ID NO 16
<211> LENGTH: 10
<212> TYPE: PRT
<213> ORGANISM: Artificial Sequence -continued
<220> FEATURE:
<223> OTHER INFORMATION: Synthetic Construct

<400> SEQUENCE: 16

Tyr Ile Lys Gln Ser Cys Glu Gln Asp Glu
1 5 10

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Tyr Asn Glu Gln Ser Cys Asp Arg Glu Glu
1 5 10

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Ser Val Glu Gln Ser Cys His Arg Gly Glu
1 5 10

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Ser Ser Glu Gln Thr Cys Asp Gln His Gly
1 5 10

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Ser Thr Gly Gln Ser Cys Asp Gln Pro Gly
1 5 10

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Thr Thr Glu Gln Ser Cys Asp Gln Gln Glu
1 5 10

<210> SEQ ID NO 22
<211> LENGTH: 10
<212> TYPE: PRT
<213> ORGANISM: Artificial Sequence -continued
<220> FEATURE:
<223> OTHER INFORMATION: Synthetic Construct

<400> SEQUENCE: 22

Ser Ile Arg Gln Phe Cys Asp Gln Asp Val
1 5 10

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Thr Thr Glu Gln Ser Cys Asp Gln Gln Glu
1 5 10

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Ser Asn Glu Pro Cys Ser Asp Gln Gly Gly
1 5 10

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Phe Ile Glu Gln Ser Cys Asp Gln Asn Glu
1 5 10

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 4
<223> OTHER INFORMATION: Xaa = Any Amino Acid

<400> SEQUENCE: 26

Ser Xaa Glu Xaa Ser Cys Asp Gln Asp Gln
1 5 10

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Thr Ser Gln Gln Ser Cys Asp Leu Asp Glu
1 5 10

-continued

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Val Asn Glu Gln Ser Cys Asp Gln Asp Glu
1 5 10

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Ser Asn Glu Gln Ser Cys Ala Val Ala Glu
1 5 10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Ser Ile Glu Gln Ser Cys Asp Gln Asp Trp
1 5 10

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Ser Ile Glu Gln Ser Cys Asp Gln Asp Val
1 5 10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Thr Ile Trp Gln Ser Cys Asp Gln Glu Glu
1 5 10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Thr Ile Glu Gln Ser Cys Asp Glu Val Ala
1 5 10

-continued

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Ser Thr Glu Gln Ser Cys His Lys Val Glu
1 5 10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Ser Ser Glu Gln Trp Cys Ser Gln Asp Gln
1 5 10

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Ser Phe Glu Gln Ser Cys Asp Gln His Glu
1 5 10

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Ser Asn Glu Glu Ser Cys Asp Leu Asp Glu
1 5 10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Ser Ile Lys Gln Ser Cys Asp Pro His Gln
1 5 10

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Gly Leu Glu Gln Ser Cys Asp Gln Asp Trp
1 5 10

-continued

```
<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Thr Gly Glu Gln Ser Cys Asp Gln His Glu
 1               5                   10


<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Ser Ile Glu Gln Ser Cys Ala Pro Ala Phe
 1               5                   10


<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Pro Ile Lys Thr Ser Cys Asp Gln Glu Glu
 1               5                   10


<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Ser Ile Glu Arg Ser Cys Asp Gln Asp Glu
 1               5                   10


<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Ser Ser Glu Arg Ser Cys Asp Pro Asp Glu
 1               5                   10


<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Val Ile Glu Gln Ala Cys Asp Gln Asn Glu
 1               5                   10
```

-continued

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Ala Ile Glu Gln Ser Cys Asp Gln Val Glu
1 5 10

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Ser Ile Glu Gln Ser Cys Asn Gln Asp Glu
1 5 10

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Ser Ser Ala Gln Ser Cys Leu Gln Asp Thr
1 5 10

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Tyr Gly Glu Gln Ser Cys Asp Gln Gly Gln
1 5 10

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Ser Val Glu Gln Ser Cys Asp Pro Asn Asp
1 5 10

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Ser Ile Glu Gln Phe Cys Glu Gln Gly Trp
1 5 10

-continued

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Ser Leu Glu Gln Ser Cys Asp Gln Asp Lys
1 5 10

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Ser Ile Glu Gln Ser Cys Asp Ala His Gln
1 5 10

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Ser Ile Glu Gln Phe Cys Asn Pro Asp Glu
1 5 10

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Pro Ile Gly Pro Ser Cys Asp Lys Pro Val
1 5 10

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Ser Ile Val Gln Ser Cys Gly Glu Ala Glu
1 5 10

<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

Thr Gly Glu Gln Ser Cys Asp Gln His Glu
1 5 10

-continued

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Phe Ile Glu Gln Ser Cys Asp Gln His Val
1 5 10

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Pro Ile Glu Gln Ser Cys Tyr Gln His Gly
1 5 10

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Ser Thr Glu Gln Pro Cys Asp Gln Gly Leu
1 5 10

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Pro Ser Glu Gln Ser Cys Ala Glu Glu Glu
1 5 10

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

Ser Ile Glu Gln Pro Cys His Gln Arg Val
1 5 10

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Thr Thr Glu Gln Ser Cys Ala Val Asp Glu
1 5 10

-continued

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Tyr Ile Glu Gln Tyr Cys Asp Gln Asp Glu
1 5 10

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Thr Ser Asp Gln Cys Cys Asp
1 5

<210> SEQ ID NO 66
<211> LENGTH: 7
<212> TYPE: PRT
<213> ORGANISM: Artificial Sequence
<220> FEATURE:
<223> OTHER INFORMATION: Synthetic Construct

<400> SEQUENCE: 66

Thr Ile Trp Gln Ser Cys Asp
1 5

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct

<400> SEQUENCE: 67

Ser Ile Glu Gln Ser Cys Asp
1 5

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Tyr Gly Glu Gln Ser Cys Asp Gln Gly Gln
1 5 10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Ser Ile Glu Gln Ser Cys Asp Leu His Glu
1 5 10

-continued

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9, 10
<223> OTHER INFORMATION: Xaa = Any Amino Acid

<400> SEQUENCE: 70

Ser Ile Glu Gln Ser Cys Ser Gln Xaa Xaa
1 5 10

<210> SEQ ID NO 71
<211> LENGTH: 10
<212> TYPE: PRT
<213> ORGANISM: Artificial Sequence
<220> FEATURE:
<223> OTHER INFORMATION: Synthetic Construct

<400> SEQUENCE: 71

Ser Ile Glu Gln Ser Cys Asp Gln Asp Glu
1 5 10

<210> SEQ ID NO 72
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Any Amino Acid

<400> SEQUENCE: 72

Ser Asn Glu Pro Ser Cys Xaa Glu Asp Gly
1 5 10

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

Ser Ser Glu His Ser Cys Asp His Asp Glu
1 5 10

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct

<400> SEQUENCE: 74

Pro Ile Lys Thr Ser Cys Asp Gln Phe Glu
1 5 10

<210> SEQ ID NO 75
<211> LENGTH: 10
<212> TYPE: PRT
<213> ORGANISM: Artificial Sequence
<220> FEATURE:
<223> OTHER INFORMATION: Synthetic Construct -continued

<400> SEQUENCE: 75

Tyr Asn Glu Gln Ser Cys Asp Gln Asp Glu
1 5 10

<210> SEQ ID NO 76
<211> LENGTH: 10
<212> TYPE: PRT
<213> ORGANISM: Artificial Sequence
<220> FEATURE:
<223> OTHER INFORMATION: Synthetic Construct

<400> SEQUENCE: 76

Thr Ser Asp Gln Cys Cys Asp Pro Asp Lys
1 5 10

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Ser Ile Glu Ser Ser Cys Asp Thr Ala Glu
1 5 10

<210> SEQ ID NO 78
<211> LENGTH: 10
<212> TYPE: PRT
<213> ORGANISM: Artificial Sequence
<220> FEATURE:
<223> OTHER INFORMATION: Synthetic Construct

<400> SEQUENCE: 78

Ser Phe Gln Gln Ser Cys Glu Gln Asn Glu
1 5 10

<210> SEQ ID NO 79
<211> LENGTH: 10
<212> TYPE: PRT
<213> ORGANISM: Artificial Sequence
<220> FEATURE:
<223> OTHER INFORMATION: Synthetic Construct

<400> SEQUENCE: 79

Ser Ser Glu Gln Phe Cys Asp Gln Gly Lys
1 5 10

<210> SEQ ID NO 80
<211> LENGTH: 10
<212> TYPE: PRT
<213> ORGANISM: Artificial Sequence
<220> FEATURE:
<223> OTHER INFORMATION: Synthetic Construct

<400> SEQUENCE: 80

Ser Ile Glu Gln Ala Cys Gly Gln Gly Glu
1 5 10

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct -continued

<400> SEQUENCE: 81

```
Ser Ile Glu Gln Ser Cys Gly Gln His Glu
 1               5                   10
```

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct

<400> SEQUENCE: 82

```
Ser Val Glu Lys Pro Cys Asp Leu Val Val
 1               5                   10
```

<210> SEQ ID NO 83
<211> LENGTH: 11
<212> TYPE: PRT
<213> ORGANISM: Artificial Sequence
<220> FEATURE:
<223> OTHER INFORMATION: Synthetic Construct

<400> SEQUENCE: 83

```
Lys Ser Ile Glu Gln Ser Cys Asp Gln Asp Glu
 1               5                   10
```

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

```
Ser Ile Glu Gln Ser Cys Asp Gln Asp Glu
 1               5                   10
```

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct

<400> SEQUENCE: 85

```
Ser Ile Glu Gln Ser Cys Asp Gln Asp
 1               5
```

<210> SEQ ID NO 86
<211> LENGTH: 8
<212> TYPE: PRT
<213> ORGANISM: Artificial Sequence
<220> FEATURE:
<223> OTHER INFORMATION: Synthetic Construct

<400> SEQUENCE: 86

```
Ser Ile Glu Gln Ser Cys Asp Gln
 1               5
```

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct -continued

<400> SEQUENCE: 87

Ser Ile Glu Gln Ser Cys Asp
 1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic Construct

<400> SEQUENCE: 88

Ser Ile Glu Gln Ser Cys
 1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Ile Glu Gln Ser Cys Asp Gln Asp Glu
 1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90

Glu Gln Ser Cys Asp Gln Asp Glu
 1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct

<400> SEQUENCE: 91

Gln Ser Cys Asp Gln Asp Glu
 1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic Construct

<400> SEQUENCE: 92

Ser Ile Glu Gln Cys Ser Asp Gln
 1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct -continued

<400> SEQUENCE: 93

Ser Ile Glu Cys Gln Ser Asp Gln
 1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Ser Ile Cys Glu Gln Ser Asp Gln
 1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic Construct

<400> SEQUENCE: 95

Thr Ser Glu Gln Ser Cys Ala
 1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic Construct

<400> SEQUENCE: 96

Thr Asn Glu Gln Ser Cys Ala
 1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic Construct

<400> SEQUENCE: 97

Tyr Ser Glu Gln Ser Cys Ala
 1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic Construct

<400> SEQUENCE: 98

Tyr Asn Glu Gln Ser Cys Ala
 1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic Construct -continued

<400> SEQUENCE: 99

Thr Ser Glu Gln Cys Ser Ala
 1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 100

Thr Asn Glu Gln Cys Ser Ala
 1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 101

Tyr Ser Glu Gln Cys Ser Ala
 1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic Construct

<400> SEQUENCE: 102

Tyr Asn Glu Gln Cys Ser Ala
 1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic Construct

<400> SEQUENCE: 103

Thr Ser Glu Cys Gln Ser Ala
 1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic Construct

<400> SEQUENCE: 104

Thr Asn Glu Cys Gln Ser Ala
 1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic Construct -continued

<400> SEQUENCE: 105

Tyr Ser Glu Cys Gln Ser Ala
 1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic Construct

<400> SEQUENCE: 106

Tyr Asn Glu Cys Gln Ser Ala
 1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic Construct

<400> SEQUENCE: 107

Thr Ser Cys Glu Gln Ser Ala
 1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 108

Thr Asn Cys Glu Gln Ser Ala
 1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic Construct

<400> SEQUENCE: 109

Tyr Ser Cys Glu Gln Ser Ala
 1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic Construct

<400> SEQUENCE: 110

Tyr Asn Cys Glu Gln Ser Ala
 1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic Construct -continued

<400> SEQUENCE: 111

Glu Gln Ser Cys Asp
1 5

<210> SEQ ID NO 112
<211> LENGTH: 5
<212> TYPE: PRT
<213> ORGANISM: Artificial Sequence
<220> FEATURE:
<223> OTHER INFORMATION: Synthetic Construct

<400> SEQUENCE: 112

Glu Gln Cys Ser Asp
1 5

<210> SEQ ID NO 113
<211> LENGTH: 5
<212> TYPE: PRT
<213> ORGANISM: Artificial Sequence
<220> FEATURE:
<223> OTHER INFORMATION: Synthetic Construct

<400> SEQUENCE: 113

Glu Cys Gln Ser Asp
1 5

<210> SEQ ID NO 114
<211> LENGTH: 5
<212> TYPE: PRT
<213> ORGANISM: Artificial Sequence
<220> FEATURE:
<223> OTHER INFORMATION: Synthetic Construct

<400> SEQUENCE: 114

Cys Glu Gln Ser Asp
1 5

<210> SEQ ID NO 115
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid

<400> SEQUENCE: 115

Ser Ile Glu Gln Ser Xaa Asp Gln
1 5

<210> SEQ ID NO 116
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Any Amino Acid

<400> SEQUENCE: 116

Ser Ile Glu Gln Xaa Ser Asp Gln
1 5

-continued

<210> SEQ ID NO 117
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Any Amino Acid

<400> SEQUENCE: 117

Ser Ile Glu Xaa Gln Ser Asp Gln
1 5

<210> SEQ ID NO 118
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Any Amino Acid

<400> SEQUENCE: 118

Ser Ile Xaa Glu Gln Ser Asp Gln
1 5

<210> SEQ ID NO 119
<211> LENGTH: 5
<212> TYPE: PRT
<213> ORGANISM: Artificial Sequence
<220> FEATURE:
<223> OTHER INFORMATION: Synthetic Construct

<400> SEQUENCE: 119

Glu Gln Ser Cys Asp
1 5

<210> SEQ ID NO 120
<211> LENGTH: 4
<212> TYPE: PRT
<213> ORGANISM: Artificial Sequence
<220> FEATURE:
<223> OTHER INFORMATION: Synthetic Construct

<400> SEQUENCE: 120

Glu Gln Ser Cys
1

<210> SEQ ID NO 121
<211> LENGTH: 7
<212> TYPE: PRT
<213> ORGANISM: Artificial Sequence
<220> FEATURE:
<223> OTHER INFORMATION: Synthetic Construct

<400> SEQUENCE: 121

Ser Ile Asp Gln Ser Cys Asp
1 5

<210> SEQ ID NO 122
<211> LENGTH: 7
<212> TYPE: PRT
<213> ORGANISM: Artificial Sequence
<220> FEATURE:
<223> OTHER INFORMATION: Synthetic Construct -continued

<400> SEQUENCE: 122

Ser Ile Glu Glu Ser Cys Asp
 1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic Construct

<400> SEQUENCE: 123

Ser Ile Glu Gln Ala Cys Asp
 1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic Construct

<400> SEQUENCE: 124

Ser Ile Glu Gln Ser Cys Arg
 1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic Construct

<400> SEQUENCE: 125

Ser Ile Glu Gln Phe Cys His
 1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic Construct

<400> SEQUENCE: 126

Ser Phe Asp Gln Ser Cys Asp
 1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic Construct

<400> SEQUENCE: 127

Ser Phe Glu Glu Ser Cys Asp
 1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic Construct -continued

<400> SEQUENCE: 128

Ser Phe Glu Gln Ala Cys Asp
1 5

<210> SEQ ID NO 129
<211> LENGTH: 7
<212> TYPE: PRT
<213> ORGANISM: Artificial Sequence
<220> FEATURE:
<223> OTHER INFORMATION: Synthetic Construct

<400> SEQUENCE: 129

Ser Phe Glu Gln Ser Cys Arg
1 5

<210> SEQ ID NO 130
<211> LENGTH: 7
<212> TYPE: PRT
<213> ORGANISM: Artificial Sequence
<220> FEATURE:
<223> OTHER INFORMATION: Synthetic Construct

<400> SEQUENCE: 130

Ser Phe Glu Gln Phe Cys His
1 5

<210> SEQ ID NO 131
<211> LENGTH: 10
<212> TYPE: PRT
<213> ORGANISM: Artificial Sequence
<220> FEATURE:
<223> OTHER INFORMATION: Synthetic Construct

<400> SEQUENCE: 131

Ser Ile Glu Gln Cys Ser Asp Gln Asp Glu
1 5 10

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct

<400> SEQUENCE: 132

Ser Ile Glu Cys Gln Ser Asp Gln Asp Glu
1 5 10

<210> SEQ ID NO 133
<211> LENGTH: 10
<212> TYPE: PRT
<213> ORGANISM: Artificial Sequence
<220> FEATURE:
<223> OTHER INFORMATION: Synthetic Construct

<400> SEQUENCE: 133

Ser Ile Cys Glu Gln Ser Asp Gln Asp Glu
1 5 10

<210> SEQ ID NO 134
<211> LENGTH: 10
<212> TYPE: PRT
<213> ORGANISM: Artificial Sequence
<220> FEATURE:
<223> OTHER INFORMATION: Synthetic Construct -continued

<400> SEQUENCE: 134

Ser Ile Glu Gln Ser Lys Asp Gln Asp Glu
1 5 10

<210> SEQ ID NO 135
<211> LENGTH: 5
<212> TYPE: PRT
<213> ORGANISM: Artificial Sequence
<220> FEATURE:
<223> OTHER INFORMATION: Synthetic Construct

<400> SEQUENCE: 135

Ser Ile Glu Gln Ser
1 5

<210> SEQ ID NO 136
<211> LENGTH: 48
<212> TYPE: DNA
<213> ORGANISM: Artificial Sequence
<220> FEATURE:
<223> OTHER INFORMATION: Synthetic Construct

<400> SEQUENCE: 136
tccggtccgc catcacgttg gctcgagcca ggatattggg gtccgtga 48

<210> SEQ ID NO 137
<211> LENGTH: 68
<212> TYPE: DNA
<213> ORGANISM: Artificial Sequence
<220> FEATURE:
<223> OTHER INFORMATION: Synthetic Construct

<400> SEQUENCE: 137
ctgcagaacc atcacgttgg agtattgagc agagttgtga tcaggatgag ccaggatatt 60
ggatgcat 68

<210> SEQ ID NO 138
<211> LENGTH: 68
<212> TYPE: DNA
<213> ORGANISM: Artificial Sequence
<220> FEATURE:
<223> OTHER INFORMATION: Synthetic Construct

<400> SEQUENCE: 138
ctgcagaacc atcacgttgg agtattgagc agagttgtga tcaggatgag ccaggatatt 60
ggatgcat 68

<210> SEQ ID NO 139
<211> LENGTH: 18
<212> TYPE: DNA
<213> ORGANISM: Artificial Sequence
<220> FEATURE:
<223> OTHER INFORMATION: Synthetic Construct

<400> SEQUENCE: 139
atgcatccaa tatcctgg 18

<210> SEQ ID NO 140
<211> LENGTH: 60
<212> TYPE: DNA
<213> ORGANISM: Artificial Sequence
<220> FEATURE:
<223> OTHER INFORMATION: Synthetic Construct -continued

<400> SEQUENCE: 140
gggcccgggt cactgatcgc tctggtcaca aatagacttc agcttgcccc ggatcctgtt 60

<210> SEQ ID NO 141
<211> LENGTH: 60
<212> TYPE: DNA
<213> ORGANISM: Artificial Sequence
<220> FEATURE:
<223> OTHER INFORMATION: Synthetic Construct

<400> SEQUENCE: 141
gggcccgggt cactgatcgc tacactggtc aatagacttc agcttgcccc ggatcctgtt 60

<210> SEQ ID NO 142
<211> LENGTH: 66
<212> TYPE: DNA
<213> ORGANISM: Artificial Sequence
<220> FEATURE:
<223> OTHER INFORMATION: Synthetic Construct

<400> SEQUENCE: 142
gggcccgggt cactcgtcct gatcgctctg gtcaatacaa gacttcagct tgccccggat 60
cctgtt 66

<210> SEQ ID NO 143
<211> LENGTH: 66
<212> TYPE: DNA
<213> ORGANISM: Artificial Sequence
<220> FEATURE:
<223> OTHER INFORMATION: Synthetic Construct

<400> SEQUENCE: 143
gggcccgggt cactcgtcct gatcgctctg acagtcaata gacttcagct tgccccggat 60
cctgtt 66

<210> SEQ ID NO 144
<211> LENGTH: 66
<212> TYPE: DNA
<213> ORGANISM: Artificial Sequence
<220> FEATURE:
<223> OTHER INFORMATION: Synthetic Construct

<400> SEQUENCE: 144
gggcccgggt cactcgtcac actgatcgct ctggtcaata gacttcagct tgccccggat 60
cctgtt 66

<210> SEQ ID NO 145
<211> LENGTH: 66
<212> TYPE: DNA
<213> ORGANISM: Artificial Sequence
<220> FEATURE:
<223> OTHER INFORMATION: Synthetic Construct

<400> SEQUENCE: 145
gggcccgggt cactcacagt cctgatcgct ctggtcaata gacttcagct tgccccggat 60
cctgtt 66

<210> SEQ ID NO 146
<211> LENGTH: 36
<212> TYPE: DNA
<213> ORGANISM: Artificial Sequence
<220> FEATURE:
<223> OTHER INFORMATION: Synthetic Construct -continued

<400> SEQUENCE: 146
agcttccatc acgttggtct agaccaggat attgga 36

<210> SEQ ID NO 147
<211> LENGTH: 36
<212> TYPE: DNA
<213> ORGANISM: Artificial Sequence
<220> FEATURE:
<223> OTHER INFORMATION: Synthetic Construct

<400> SEQUENCE: 147
aggtagtgca accagatctg gtcctataac cttcga 36

<210> SEQ ID NO 148
<211> LENGTH: 7
<212> TYPE: PRT
<213> ORGANISM: Artificial Sequence
<220> FEATURE:
<223> OTHER INFORMATION: Synthetic Construct

<400> SEQUENCE: 148

Ala Ile Glu Gln Ser Phe Asp
1 5

<210> SEQ ID NO 149
<211> LENGTH: 10
<212> TYPE: PRT
<213> ORGANISM: Artificial Sequence
<220> FEATURE:
<223> OTHER INFORMATION: Synthetic Construct

<400> SEQUENCE: 149

Ser Cys Ile Glu Gln Ser Asp Gln Asp Glu
1 5 10

<210> SEQ ID NO 150
<211> LENGTH: 10
<212> TYPE: PRT
<213> ORGANISM: Artificial Sequence
<220> FEATURE:
<223> OTHER INFORMATION: Synthetic Construct

<400> SEQUENCE: 150

Ser Ile Glu Gln Ser Asp Gln Cys Asp Glu
1 5 10

<210> SEQ ID NO 151
<211> LENGTH: 10
<212> TYPE: PRT
<213> ORGANISM: Artificial Sequence
<220> FEATURE:
<223> OTHER INFORMATION: Synthetic Construct

<400> SEQUENCE: 151

Ser Ile Glu Gln Ser Asp Gln Asp Cys Glu
1 5 10

<210> SEQ ID NO 152
<211> LENGTH: 4
<212> TYPE: PRT
<213> ORGANISM: Artificial Sequence
<220> FEATURE:
<223> OTHER INFORMATION: Synthetic Construct -continued

<400> SEQUENCE: 152

Glu Gln Cys Ser
 1

<210> SEQ ID NO 153
<211> LENGTH: 4
<212> TYPE: PRT
<213> ORGANISM: Artificial Sequence
<220> FEATURE:
<223> OTHER INFORMATION: Synthetic Construct

<400> SEQUENCE: 153

Glu Cys Gln Ser
 1

<210> SEQ ID NO 154
<211> LENGTH: 4
<212> TYPE: PRT
<213> ORGANISM: Artificial Sequence
<220> FEATURE:
<223> OTHER INFORMATION: Synthetic Construct

<400> SEQUENCE: 154

Cys Glu Gln Ser
 1

<210> SEQ ID NO 155
<211> LENGTH: 8
<212> TYPE: PRT
<213> ORGANISM: Artificial Sequence
<220> FEATURE:
<223> OTHER INFORMATION: Synthetic Construct

<400> SEQUENCE: 155

Ser Ile Cys Glu Gln Ser Cys Asp
 1               5

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid

<400> SEQUENCE: 156

Ser Ile Glu Gln Ser Xaa Asp Gln Asp Glu
 1               5                   10

OLIGOPEPTIDES FOR PROMOTING HAIR GROWTH

CROSS-REFERENCE TO RELATED APPLICATIONS

The present application is a continuation-in-part application of PCT/JP01/04691 filed Jun. 4, 2001 which claims the benefit of priority to Japanese application 2000-166903 filed Jun. 5, 2000 and claims the benefit of priority to Japanese application 2001-347340, filed Nov. 13, 2001, Japanese application 2001-347338, filed Nov. 13, 2001, Japanese application 2001-371175 filed Dec. 5, 2001, and Japanese application 2001-371366 filed Dec. 5, 2001, all of which are hereby incorporated herein by reference in their entirety.

TECHNICAL FIELD

The present invention relates to oligopeptides having morphogenesis activity. In particular, the present invention provides compositions comprising oligopeptides having hair growth promoting activity and methods for promoting hair growth in humans. The present invention also relates to monoclonal antibodies specific for an antigen of epithelial new hair follicle and methods for the evaluation of hair growth promoting activity using such a monoclonal antibody.

BACKGROUND

The normal morphogenesis of epithelial tissue has been suggested to be controlled by factors derived from mesenchymal cells present around the epithelial tissue. Diseases resulting from the abnormal morphogenesis of epithelial tissue are largely caused by abnormalities of mesenchymal cells. Therefore, an interest has arisen in understanding the mechanism by which mesenchymal cells control the morphogenesis of epithelial tissue.

Epimorphin, disclosed in Japanese Patent Laid-Open Publication No. 25295/94, has 277 to 289 amino acids as a core protein, and has the action of promoting the morphogenesis of epithelial tissue through its action on epithelial cells. It was found that normal tissue formation did not progress when epimorphin failed to function.

Epimorphin has been described in Hirai et al. (1992, *Cell,* 69:471-481); Hirai (1994, *Eur. J. Biochem*, vol. 225, 1133-1139); Hirai, et al. (1998, *J. Cell. Biol.,* 140:159-169); and Hirai, et al. (2001, *J. Cell. Biol.,* 153:785-794).

EP 0698666 A2 describes the structure of full length epimorphin as roughly divided into four fragments, beginning from the N-terminus, a coiled coil domain (1), a functional domain (2), a coiled coil domain (3), and hydrophobic domain at the C-terminal. EP0698666A discloses that the functional domain (the domain specified by 104th to 187th amino acids in human epimorphin) participates in cell adhesion and is associated with expression of physiological activity of epimorphin.

U.S. Pat. No. 5,726,298, issued Mar. 10, 1998, discloses human and murine epimorphin nucleotide and amino acid sequences. WO98/22505 and EP 1008603A1 describe polypeptides specified by the N-terminal sequence of the 1st to 103rd amino acids of human epimorphin and by the N-terminal sequence of the 1st to 104th amino acids of murine epimorphin.

Native mammalian epimorphin is almost insoluble in an aqueous media such as saline, which causes difficulty in using epimorphin in compositions for human treatment. Japanese Patent Laid-Open Publication No. 25295/1994 discloses a modified form of epimorphin obtained by removing a hydrophobic region at the C-terminus.

In spite of developments in the understanding of epimorphin and morphogenesis of epithelial tissue, there remains a need for means to modify the morphogenesis of epithelial tissue, in particular as it relates to diseases or disorders associated with abnormal morphogenesis.

DISCLOSURE OF THE INVENTION

The present invention relates to oligopeptides useful for the treatment or amelioration of symptoms of diseases or disorders associated with abnormal morphogenesis. The oligopeptides of the present invention can be used to induce morphogenesis, induce revascularization effect, induce regeneration effect, induce cardiovascular regeneration, and induce endothelial cell growth. The oligopeptides of the present invention can be used, for example, for the treatment of and/or amelioration of symptoms of burns or wounds or to promote hair growth or prevent hair loss. In particular, the present invention relates to oligopeptides having hair growth promoting activity and to methods of promoting hair growth. The present invention also relates to methods of assaying for hair growth using a monoclonal antibody specific for a 220 kDa antigen of epithelial new follicles and kits comprising a monoclonal antibody of the present invention.

The present invention provides isolated oligopeptides of between about 5 and about 104 amino acid residues in length having hair growth promoting activity, comprising the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Ala, Tyr, Thr, Pro, Phe, Val, Gly, Leu, Ile or Met, or is deleted from said oligopeptide;

X2 is an amino acid residue of Ile, Gly, Asn, Thr, Val, Ser, Phe, Leu, Ala, Pro, Cys, or Met, or is deleted from said oligopeptide;

X3 is an amino acid residue of Glu, Lys, Gln, Arg, Ala, Val, Trp, Cys, or Asp;

X4 is an amino acid residue of Gln, Pro, Glu, Thr, Arg, Ser, His, Cys, or Lys;

X5 is an amino acid residue of Ser, Trp, Phe, Thr, Cys, Tyr, Pro, Ala, Gly, Val, Leu, Ile, or Met;

X6 is an amino acid residue Cys; a reactive substance-bound Cys or a reactive substance-bound Lys; and X7 is an amino acid residue of Asp, Glu, His, Ser, Ala, Gly, Asn, Tyr, Arg, or Leu, or is deleted from said oligopeptide, with the proviso that the oligopeptide is not identical to SEQ ID NO:1 or SEQ ID NO:2.

The present invention also provides isolated oligopeptides of between about 5 and about 104 amino acid residues in length having hair growth promoting activity, comprising the following amino acid sequence,

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Tyr, Thr, or Pro, or is deleted from said oligopeptide;

X2 is an amino acid residue of Ile, Asn, Thr, or Ser, or is deleted from said oligopeptide;

X3 is an amino acid residue of Glu, Ala, Trp, or Asp;

X4 is an amino acid residue of Gln;

X5 is an amino acid residue of Ser, Cys, or Tyr;

X6 is an amino acid residue of Cys; a reactive substance-bound Cys or a reactive substance-bound Lys; and X7 is an amino acid residue of Asp, Ala, Gly, or Leu, or is deleted from said oligopeptide, with the proviso that the oligopeptide is not SEQ ID NO:2.

The present invention also provides isolated oligopeptides of between about 7 and about 100 amino acid residues in length having hair growth promoting activity, comprising the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Ala, Tyr, Thr, Pro, Phe, Val, Gly, Leu, Ile or Met, or is deleted from said oligopeptide;

X2 is an amino acid residue of Ile, Gly, Asn, Thr, Val, Ser, Phe, Leu, Ala, Pro, Cys, or Met, or is deleted from said oligopeptide;

X3 is an amino acid residue of Glu, Lys, Gln, Arg, Ala, Val, Trp, Cys, or Asp;

X4 is an amino acid residue of Gln, Pro, Glu, Thr, Arg, Ser, His, Cys, or Lys;

X5 is an amino acid residue of Ser, Trp, Phe, Thr, Cys, Tyr, Pro, Ala, Gly, Val, Leu, Ile, or Met;

X6 is an amino acid residue Cys; a reactive substance-bound Cys or a reactive substance-bound Lys; and X7 is an amino acid residue of Asp, Glu, His, Ser, Ala, Gly, Asn, Tyr, Arg, or Leu, or is deleted from said oligopeptide.

The present invention also provides isolated oligopeptides of between about 7 and about 100 amino acid residues in length having hair growth promoting activity comprising the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Tyr, Thr, or Pro, or is deleted from said oligopeptide;

X2 is an amino acid residue of Ile, Asn, Thr, or Ser, or is deleted from said oligopeptide;

X3 is an amino acid residue of Glu, Ala, Trp, or Asp;

X4 is an amino acid residue of Gln;

X5 is an amino acid residue of Ser, Cys, or Tyr;

X6 is an amino acid residue of Cys; and

X7 is an amino acid residue of Asp, Ala, Gly, or Leu, or is deleted from said oligopeptide.

In some examples, an oligopeptide having hair growth promoting activity comprises T/Y-S/N-E-Q-S-C-A. (SEQ ID NO:3).

In some examples, the present invention provides oligopeptides having hair growth promoting activity which comprise at least an amino acid sequence wherein 1 to 3 amino acid residues are substituted in the amino acid sequence for murine pep7 region, Ser-Ile-Glu-Gln-Ser-Cys-Asp (SEQ ID NO: 67), wherein the amino acid residue to be substituted is other than Cys or the amino acid residue to be substituted is other than the third to sixth amino acid residues Glu-Gln-Ser-Cys (SEQ ID NO: 120). In other examples, the present invention provides oligopeptides wherein 0 to 2 amino acid residues are substituted in the amino acid sequence represented by Glu-Gln-Ser-Cys-Asp (SEQ ID NO: 119); wherein the amino acid residue to be substituted is other than Cys or the amino acid residue to be substituted is other than the third to sixth amino acid residues Glu-Gln-Ser-Cys (SEQ ID NO: 120). In some examples, the present invention provides oligopeptides wherein the first Ser is substituted with a hydrophobic amino acid residue or a neutral amino acid residue in the amino acid sequence of Ser-Ile-Glu-Gln-Ser-Cys-Asp (SEQ ID NO: 67).

In other examples, the present invention provides oligopeptides wherein the first Ser is substituted with Ala, Tyr, Thr, Pro, Phe, Val or Gly in the amino acid sequence of Ser-Ile-Glu-Gln-Ser-Cys-Asp (SEQ ID NO: 67). In some examples, the present invention provides oligopeptides wherein the second Ile is substituted with a neutral amino acid residue or a hydrophobic amino acid residue in the amino acid sequence of Ser-Ile-Glu-Gln-Ser-Cys-Asp (SEQ ID NO: 119). In further examples, the present invention provides oligopeptides wherein the second Ile is substituted with Gly, Asn, Thr, Val, Ser, Phe or Leu in the amino acid sequence of Ser-Ile-Glu-Gln-Ser-Cys-Asp (SEQ ID NO: 67). In some examples, the present invention provides oligopeptides wherein the fifth Ser is substituted with a neutral amino acid residue or a hydrophobic amino acid residue in the amino acid sequence of Ser-Ile-Glu-Gln-Ser-Cys-Asp (SEQ ID NO: 67). In other examples, the present invention provides oligopeptides wherein the fifth Ser is substituted with Trp, Phe, Thr, Cys, Tyr, Pro or Ala in the amino acid sequence of Ser-Ile-Glu-Gln-Ser-Cys-Asp (SEQ ID NO: 67). In further examples, the present invention provides oligopeptides wherein the seventh Asp is substituted with a hydrophilic amino acid residue, Gly, Ala or Leu in the amino acid sequence of Ser-Ile-Glu-Gln-Ser-Cys-Asp (SEQ ID NO: 67). The present invention also provides oligopeptides wherein the seventh Asp is substituted with Glu, His, Ser, Ala, Gly, Asn, Tyr or Leu in the amino acid sequence of Ser-Ile-Glu-Gln-Ser-Cys-Asp (SEQ ID NO: 67). In some examples, the present invention provides oligopeptides wherein the third Glu is substituted with Lys, Gly, Gln, Arg, Ala, Val Asp or Trp in the amino acid sequence of Ser-Ile-Glu-Gln-Ser-Cys-Asp (SEQ ID NO: 67). In other examples, the present invention provides oligopeptides wherein the fourth Gln is substituted with Pro, Glu, Thr, Arg, Ser, His or Lys in the amino acid sequence of Ser-Ile-Glu-Gln-Ser-Cys-Asp (SEQ ID NO: 67). In some examples, the present invention provides oligopeptides wherein the first Ser is substituted with Thr or Tyr, the second Ile is substituted with Ser, Asn or Thr, the third Glu is substituted with Ala, Asp or Trp, the fifth Ser is substituted with Cys or Tyr, and/or the seventh Asp is substituted with Gly, Ala or Leu in the amino acid sequence of Ser-Ile-Glu-Gln-Ser-Cys-Asp (SEQ ID NO: 67). In further examples, the present invention provides oligopeptides wherein 1 to 3 amino acid residues other than the third to sixth amino acid residues Glu-Gln-Ser-Cys (SEQ ID NO: 120) are substituted in the amino acid sequence of Ser-Ile-Glu-Gln-Ser-Cys-Asp (SEQ ID NO: 67), the first Ser is substituted with Thr or Tyr, the second Ile is substituted with Ser, Asn or Thr, and/or the seventh Asp is substituted with Gly, Ala or Leu.

In some examples, the present invention provides oligopeptides having hair growth promoting activity which comprise at least an amino acid sequence wherein 1 to 3 amino acid residues are substituted in the amino acid sequence Ser-Ile-Glu-Gln-Cys-Ser-Asp (SEQ ID NO: 67) (a mutation of the murine pep7 region wherein Cys is in the 5th amino acid position of the region) wherein the amino acid residue to be substituted is other than Cys or other than the third to sixth amino acid residues Glu-Gln-Cys-Ser (SEQ ID NO: 120). In further examples, the present invention provides oligopeptides wherein 0 to 2 amino acid residues are substituted in the amino acid sequence represented by Glu-Gln-Cys-Ser-Asp (SEQ ID NO: 112); wherein the amino acid residue to be substituted is other than Cys or other than the third to sixth amino acid residues Glu-Gln-Cys-Ser (SEQ ID NO: 152). In some examples, the present invention provides oligopeptides wherein the first Ser is substituted with a hydrophobic amino acid residue or a neutral amino acid residue in the amino acid sequence of Ser-Ile-Glu-Gln-Cys-Ser-Asp (SEQ ID NO: 4). In other examples, the present invention provides oligopeptides wherein the first Ser is substituted with Ala, Tyr, Thr, Pro, Phe, Val or Gly in the amino acid sequence of Ser-Ile-Glu-Gln-Cys-Ser-Asp (SEQ ID NO: 4). In some examples, the present invention provides oligopeptides wherein the second Ile is substituted with a neutral amino acid residue or a hydrophobic amino acid residue in the amino acid sequence of Ser-Ile-Glu-Gln-Cys-Ser-Asp (SEQ ID NO: 4). In further examples, the present invention provides oligopeptides wherein the second Ile is substituted with Gly, Asn, Thr, Val, Ser, Phe or Leu in the amino acid sequence of Ser-Ile-Glu-Gln-Cys-Ser-Asp (SEQ ID NO: 4). In additional examples, the present invention provides oligopeptides wherein the sixth Ser is substituted with a neutral amino acid residue or a hydrophobic amino acid residue in the amino acid sequence of Ser-Ile-Glu-Gln-Cys-Ser-Asp (SEQ ID NO: 4). In some examples, the present invention provides oligopeptides wherein the sixth Ser is substituted with Trp, Phe, Thr, Cys, Tyr, Pro or Ala in the amino acid sequence of Ser-Ile-Glu-Gln-Cys-Ser-Asp (SEQ ID NO: 4). The present invention also provides oligopeptides wherein the seventh Asp is substituted with a hydrophilic amino acid residue, Gly, Ala or Leu in the amino acid sequence of Ser-Ile-Glu-Gln-Cys-Ser-Asp (SEQ ID NO: 4). In some examples, the present invention provides oligopeptides wherein the seventh Asp is substituted with Glu, His, Ser, Ala, Gly, Asn, Tyr or Leu in the amino acid sequence of Ser-Ile-Glu-Gln-Cys-Ser-Asp (SEQ ID NO: 4). In other examples, the present invention provides oligopeptides wherein the third Glu is substituted with Lys, Gly, Gln, Arg, Ala, Val, Asp or Trp in the amino acid sequence of Ser-Ile-Glu-Gln-Cys-Ser-Asp (SEQ ID NO: 4). In some examples, the present invention provides oligopeptides wherein the fourth Gln is substituted with Pro, Glu, Thr, Arg, Ser, His or Lys in the amino acid sequence of Ser-Ile-Glu-Gln-Cys-Ser-Asp (SEQ ID NO: 4). In other examples, the present invention provides oligopeptides wherein the first Ser is substituted with Thr or Tyr, the second Ile is substituted with Ser, Asn or Thr, the third Glu is substituted with Ala, Asp or Trp, the sixth Ser is substituted with Cys or Tyr, and/or the seventh Asp is substituted with Gly, Ala or Leu in the amino acid sequence of Ser-Ile-Glu-Gln-Cys-Ser-Asp (SEQ ID NO: 4). In some examples, the present invention provides oligopeptides wherein 1 to 3 amino acid residues other than the third to sixth amino acid residues Glu-Gln-Cys-Ser (SEQ ID NO: 152) are substituted in the amino acid sequence of Ser-Ile-Glu-Gln-Cys-Ser-Asp (SEQ ID NO: 4), the first Ser is substituted with Thr or Tyr, the second Ile is substituted with Ser, Asn or Thr, and/or the seventh Asp is substituted with Gly, Ala or Leu.

In other examples, the present invention provides oligopeptides which comprises at least an amino acid sequence wherein 1 to 3 amino acid residues are substituted in the amino acid sequence Ser-Ile-Glu-Cys-Gln-Ser-Asp (SEQ ID NO: 5) (a mutation of the murine pep7 region wherein Cys is in the 4th amino acid position of the region) wherein the amino acid residue to be substituted is other than Cys or wherein the amino acid residue to be substituted is other than the third to sixth amino acid residues Glu-Cys-Gln-Ser (SEQ ID NO: 153). In further examples, the present invention provides an oligopeptide wherein 0 to 2 amino acid residues are substituted in the amino acid sequence represented by Glu-Cys-Gln-Ser-Asp (SEQ ID NO: 113); wherein the amino acid residue to be substituted is other than Cys or wherein the amino acid residue to be substituted is other than the third to sixth amino acid residues Glu-Cys-Gln-Ser (SEQ ID NO: 153). In further examples, the present invention provides oligopeptides wherein the first Ser is substituted with a hydrophobic amino acid residue or a neutral amino acid residue in the amino acid sequence of Ser-Ile-Glu-Cys-Gln-Ser-Asp (SEQ ID NO: 5). In some examples, the present invention provides oligopeptides wherein the first Ser is substituted with Ala, Tyr, Thr, Pro, Phe, Val or Gly in the amino acid sequence of Ser-Ile-Glu-Cys-Gln-Ser-Asp (SEQ ID NO: 5). The present invention further provides oligopeptides wherein the second Ile is substituted with a neutral amino acid residue or a hydrophobic amino acid residue in the amino acid sequence of Ser-Ile-Glu-Cys-Gln-Ser-Asp (SEQ ID NO: 5). In some examples, the present invention provides oligopeptides wherein the second Ile is substituted with Gly, Asn, Thr, Val, Ser, Phe or Leu in the amino acid sequence of Ser-Ile-Glu-Cys-Gln-Ser-Asp (SEQ ID NO: 5). In other examples, the present invention provides oligopeptides wherein the sixth Ser is substituted with a neutral amino acid residue or a hydrophobic amino acid residue in the amino acid sequence of Ser-Ile-Glu-Cys-Gln-Ser-Asp (SEQ ID NO: 5). In some examples, the present invention provides oligopeptides wherein the sixth Ser is substituted with Trp, Phe, Thr, Cys, Tyr, Pro or Ala in the amino acid sequence of Ser-Ile-Glu-Cys-Gln-Ser-Asp (SEQ ID NO: 5). In yet further examples, the present invention provides oligopeptides wherein the seventh Asp is substituted with a hydrophilic amino acid residue, Gly, Ala or Leu in the amino acid sequence of Ser-Ile-Glu-Cys-Gln-Ser-Asp (SEQ ID NO: 5).

In additional examples, the present invention provides oligopeptides wherein the seventh Asp is substituted with Glu, His, Ser, Ala, Gly, Asn, Tyr or Leu in the amino acid sequence of Ser-Ile-Glu-Cys-Gln-Ser-Asp (SEQ ID NO: 5). In some examples, the present invention provides oligopeptides wherein the third Glu is substituted with Lys, Gly, Gln, Arg, Ala, Val, Asp or Trp in the amino acid sequence of Ser-Ile-Glu-Cys-Gln-Ser-Asp (SEQ ID NO: 5). In other examples, the present invention provides oligopeptides wherein the fifth Gln is substituted with Pro, Glu, Thr, Arg, Ser, His or Lys in the amino acid sequence of Ser-Ile-Glu- Cys-Gln-Ser-Asp (SEQ ID NO: 5). In yet other examples, the present invention provides oligopeptides wherein the first Ser is substituted with Thr or Tyr, the second Ile is substituted with Ser, Asn or Thr, the third Glu is substituted with Ala, Asp or Trp, the sixth Ser is substituted with Cys or Tyr, and/or the seventh Asp is substituted with Gly, Ala or Leu in the amino acid sequence of Ser-Ile-Glu-Cys-Gln-Ser-Asp (SEQ ID NO: 5). In other examples, the present invention provides oligopeptides wherein 1 to 3 amino acid residues other than the third to sixth amino acid residues Glu-Cys-Gln-Ser (SEQ ID NO: 153) are substituted in the amino acid sequence of Ser-Ile-Glu-Cys-Gln-Ser-Asp (SEQ ID NO: 5), the first Ser is substituted with Thr or Tyr, the second Ile is substituted with Ser, Asn or Thr, and/or the seventh Asp is substituted with Gly, Ala or Leu.

In some examples, the present invention provides oligopeptides wherein 1 to 3 amino acid residues are substituted in the amino acid sequence represented by Ser-Ile-Cys-Glu-Gln-Ser-Asp (SEQ ID NO: 6) (a mutation of the murine pep7 region wherein Cys is in the 3rd amino acid position of the region) wherein the amino acid residue to be substituted is other than Cys or other than the third to sixth amino acid residues Cys-Glu-Gln-Ser (SEQ ID NO: 154). In further examples, the present invention provides oligopeptides wherein 0 to 2 amino acid residues are substituted in the amino acid sequence represented by Cys-Glu-Gln-Ser-Asp (SEQ ID NO: 114), wherein the amino acid residue to be substituted is other than Cys or other than the third to sixth amino acid residues Cys-Glu-Gln-Ser (SEQ ID NO: 154). In some examples, the present invention provides oligopeptides wherein the first Ser is substituted with a hydrophobic amino acid residue or a neutral amino acid residue in the amino acid sequence of Ser-Ile-Cys-Glu-Gln-Ser-Asp (SEQ ID NO: 6). In some examples, the present invention provides oligopeptides wherein the first Ser is substituted with Ala, Tyr, Thr, Pro, Phe, Val or Gly in the amino acid sequence of Ser-Ile-Cys-Glu-Gln-Ser-Asp (SEQ ID NO: 6). In other examples, the present invention provides oligopeptides wherein the second Ile is substituted with a neutral amino acid residue or a hydrophobic amino acid residue in the amino acid sequence of Ser-Ile-Cys-Glu-Gln-Ser-Asp (SEQ ID NO: 6). In additional examples, the present invention provides oligopeptides wherein the second Ile is substituted with Gly, Asn, Thr, Val, Ser, Phe or Leu in the amino acid sequence of Ser-Ile-Cys-Glu-Gln-Ser-Asp (SEQ ID NO: 6). In other examples, the present invention provides oligopeptides wherein the sixth Ser is substituted with a neutral amino acid residue or a hydrophobic amino acid residue in the amino acid sequence of Ser-Ile-Cys-Glu-Gln-Ser-Asp (SEQ ID NO: 6). In some examples, the present invention provides oligopeptides wherein the sixth Ser is substituted with Trp, Phe, Thr, Cys, Tyr, Pro or Ala in the amino acid sequence of Ser-Ile-Cys-Glu-Gln-Ser-Asp (SEQ ID NO: 6). In further examples, the present invention provides oligopeptides wherein the seventh Asp is substituted with a hydrophilic amino acid residue, Gly, Ala or Leu in the amino acid sequence of Ser-Ile-Cys-Glu-Gln-Ser-Asp (SEQ ID NO: 6). In other examples, the present invention provides oligopeptides wherein the seventh Asp is substituted with Glu, His, Ser, Ala, Gly, Asn, Tyr or Leu in the amino acid sequence of Ser-Ile-Cys-Glu-Gln-Ser-Asp (SEQ ID NO: 6). In additional examples, the present invention provides oligopeptides wherein the fourth Glu is substituted with Lys, Gly, Gln, Arg, Ala, Val, Asp or Trp in the amino acid sequence of Ser-Ile-Cys-Glu-Gln-Ser-Asp (SEQ ID NO: 6). In some examples, the present invention provides oligopeptides wherein the fifth Gln is substituted with Pro, Glu, Thr, Arg, Ser, His or Lys in the amino acid sequence of Ser-Ile-Cys-Glu-Gln-Ser-Asp (SEQ ID NO: 6). In further examples, the present invention provides oligopeptides wherein the first Ser is substituted with Thr or Tyr, the second Ile is substituted with Ser, Asn or Thr, the fourth Glu is substituted with Ala, Asp or Trp, the sixth Ser is substituted with Cys or Tyr, and/or the seventh Asp is substituted with Gly, Ala or Leu in the amino acid sequence of Ser-Ile-Cys-Glu-Gln-Ser-Cys-Asp (SEQ ID NO: 155). The present invention also provides oligopeptides wherein 1 to 3 amino acid residues other than the third to sixth amino acid residues Cys-Glu-Gln-Ser (SEQ ID NO: 154) are substituted in the amino acid sequence of Ser-Ile-Cys-Glu-Gln-Ser-Asp (SEQ ID NO: 6), the first Ser is substituted with Thr or Tyr, the second Ile is substituted with Ser, Asn or Thr, and/or the seventh Asp is substituted with Gly, Ala or Leu.

In some examples, the present invention provides oligopeptides wherein 1 to 3 amino acid residues are substituted in the amino acid sequence represented by Glu-Gln-Ser-Cys-Asp (SEQ ID NO: 111). In other examples, the present invention provides oligopeptides wherein 1 to 3 amino acid residues are substituted in the amino acid sequence represented by Glu-Gln-Cys-Ser-Asp (SEQ ID NO: 112). In some examples, the present invention provides oligopeptides wherein 1 to 3 amino acid residues are substituted in the amino acid sequence represented by Glu-Cys-Gln-Ser-Asp (SEQ ID NO: 113). In other examples, the present invention provides oligopeptides wherein 1 to 3 amino acid residues are substituted in the amino acid sequence represented by Cys-Glu-Gln-Ser-Asp (SEQ ID NO: 114).

In additional examples, the present invention provides oligopeptides comprising an amino acid sequence selected from the group consisting of the following:

Lys-Ser-Ile-Glu-Gln-Ser-Cys-Asp-Gln-Asp-Glu (SEQ ID NO: 83);

Ser-Ile-Glu-Gln-Ser-Cys-Asp-Gln-Asp-Glu (SEQ ID NO: 84);

Ser-Ile-Glu-Gln-Ser-Cys-Asp-Gln-Asp (SEQ ID NO: 85);

Ser-Ile-Glu-Gln-Ser-Cys-Asp-Gln (SEQ ID NO: 86);

Ser-Ile-Glu-Gln-Ser-Cys-Asp (SEQ ID NO: 87);

Ser-Ile-Glu-Gln-Ser-Cys (SEQ ID NO: 88);

Ile-Glu-Gln-Ser-Cys-Asp-Gln-Asp-Glu (SEQ ID NO: 89);

Glu-Gln-Ser-Cys-Asp-Gln-Asp-Glu (SEQ ID NO: 90); and

Gln-Ser-Cys-Asp-Gln-Asp-Glu (SEQ ID NO: 91).

The present invention also provides oligopeptides comprising between about 8 and about 20 amino acid residues and comprising an amino acid sequence selected from the group consisting of:

Ser-Ile-Glu-Gln-Ser-Xaa-Asp-Gln (SEQ ID NO: 115);

Ser-Ile-Glu-Gln-Xaa-Ser-Asp-Gln (SEQ ID NO: 116);

Ser-Ile-Glu-Xaa-Gln-Ser-Asp-Gln (SEQ ID NO: 117); and

Ser-Ile-Xaa-Glu-Gln-Ser-Asp-Gln (SEQ ID NO: 118), wherein Xaa is Cys, or a reactive substance-bound Cys.

The present invention also provides oligopeptides comprising an amino acid sequence selected from the group consisting of:

Ser-Ile-Glu-Gln-Cys-Ser-Asp-Gln (SEQ ID NO: 92);

Ser-Ile-Glu-Cys-Gln-Ser-Asp-Gln (SEQ ID NO: 93); and

Ser-Ile-Cys-Glu-Gln-Ser-Asp-Gln (SEQ ID NO: 94).

The present invention also provides oligopeptides comprising an amino acid sequence of any one of SEQ ID NO:3 through SEQ ID NO:135. The present invention also provides oligopeptides comprising the following amino acid sequences: Tyr Asn Glu Gln Ser Cys Asp Arg Glu Glu (SEQ ID NO: 17); Thr Ser Asp Gln Cys Cys Asp Pro Asp Lys (SEQ ID NO: 76); Pro Ser Glu Gln Ser Cys Ala Glu Glu Glu (SEQ ID NO: 61); Ser Asn Glu Gln Ser Cys Ala Val Ala Glu (SEQ ID NO: 29); Thr Thr Glu Gln Ser Cys Ala Val Asp Glu (SEQ ID NO: 63); Ser Ile Glu Gin Ser Cys Gly Gln His Glu (SEQ ID NO: 81); Ser Ser Ala Gln Ser Cys Leu Gln Asp Thr (SEQ ID NO: 48); Tyr Ile Glu Gln Tyr Cys Asp Gln Asp Glu (SEQ ID NO: 64); or Thr Ile Trp Gln Ser Cys Asp Gln Glu Glu (SEQ ID NO: 32).

An oligopeptide of the present invention encompasses oligopeptides comprising natural amino acid residues, non-natural amino acid residues, or a mixture of both. An oligopeptide of the present invention encompasses oligopeptides that are modified with a cross-linking agent. The present invention also encompasses oligopeptide polymers comprising at least two oligopeptides of the present invention that are cross-linked, with the proviso that the polymer is not a homopolymer of SEQ ID NO:1 or SEQ ID NO:2. In some examples, the polymer is a dimer, including a homodimer as well as a heterodimer. In other examples, the polymer is a trimer. The present invention encompasses oligopeptide polymers prepared by cross-linking at least two oligopeptides of the present invention, with the proviso that the polymer is not a homopolymer of SEQ ID NO:1 or SEQ ID NO:2.

The present invention encompasses compositions comprising an oligopeptide of the present invention. In some examples, the composition further comprises a pharmaceutically acceptable excipient. In other examples, the composition comprises an agent that enhances transdermal penetration or delivery.

The present invention also provides methods for promoting hair growth in a mammal comprising administering a composition comprising an oligopeptide of the present invention to a mammal in need of hair growth in an amount effective to promote hair growth in said mammal.

The present invention also provides monoclonal antibodies, or fragments thereof, which specifically recognize an antigen of about 220 kDa present in epithelial new follicles. In some examples, the antigen of about 220 kDa present in epithelial new follicles is an antigen which is specifically expressed during the growth period of an imago or the developing period of a fetus. In other examples, the present invention provides a hybridoma deposited with the Patent and Bio-Resource Center of National Institute of Advanced Industrial Science and Technology and having an accession number of FERM P-18578 and a monoclonal antibody made by said hybridoma. In other examples, the present invention provides an antigen, or fragment thereof, recognized by the monoclonal antibody made by the hybridoma deposited with the Patent and Bio-Resource Center of National Institute of Advanced Industrial Science and Technology and having an accession number of FERM P-18578

The present invention also provides a hybridoma produced by the method comprising fusing immunocytes of a mammal immunized with an immunogen containing protein extracted from hair collected from the skin of a mammal in the growth period and/or follicles of whiskers of a mammal in a growth period, and myeloma cells of a mammal. The present invention also provides a process for the production of a monoclonal antibody specific for an antigen of about 220 kDa present in epithelial new follicles, which comprises the steps of incubating the hybridoma deposited with the Patent and Bio-Resource Center of National Institute of Advanced Industrial Science and Technology and having an accession number of FERM P-18578 and collecting the monoclonal antibody produced by said hybridoma.

The present invention also provides methods for the evaluation of hair growth promoting activity comprising the steps of; (1) incubating skin tissue derived from a mammal in the presence of a substance to be tested under suitable conditions and for a time effective to promote hair growth; (2) recovering said skin tissue from step (1); and (3) reacting said skin tissue with the monoclonal antibody made by a hybridoma deposited with the Patent and Bio-Resource Center of National Institute of Advanced Industrial Science and Technology and having an accession number of FERM P-18578 or a fragment thereof; and; (4) detecting said monoclonal antibody or a fragment thereof that reacted with the skin tissue.

The present invention also provides kits comprising a monoclonal antibody made by the hybridoma deposited with the Patent and Bio-Resource Center of National Institute of Advanced Industrial Science and Technology and having an accession number of FERM P-18578

BRIEF DESCRIPTION OF THE DRAWINGS

FIG. 2 shows the result of analysis of the contents of epimorphin (EPM) pep7 based library.

FIG. 3 shows theory values present in epimorphin (EPM) pep7 based library.

FIG. 6 (A) shows the result obtained by a biotinylated oligopeptide. Large square shows the result obtained by oligopeptide b7 (b7 is SIEQSCDQDE (SEQ ID NO: 84)), and small square shows the result obtained by the control (control is a blank). FIG. 6 (B) shows the result obtained by a S-S bridged and biotinylated oligopeptide. Large circle shows the result obtained by oligopeptide ssb7 (cross-linked b7), and small circle shows the result obtained by the control. The vertical axis indicates hair growth score, and the horizontal axis indicates the day from the start of application.

FIGS. 12A–12C show the result of the immune analysis using a monoclonal antibody mAb27 obtained in the present invention. FIG. 12B shows the result of histological staining using hair of adult and 12C maxilla of 14th day mouse embryo.

FIG. 14 shows the amino acid sequence (SEQ ID NO:1) of the human epimorphin coiled coil domain from amino acid residue 1 to amino acid residue 103 as disclosed in EP 0698666A2. The "pep7" region is underlined.

FIG. 15 shows the amino acid sequence (SEQ ID NO:2) of the murine epimorphin coiled coil domain from amino acid residue 1 to amino acid residue 104 as disclosed in EP 0698666A2. The "pep7" region is underlined.

BEST MODE FOR CARRYING OUT THE INVENTION

Figure 1:
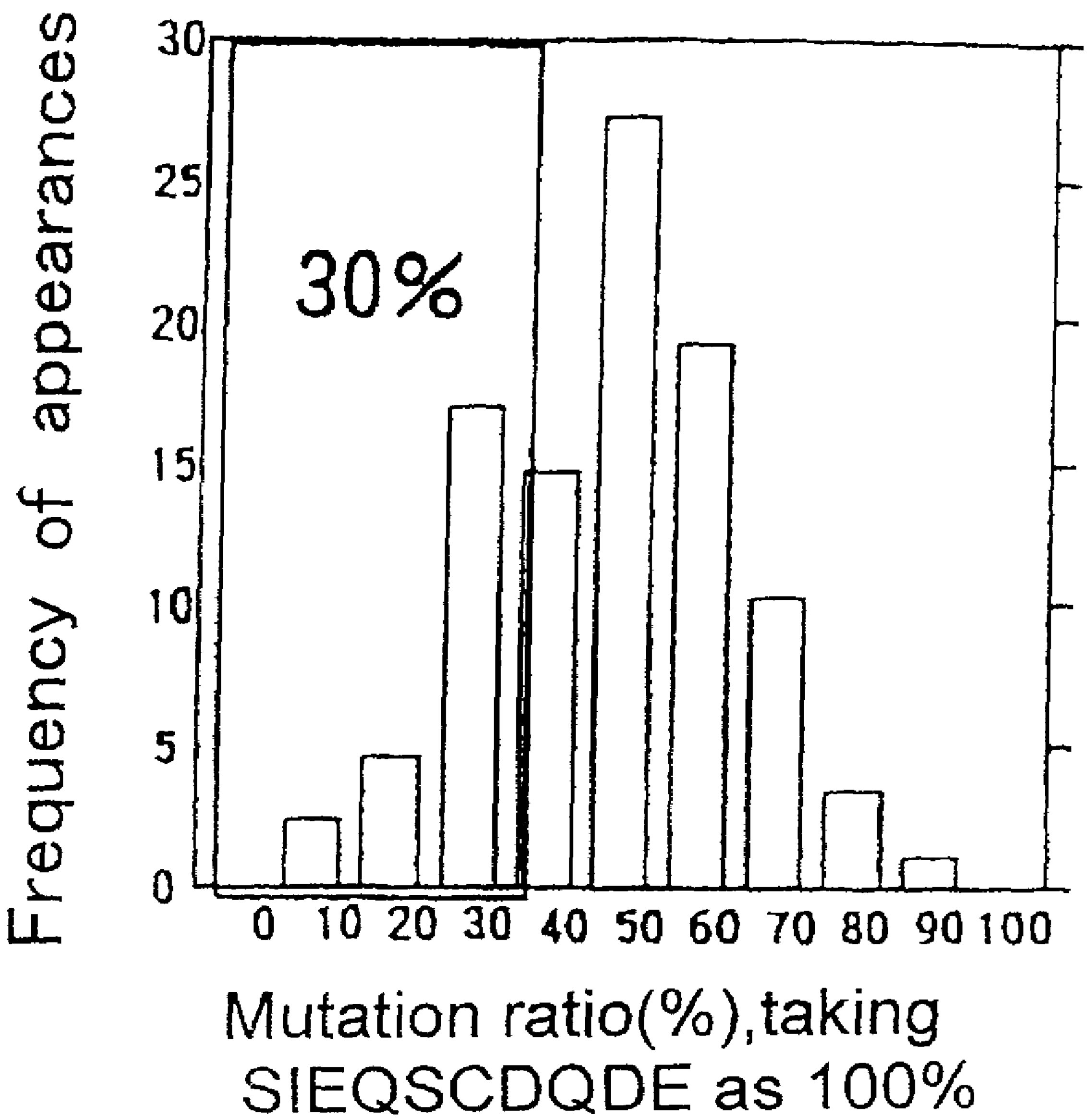
FIG. 1 shows the result of analysis of epimorphin (EPM) pep7 based library. The mutation ratio is shown as a percentage taking a naturally occurring region of murine epimorphin comprising the pep7 region as 100%.

The present invention relates to oligopeptides useful for the treatment or amelioration of symptoms of diseases or disorders associated with abnormal morphogenesis. The oligopeptides of the present invention can be used to induce morphogenesis, induce revascularization effect, induce regeneration effect, induce cardiovascular regeneration, and induce endothelial cell growth. The oligopeptides of the present invention can be used for the treatment of and/or amelioration of symptoms of, for example, burns or wounds or to promote hair growth or prevent hair loss. In particular, the present invention relates to oligopeptides having hair growth promoting activity and to methods of promoting hair growth. The present invention also provide antibodies, including polyclonal antibodies, monoclonal antibodies and fragments thereof, that specifically bind an oligopeptide of the present invention that are useful for the detection, quantitation, separation or purification of the oligopeptides.

The present invention also provides monoclonal antibodies specific for a 220 kDa antigen of epithelial new follicles and methods of assaying for hair growth using such monoclonal antibody. The present invention encompasses monoclonal antibodies specific for a 220 kDa antigen of epithelial new follicles as produced by the hybridoma deposited with the Patent and Bio-Resource Center of National Institute of Advanced Industrial Science and Technology and having accession number FERM P-18578.

The present invention is based, in part, upon the observation that oligopeptides of the present invention have hair growth promoting activity as monomers, that is as a single oligopeptide, and in particular as monomers that are capable of dimerizing under conditions suitable for dimerizing, as monomers having a reactive substance bound, and as polymers, such as, a dimer, including homodimers and heterodimers, and trimers. Hair growth promoting activity can be measured by the assay disclosed herein in Example 7 and by means known to those of skill in the art.

The practice of the present invention will employ, unless otherwise indicated, conventional techniques of molecular biology (including recombinant techniques), cell biology, biochemistry, and immunology, which are within the skill of the art. Such techniques are explained fully in the literature, such as, Molecular Cloning: A Laboratory Manual, Second Edition (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Handbook of Experimental Immunology (D, M. Wei & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987 and annual updates); PCR: The Polymerase Chain Reaction (Mullis et al., eds., 1994); Current Protocols in Immunology (J. E. Coligan et al., eds., 1991 and annual updates).

Epimorphin Sequences

Human and murine epimorphin amino acid sequences are disclosed in U.S. Pat. No. 5,726,298. U.S. Pat. No. 5,726,298 also discloses isoforms of human and murine epimorphin. Human epimorphin pep 7 amino acid region begins at amino acid position 94 of SEQ ID NOS: 3–5 of U.S. Pat. No. 5,726,298 and has the following sequence: Ala-Ile-Glu-Gln-Ser-Phe-Asp (SEQ ID NO:148) and is shown herein in FIG. 14. Murine epimorphin pep7 amino acid region begins at amino acid position 95 of SEQ ID NOS: 9–11 of U.S. Pat. No. 5,726,298 and has the following sequence: Ser-Ile-Glu-Gln-Ser-Cys-Asp (SEQ ID NO: 87) and is shown herein in FIG. 15. In the murine pep7 region, the first Ala of human pep7 is replaced by a Ser and the sixth Phe of human pep7 region is replaced by a Cys.

In the protein of both human and murine epimorphin, the pep7 regions lie in the coiled-coil domain of the respective epimorphins by which polypeptide chains have access to other polypeptide chains for the formation of dimers, even in the absence of Cys in the human epimorphin pep7 region. The present invention is based, in part, upon the observation that mutations of the human epimorphin pep7 region Ala- Ile-Glu-Gln-Ser-Phe-Asp (SEQ ID NO: 148) that comprises a replacement of certain amino acid residues with Cys, demonstrate the ability to induce the morphogenesis of new hair follicles in the mouse model disclosed herein in Example 7. The present invention is further based upon the observation that a pep7 region mutant comprising a Cys in position 6, and which has the ability to dimerize with other pep7 regions that comprise a Cys under conditions that permit dimerization, has activity in the mouse model whereas a pep7 region mutant having a replacement of Cys with Phe, that is that has no Cys, has no activity in the mouse model disclosed herein in the Examples.

Based upon the fact that the pep7 amino acid regions of human and murine are highly conserved and that mutations of the human pep7 regions that comprise a Cys demonstrate activity in the mouse model disclosed herein in Example 7, it is predicted that the oligopeptides disclosed herein will induce hair growth and/or prevent hair loss in humans. Oligopeptides in monomer form and as monomers having a reactive substance bound exhibit hair promoting activity. Oligopeptides in dimer form exhibit the highest activity as measured by the assay disclosed herein in Example 7.

Oligopeptides

Oligopeptides encompassed within the present invention are based on the human or murine epimorphin pep7 amino acid region disclosed in EP 0698666A2 (see also FIGS. 14 and 15, herein) and U.S. Pat. No. 5,726,298. Genes encoding human epimorphin and isoforms thereof are disclosed in U.S. Pat. No. 5,726,298 as SEQ ID NOS: 6, 7 and 8. Genes encoding murine epimorphin and isoforms thereof are disclosed in U.S. Pat. No. 5,726,298 as SEQ ID NOS: 12, 13 and 14.

In some examples, an oligopeptide of the invention comprises or consists of part or all of a naturally occurring murine pep7 region. In other examples, an oligopeptide comprises mutations in and around the human or murine pep7 region, that is, mutations occur within the 7 amino acid pep7 region and may additionally occur within 1–4 amino acids in the N-terminal direction and/or in the C-terminal direction to the pep7 region in human or murine epimorphin. As used herein, a “mutation” includes but it not limited to amino acid substitution(s) and/or deletion(s) and/or insertion (s) and/or addition(s). Oligopeptides of the invention comprise between about 5 to about 104 amino acid residues in length, and, in some examples have the amino acid sequence as disclosed herein in SEQ ID NOs: 3–135, with the proviso that the oligopeptide is not identical to SEQ ID NO: 1 or SEQ ID NO:2 and maintain at least one biological activity. In some examples, an oligopeptide consists of a pep7 region or pep7 region mutation, as long as the oligopeptide maintains at least one biological activity. In other examples, an oligopeptide comprises a pep7 region or pep7 region mutation and, in particular, as disclosed herein in SEQ ID NOs: 3–135, as long as the oligopeptide maintains at least one biological activity. The present invention encompasses oligopeptides comprising a pep7 region or pep7 region mutation as disclosed herein and, in particular, as disclosed herein in SEQ ID NOs: 3–135, and in some examples, the amino acid residues in the N-terminal direction and/or the C-terminal direction to the pep7 region or pep7 region mutation in the oligopeptide are the naturally occurring amino acid sequences in the N-terminal direction and/or the C-terminal direction to human or murine epimorphin pep7 region and may be of any length up to and including full length human and murine epimorphin or any isoform of human or murine epimorphin, as long as the oligopeptide maintains at least one biological activity, with the proviso that the oligopeptide is not identical to SEQ ID NO: 1 or SEQ ID NO:2.

The present invention encompasses oligopeptides comprising a pep7 region or pep7 region mutation as disclosed herein and, in particular, as disclosed herein in SEQ ID NOs: 3–135, and in some examples, the amino acid residues in the N-terminal direction and/or the C-terminal direction to the pep7 region or pep7 region mutation in the oligopeptide comprise substitution(s), in particular conservative substitution(s) and/or, deletion(s) and/or, addition(s) and/or insertion(s) to the naturally occurring amino acid sequences in the N-terminal direction and/or the C-terminal direction to human or murine epimorphin pep7 region or any isoform of human or murine epimorphin and may be of any length up to and including full length human and murine epimorphin, as long as the oligopeptide maintains at least one biological activity, with the proviso that the oligopeptide is not identical to SEQ ID NO: 1 or SEQ ID NO:2. In other examples, the amino acid residues in the N-terminal direction and/or the C-terminal direction to the pep7 region or pep7 region mutation in the oligopeptide are the naturally occurring amino acid sequences in the N-terminal direction and/or the C-terminal direction to a mammalian epimorphin pep7 region or comprise substitutions, in particular conservative substitution(s) and/or, deletion(s), and/or addition(s) and/or insertions to naturally occurring amino acid sequences in the N-terminal direction and/or the C-terminal direction to a mammalian epimorphin pep7 region, as long as the oligopeptide maintains at least one biological activity. In some examples, an oligopeptide is soluble in aqueous medium such as saline or water. In other examples, the oligopeptide is capable of dimerizing under suitable conditions.

The present invention encompasses isolated oligopeptides of between about 5 and about 104 amino acid residues in length exhibiting hair growth promoting activity comprising the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Ala, Tyr, Thr, Pro, Phe, Val, Gly, Leu, Ile or Met, or is deleted from said oligopeptide;

X2 is an amino acid residue of Ile, Gly, Asn, Thr, Val, Ser, Phe, Leu, Ala, Pro, Cys, or Met, or is deleted from said oligopeptide;

X3 is an amino acid residue of Glu, Lys, Gln, Arg, Ala, Val, Trp, Cys, or Asp;

X4 is an amino acid residue of Gln, Pro, Glu, Thr, Arg, Ser, His, Cys, or Lys;

X5 is an amino acid residue of Ser, Trp, Phe, Thr, Cys, Tyr, Pro, Ala, Gly, Val, Leu, Ile, or Met;

X6 is an amino acid residue Cys; a reactive substance-bound Cys or a reactive substance-bound Lys; and X7 is an amino acid residue of Asp, Glu, His, Ser, Ala, Gly, Asn, Tyr, Arg, or Leu, or is deleted from said oligopeptide, with the proviso that the oligopeptide is not identical to SEQ ID NO:1 or SEQ ID NO:2.

The present invention also encompasses isolated oligopeptides of between about 5 and about 104 amino acid residues in length having hair growth promoting activity comprising the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Tyr, Thr, or Pro, or is deleted from said oligopeptide;

X2 is an amino acid residue of Ile, Asn, Thr, or Ser, or is deleted from said oligopeptide;

X3 is an amino acid residue of Glu, Ala, Trp, or Asp;

X4 is an amino acid residue of Gln;

X5 is an amino acid residue of Ser, Cys, or Tyr;

X6 is an amino acid residue of Cys; a reactive substance-bound Cys or a reactive substance-bound Lys; and X7 is an amino acid residue of Asp, Ala, Gly, or Leu, or is deleted from said oligopeptide, with the proviso that the oligopeptide is not SEQ ID NO:2.

The present invention also encompasses isolated oligopeptides of between about 7 and about 100 amino acid residues in length exhibiting hair growth promoting activity comprising the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Ala, Tyr, Thr, Pro, Phe, Val, Gly, Leu, Ile or Met, or is deleted from said oligopeptide;

X2 is an amino acid residue of Ile, Gly, Asn, Thr, Val, Ser, Phe, Leu, Ala, Pro, Cys, or Met, or is deleted from said oligopeptide;

X3 is an amino acid residue of Glu, Lys, Gln, Arg, Ala, Val, Trp, Cys, or Asp;

X4 is an amino acid residue of Gln, Pro, Glu, Thr, Arg, Ser, His, Cys, or Lys;

X5 is an amino acid residue of Ser, Trp, Phe, Thr, Cys, Tyr, Pro, Ala, Gly, Val, Leu, Ile, or Met;

X6 is an amino acid residue of Cys; and

X7 is an amino acid residue of Asp, Glu, His, Ser, Ala, Gly, Asn, Tyr, Arg, or Leu, or is deleted from said oligopeptide.

The present invention also encompasses isolated oligopeptides of between about 7 and about 100 amino acid residues in length exhibiting hair growth promoting activity comprising the following formula:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Tyr, Thr, or Pro, or is deleted from said oligopeptide;

X2 is an amino acid residue of Ile, Asn, Thr, or Ser, or is deleted from said oligopeptide;

X3 is an amino acid residue of Glu, Ala, Trp, or Asp;

X4 is an amino acid residue of Gln;

X5 is an amino acid residue of Ser, Cys, or Tyr;

X6 is an amino acid residue of Cys; and

X7 is an amino acid residue of Asp, Ala, Gly, or Leu, or is deleted from said oligopeptide.

The present invention also encompasses isolated oligopeptides comprising the following amino acid sequence that exhibit hair growth promoting activity: T/Y-S/N-E-Q-S-C-A. (SEQ ID NO:3).

Isolated oligopeptides comprising an amino acid sequence as shown in any of SEQ ID NO: 3–135 disclosed herein are encompassed within the present invention. In some embodiments, an oligopeptide will consist of an amino acid sequence as shown in any of SEQ ID NO: 3–135 and in other embodiments, and oligopeptide will comprise an amino acid sequence as shown in any of SEQ ID NO: 3–135. As used herein, as "isolated" oligopeptide refers to an oligopeptide that is removed from at least one component with which it is naturally associated.

The present invention further encompasses the following oligopeptides that exhibit hair growth promoting activity:

oligopeptides comprising 7 to 100 amino acid residues in length, which comprise an amino acid sequence wherein 1 to 3 amino acid residues are substituted in the amino acid sequence Ser-Ile-Glu-Gln-Ser-Cys-Asp (SEQ ID NO: 67) wherein the amino acid residue to be substituted is other than Cys or the amino acid residue to be substituted is other than the third to sixth amino acid residues Glu-Gln-Ser-Cys (SEQ ID NO: 120);

oligopeptides comprising 5 to 100 amino acid residues in length, which comprise an amino acid sequence wherein 0 to 2 amino acid residues are substituted in the amino acid sequence represented by Glu-Gln-Ser-Cys-Asp (SEQ ID NO: 111); wherein the amino acid residue to be substituted is other than Cys or the amino acid residue to be substituted is other than the third to sixth amino acid residues Glu-Gln-Ser-Cys (SEQ ID NO: 120);

oligopeptides comprising 7 to 100 amino acid residues in length, wherein the first Ser is substituted with a hydrophobic amino acid residue or a neutral amino acid residue in the amino acid sequence of Ser-Ile-Glu-Gln-Ser-Cys-Asp (SEQ ID NO: 67);

oligopeptides comprising 7 to 100 amino acid residues in length wherein the first Ser is substituted with Ala, Tyr, Thr, Pro, Phe, Val or Gly in the amino acid sequence of Ser-Ile-Glu-Gln-Ser-Cys-Asp (SEQ ID NO: 67);

oligopeptides comprising 7 to 100 amino acid residues in length wherein the second Ile is substituted with a neutral amino acid residue or a hydrophobic amino acid residue in the amino acid sequence of Ser-Ile-Glu-Gln-Ser-Cys-Asp (SEQ ID NO: 87);

oligopeptides comprising 7 to 100 amino acid residues in length wherein the second Ile is substituted with Gly, Asn, Thr, Val, Ser, Phe or Leu in the amino acid sequence of Ser-Ile-Glu-Gln-Ser-Cys-Asp (SEQ ID NO: 87);

oligopeptides comprising 7 to 100 amino acid residues in length wherein the fifth Ser is substituted with a neutral amino acid residue or a hydrophobic amino acid residue in the amino acid sequence of Ser-Ile-Glu-Gln-Ser-Cys-Asp (SEQ ID NO: 87);

oligopeptides comprising 7 to 100 amino acid residues in length wherein the fifth Ser is substituted with Trp, Phe, Thr, Cys, Tyr, Pro or Ala in the amino acid sequence of Ser-Ile-Glu-Gln-Ser-Cys-Asp (SEQ ID NO: 87);

oligopeptides comprising 7 to 100 amino acid residues in length wherein the seventh Asp is substituted with a hydrophilic amino acid residue, Gly, Ala or Leu in the amino acid sequence of Ser-Ile-Glu-Gln-Ser-Cys-Asp (SEQ ID NO: 87);

oligopeptides comprising 7 to 100 amino acid residues in length wherein the seventh Asp is substituted with Glu, His, Ser, Ala, Gly, Asn, Tyr or Leu in the amino acid sequence of Ser-Ile-Glu-Gln-Ser-Cys-Asp (SEQ ID NO: 87);

oligopeptides comprising 7 to 100 amino acid residues in length wherein the third Glu is substituted with Lys, Gly, Gln, Arg, Ala, Val Asp or Trp in the amino acid sequence of Ser-Ile-Glu-Gln-Ser-Cys-Asp (SEQ ID NO: 87);

oligopeptides comprising 7 to 100 amino acid residues in length wherein the fourth Gln is substituted with Pro, Glu, Thr, Arg, Ser, His or Lys in the amino acid sequence of Ser-Ile-Glu-Gln-Ser-Cys-Asp (SEQ ID NO: 87);

oligopeptides comprising 7 to 100 amino acid residues in length wherein the first Ser is substituted with Thr or Tyr, the second Ile is substituted with Ser, Asn or Thr, the third Glu is substituted with Ala, Asp or Trp, the fifth Ser is substituted with Cys or Tyr, and/or the seventh Asp is substituted with Gly, Ala or Leu in the amino acid sequence of Ser-Ile-Glu-Gln-Ser-Cys-Asp (SEQ ID NO: 87);

oligopeptides comprising 7 to 100 amino acid residues in length wherein 1 to 3 amino acid residues other than the third to sixth amino acid residues Glu-Gln-Ser-Cys (SEQ ID NO: 120) are substituted in the amino acid sequence of Ser-Ile-Glu-Gln-Ser-Cys-Asp (SEQ ID NO: 87), the first Ser is substituted with Thr or Tyr, the second Ile is substituted with Ser, Asn or Thr, and/or the seventh Asp is substituted with Gly, Ala or Leu;

oligopeptides comprising 7 to 100 amino acid residues in length which comprises at least an amino acid sequence wherein 1 to 3 amino acid residues are substituted in the amino acid sequence represented by Ser-Ile-Glu-Gln-Cys-Ser-Asp (SEQ ID NO: 4) wherein the amino acid residue to be substituted is other than Cys or other than the third to sixth amino acid residues Glu-Gln-Cys-Ser (SEQ ID NO: 152);

oligopeptides comprising 5 to 100 amino acid residues in length which comprises an amino acid sequence wherein 0 to 2 amino acid residues are substituted in the amino acid sequence represented by Glu-Gln-Cys-Ser-Asp (SEQ ID NO: 112); wherein the amino acid residue to be substituted is other than Cys or other than the third to sixth amino acid residues Glu-Gln-Cys-Ser (SEQ ID NO: 152);

oligopeptides comprising 7 to 100 amino acid residues in length wherein the first Ser is substituted with a hydrophobic amino acid residue or a neutral amino acid residue in the amino acid sequence of Ser-Ile-Glu-Gln-Cys-Ser-Asp (SEQ ID NO: 4);

oligopeptides comprising 7 to 100 amino acid residues in length wherein the first Ser is substituted with Ala, Tyr, Thr, Pro, Phe, Val or Gly in the amino acid sequence of Ser-Ile-Glu-Gln-Cys-Ser-Asp (SEQ ID NO: 4);

oligopeptides comprising 7 to 100 amino acid residues in length wherein the second Ile is substituted with a neutral amino acid residue or a hydrophobic amino acid residue in the amino acid sequence of Ser-Ile-Glu-Gln-Cys-Ser-Asp (SEQ ID NO: 4);

oligopeptides comprising 7 to 100 amino acid residues in length wherein the second Ile is substituted with Gly, Asn, Thr, Val, Ser, Phe or Leu in the amino acid sequence of Ser-Ile-Glu-Gln-Cys-Ser-Asp (SEQ ID NO: 4);

oligopeptides comprising 7 to 100 amino acid residues in length wherein the sixth Ser is substituted with a neutral amino acid residue or a hydrophobic amino acid residue in the amino acid sequence of Ser-Ile-Glu-Gln-Cys-Ser-Asp (SEQ ID NO: 4);

oligopeptides comprising 7 to 100 amino acid residues in length wherein the sixth Ser is substituted with Trp, Phe, Thr, Cys, Tyr, Pro or Ala in the amino acid sequence of Ser-Ile-Glu-Gln-Cys-Ser-Asp (SEQ ID NO: 4);

oligopeptides comprising 7 to 100 amino acid residues in length wherein the seventh Asp is substituted with a hydrophilic amino acid residue, Gly, Ala or Leu in the amino acid sequence of Ser-Ile-Glu-Gln-Cys-Ser-Asp (SEQ ID NO: 4);

oligopeptides comprising 7 to 100 amino acid residues in length wherein the seventh Asp is substituted with Glu, His, Ser, Ala, Gly, Asn, Tyr or Leu in the amino acid sequence of Ser-Ile-Glu-Gln-Cys-Ser-Asp (SEQ ID NO: 4);

oligopeptides comprising 7 to 100 amino acid residues in length wherein the third Glu is substituted with Lys, Gly, Gln, Arg, Ala, Val, Asp or Trp in the amino acid sequence of Ser-Ile-Glu-Gln-Cys-Ser-Asp (SEQ ID NO: 4);

oligopeptides comprising 7 to 100 amino acid residues in length wherein the fourth Gln is substituted with Pro, Glu, Thr, Arg, Ser, His or Lys in the amino acid sequence of Ser-Ile-Glu-Gln-Cys-Ser-Asp (SEQ ID NO: 4);

oligopeptides comprising 7 to 100 amino acid residues in length wherein the first Ser is substituted with Thr or Tyr, the second Ile is substituted with Ser, Asn or Thr, the third Glu is substituted with Ala, Asp or Trp, the sixth Ser is substituted with Cys or Tyr, and/or the seventh Asp is substituted with Gly, Ala or Leu in the amino acid sequence of Ser-Ile-Glu-Gln-Cys-Ser-Asp (SEQ ID NO: 4);

oligopeptides comprising 7 to 100 amino acid residues in length wherein 1 to 3 amino acid residues other than the third to sixth amino acid residues Glu-Gln-Cys-Ser (SEQ ID NO: 152) are substituted in the amino acid sequence of Ser-Ile-Glu-Gln-Cys-Ser-Asp (SEQ ID NO: 4), the first Ser is substituted with Thr or Tyr, the second Ile is substituted with Ser, Asn or Thr, and/or the seventh Asp is substituted with Gly, Ala or Leu;

oligopeptides comprising 7 to 100 amino acid residues in length which comprises at least an amino acid sequence wherein 1 to 3 amino acid residues are substituted in the amino acid sequence represented by Ser-Ile-Glu-Cys-Gln-Ser-Asp (SEQ ID NO: 5) wherein the amino acid residue to be substituted is other than Cys or wherein the amino acid residue to be substituted is other than the third to sixth amino acid residues Glu-Cys-Gln-Ser (SEQ ID NO: 153);

oligopeptides comprising 5 to 100 amino acid residues in length which comprise an amino acid sequence wherein 0 to 2 amino acid residues are substituted in the amino acid sequence represented by Glu-Cys-Gln-Ser-Asp (SEQ ID NO: 113); wherein the amino acid residue to be substituted is other than Cys or wherein the amino acid residue to be substituted is other than the third to sixth amino acid residues Glu-Cys-Gln-Ser (SEQ ID NO: 153);

oligopeptides comprising 7 to 100 amino acid residues in length wherein the first Ser is substituted with a hydrophobic amino acid residue or a neutral amino acid residue in the amino acid sequence of Ser-Ile-Glu-Cys-Gln-Ser-Asp (SEQ ID NO: 5);

oligopeptides comprising 7 to 100 amino acid residues in length wherein the first Ser is substituted with Ala, Tyr, Thr, Pro, Phe, Val or Gly in the amino acid sequence of Ser-Ile-Glu-Cys-Gln-Ser-Asp (SEQ ID NO: 5);

oligopeptides comprising 7 to 100 amino acid residues in length wherein the second Ile is substituted with a neutral amino acid residue or a hydrophobic amino acid residue in the amino acid sequence of Ser-Ile-Glu-Cys-Gln-Ser-Asp (SEQ ID NO: 5);

oligopeptides comprising 7 to 100 amino acid residues in length wherein the second Ile is substituted with Gly, Asn, Thr, Val, Ser, Phe or Leu in the amino acid sequence of Ser-Ile-Glu-Cys-Gln-Ser-Asp (SEQ ID NO: 5);

oligopeptides comprising 7 to 100 amino acid residues in length wherein the sixth Ser is substituted with a neutral amino acid residue or a hydrophobic amino acid residue in the amino acid sequence of Ser-Ile-Glu-Cys-Gln-Ser-Asp (SEQ ID NO: 5);

oligopeptides comprising 7 to 100 amino acid residues in length wherein the sixth Ser is substituted with Trp, Phe, Thr, Cys, Tyr, Pro or Ala in the amino acid sequence of Ser-Ile-Glu-Cys-Gln-Ser-Asp (SEQ ID NO: 5);

oligopeptides comprising 7 to 100 amino acid residues in length wherein the seventh Asp is substituted with a hydrophilic amino acid residue, Gly, Ala or Leu in the amino acid sequence of Ser-Ile-Glu-Cys-Gln-Ser-Asp (SEQ ID NO: 5);

oligopeptide comprising 7 to 100 amino acid residues in length wherein the seventh Asp is substituted with Glu, His, Ser, Ala, Gly, Asn, Tyr or Leu in the amino acid sequence of Ser-Ile-Glu-Cys-Gln-Ser-Asp (SEQ ID NO: 5);

oligopeptides comprising 7 to 100 amino acid residues in length wherein the third Glu is substituted with Lys, Gly, Gln, Arg, Ala, Val, Asp or Trp in the amino acid sequence of Ser-Ile-Glu-Cys-Gln-Ser-Asp (SEQ ID NO: 5);

oligopeptides comprising 7 to 100 amino acid residues in length wherein the fifth Gln is substituted with Pro, Glu, Thr, Arg, Ser, His or Lys in the amino acid sequence of Ser-Ile-Glu-Cys-Gln-Ser-Asp (SEQ ID NO: 5);

oligopeptides comprising 7 to 100 amino acid residues in length wherein the first Ser is substituted with Thr or Tyr, the second Ile is substituted with Ser, Asn or Thr, the third Glu is substituted with Ala, Asp or Trp, the sixth Ser is substituted with Cys or Tyr, and/or the seventh Asp is substituted with Gly, Ala or Leu in the amino acid sequence of Ser-Ile-Glu-Cys-Gln-Ser-Asp (SEQ ID NO: 5);

oligopeptides comprising 7 to 100 amino acid residues in length wherein 1 to 3 amino acid residues other than the third to sixth amino acid residues Glu-Cys-Gln-Ser (SEQ ID NO: 153) are substituted in the amino acid sequence of Ser-Ile-Glu-Cys-Gln-Ser-Asp (SEQ ID NO: 5), the first Ser is substituted with Thr or Tyr, the second Ile is substituted with Ser, Asn or Thr, and/or the seventh Asp is substituted with Gly, Ala or Leu;

oligopeptides comprising 7 to 100 amino acid residues in length which comprises at least an amino acid sequence wherein 1 to 3 amino acid residues are substituted in the amino acid sequence represented by Ser-Ile-Cys-Glu-Gln-Ser-Asp (SEQ ID NO: 6) wherein the amino acid residue to be substituted is other than Cys or other than the third to sixth amino acid residues Cys-Glu-Gln-Ser (SEQ ID NO: 154);

oligopeptides comprising 5 to 100 amino acid residues in length which comprises an amino acid sequence wherein 0 to 2 amino acid residues are substituted in the amino acid sequence represented by Cys-Glu-Gln-Ser-Asp (SEQ ID NO: 114), wherein the amino acid residue to be substituted is other than Cys or other than the third to sixth amino acid residues Cys-Glu-Gln-Ser (SEQ ID NO: 154);

oligopeptides comprising 7 to 100 amino acid residues in length wherein the first Ser is substituted with a hydrophobic amino acid residue or a neutral amino acid residue in the amino acid sequence of Ser-Ile-Cys-Glu-Gln-Ser-Asp (SEQ ID NO: 6);

oligopeptides comprising 7 to 100 amino acid residues in length wherein the first Ser is substituted with Ala, Tyr, Thr, Pro, Phe, Val or Gly in the amino acid sequence of Ser-Ile-Cys-Glu-Gln-Ser-Asp (SEQ ID NO: 6);

oligopeptides comprising 7 to 100 amino acid residues in length wherein the second Ile is substituted with a neutral amino acid residue or a hydrophobic amino acid residue in the amino acid sequence of Ser-Ile-Cys-Glu-Gln-Ser-Asp (SEQ ID NO: 6);

oligopeptides comprising 7 to 100 amino acid residues in length wherein the second Ile is substituted with Gly, Asn, Thr, Val, Ser, Phe or Leu in the amino acid sequence of Ser-Ile-Cys-Glu-Gln-Ser-Asp (SEQ ID NO: 6);

oligopeptides comprising 7 to 100 amino acid residues in length wherein the sixth Ser is substituted with a neutral amino acid residue or a hydrophobic amino acid residue in the amino acid sequence of Ser-Ile-Cys-Glu-Gln-Ser-Asp (SEQ ID NO: 6);

oligopeptides comprising 7 to 100 amino acid residues in length wherein the sixth Ser is substituted with Trp, Phe, Thr, Cys, Tyr, Pro or Ala in the amino acid sequence of Ser-Ile-Cys-Glu-Gln-Ser-Asp (SEQ ID NO: 6);

oligopeptides comprising 7 to 100 amino acid residues in length wherein the seventh Asp is substituted with a hydrophilic amino acid residue, Gly, Ala or Leu in the amino acid sequence of Ser-Ile-Cys-Glu-Gln-Ser-Asp (SEQ ID NO: 6);

oligopeptides comprising 7 to 100 amino acid residues in length wherein the seventh Asp is substituted with Glu, His, Ser, Ala, Gly, Asn, Tyr or Leu in the amino acid sequence of Ser-Ile-Cys-Glu-Gln-Ser-Asp (SEQ ID NO: 6);

oligopeptides comprising 7 to 100 amino acid residues in length wherein the fourth Glu is substituted with Lys, Gly, Gln, Arg, Ala, Val, Asp or Tip in the amino acid sequence of Ser-Ile-Cys-Glu-Gln-Ser-Asp (SEQ ID NO: 6);

oligopeptides comprising 7 to 100 amino acid residues in length wherein the fifth Gln is substituted with Pro, Glu, Thr, Arg, Ser, His or Lys in the amino acid sequence of Ser-Ile-Cys-Glu-Gln-Ser-Asp (SEQ ID NO: 6);

oligopeptides comprising 7 to 100 amino acid residues in length wherein the first Ser is substituted with Thr or Tyr, the second Ile is substituted with Ser, Asn or Thr, the fourth Glu is substituted with Ala, Asp or Trp, the sixth Ser is substituted with Cys or Tyr, and/or the seventh Asp is substituted with Gly, Ala or Leu in the amino acid sequence of Ser-Ile-Cys-Glu-Gln-Ser-Asp (SEQ ID NO: 6);

oligopeptides comprising 7 to 100 amino acid residues in length wherein 1 to 3 amino acid residues other than the third to sixth amino acid residues Cys-Glu-Gln-Ser (SEQ ID NO: 154) are substituted in the amino acid sequence of Ser-Ile-Cys-Glu-Gln-Ser-Asp (SEQ ID NO: 6), the first Ser is substituted with Thr or Tyr, the second Ile is substituted with Ser, Asn or Thr, and/or the seventh Asp is substituted with Gly, Ala or Leu;

oligopeptides comprising 5 to 100 amino acid residues in length which comprises at least an amino acid sequence wherein 1 to 3 amino acid residues are substituted in the amino acid sequence represented by Glu-Gln-Ser-Cys-Asp (SEQ ID NO: 111);

oligopeptides comprising 5 to 100 amino acid residues in length which comprises at least an amino acid sequence wherein 1 to 3 amino acid residues are substituted in the amino acid sequence represented by Glu-Gln-Cys-Ser-Asp (SEQ ID NO: 112);

oligopeptides comprising 5 to 100 amino acid residues in length which comprises at least an amino acid sequence wherein 1 to 3 amino acid residues are substituted in the amino acid sequence represented by Glu-Cys-Gln-Ser-Asp (SEQ ID NO: 113); and oligopeptides comprising 5 to 100 amino acid residues in length which comprises at least an amino acid sequence wherein 1 to 3 amino acid residues are substituted in the amino acid sequence represented by Cys-Glu-Gln-Ser-Asp (SEQ ID NO: 114).

Without wanted to be bound to theory, it is theorized that to obtain an oligopeptide having amino acid substitutions which will have a similar morphogenesis activity, such as for example, a similar hair growth promoting activity, with the unsubstituted oligopeptide, it is preferred that the newly added amino acid residue in the pep7 region of epimorphin has a similar property to the deleted amino acid residue. Specifically, 5 types (7 positions in total, that is the 7 underlined positions of S I E Q S C D Q D E) (SEQ ID NO: 84) of amino acid residues of Ser (at 2 positions), Ile, Glu, Gln (at 2 positions) and Asp can be substituted in the amino acid sequence of a pep7 region from murine epimorphin. Among them, Ser (serine) can be substituted with Thr (threonine) belonging to hydroxyamino acids; Ile (isoleucine) can be substituted with Gly (glycine), Ala (alanine), Val (valine) or Leu (leucine) which are aliphatic amino acids; Glu (glutamic acid) can be substituted with Asp (aspartic acid) which is acidic amino acids; Gln (glutamine) can be substituted with Asn (asparagine) which is an amide; and Asp (aspartic acid) can be substituted with Glu (glutamic acid) which is acidic amino acids. These are preferred examples of substitution, and the amino acid can be substituted with any other amino acid as long as at least one biological activity is maintained.

Oligopeptides comprising the following amino acid sequences demonstrated hair growth promoting activity as measured in the assay described herein in Example 7, which measures the amount of mAb27 antigen in skin in vitro.

| | |
|---|---|
| Ser-Ile-Glu-Gln-Cys-Ser-Asp; | (SEQ ID NO:4) |
| Ser-Ile-Glu-Cys-Gln-Ser-Asp; | (SEQ ID NO:5) |
| Ser-Ile-Cys-Glu-Gln-Ser-Asp; | (SEQ ID NO:6) |
| Tyr-Asn-Glu-Gln-Ser-Cys-Asp; | (SEQ ID NO:7) |
| Thr-Ser-Asp-Gln-Cys-Cys-Asp; | (SEQ ID NO:8) |
| Ser-Ile-Glu-Gln-Ser-Cys-Gly; | (SEQ ID NO:9) |
| Ser-Ser-Ala-Gln-Ser-Cys-Leu; | (SEQ ID NO:10) |
| Tyr-Ile-Glu-Gln-Tyr-Cys-Asp; | (SEQ ID NO:11) |
| Thr-Ile-Trp-Gln-Ser-Cys-Asp; | (SEQ ID NO:12) |
| Thr-Thr-Glu-Gln-Ser-Cys-Ala; | (SEQ ID NO:13) |
| Pro-Ser-Glu-Gln-Ser-Cys-Ala; and | (SEQ ID NO:14) |
| Ser-Asn-Glu-Gln-Ser-Cys-Ala. | (SEQ ID NO:15) |

Additional oligopeptides comprising amino acid sequences demonstrating hair growth promoting activity are shown in Table 1 below in one letter amino acid code (wherein the designation X refers to an undetermined amino acid and * refers to a stop codon).

TABLE I

| | |
|---|---|
| YIKQSCEQDE | (SEQ ID NO:16) |
| YNEQSCDREE | (SEQ ID NO:17) |
| SVEQSCHRGE | (SEQ ID NO:18) |
| SSEQTCDQHG | (SEQ ID NO:19) |
| STGQSCDQPG | (SEQ ID NO:20) |
| TTEQSCDQQE | (SEQ ID NO:21) |
| SIRQFCDQDV | (SEQ ID NO:22) |
| TTEQSCDQQE | (SEQ ID NO:23) |
| SNEPCSDQGG | (SEQ ID NO:24) |
| FIEQSCDQNE | (SEQ ID NO:25) |
| SXEXSCDQDQ | (SEQ ID NO:26) |
| TSQQSCDLDE | (SEQ ID NO:27) |
| VNEQSCDQDE | (SEQ ID NO:28) |
| SNEQSCAVAE | (SEQ ID NO:29) |
| SIEQSCDQDW | (SEQ ID NO:30) |
| SIEQSCDQDV | (SEQ ID NO:31) |
| TIWQSCDQEE | (SEQ ID NO:32) |
| SSAQSCL | (SEQ ID NO:10) |
| PSEQSCA | (SEQ ID NO:14) |
| TIEQSCDEVA | (SEQ ID NO:33) |
| STEQSCHKVE | (SEQ ID NO:34) |
| SSEQWCSQDQ | (SEQ ID NO:35) |
| SFEQSCDQHE | (SEQ ID NO:36) |
| SNEESCDLDE | (SEQ ID NO:37) |
| SIKQSCDPHQ | (SEQ ID NO:38) |
| GLEQSCDQDW | (SEQ ID NO:39) |
| TGEQSCDQHE | (SEQ ID NO:40) |
| SIEQSCAPAF | (SEQ ID NO:41) |
| PIKTSCDQEE | (SEQ ID NO:42) |
| SIERSCDQDE | (SEQ ID NO:43) |
| SSERSCDPDE | (SEQ ID NO:44) |
| VIEQACDQNE | (SEQ ID NO:45) |
| AIEQSCDQVE | (SEQ ID NO:46) |
| SIEQSCNQDE | (SEQ ID NO:47) |
| SSAQSCLQDT | (SEQ ID NO:48) |
| YNEQSCD | (SEQ ID NO:7) |
| YIEQYCD | (SEQ ID NO:11) |
| SNEQSCA | (SEQ ID NO:15) |
| YGEQSCDQGQ | (SEQ ID NO:49) |
| SVEQSCDPND | (SEQ ID NO:50) |
| SIEQFCEQGW | (SEQ ID NO:51) |
| SLEQSCDQDK | (SEQ ID NO:52) |

TABLE I-continued

| | |
|---|---|
| SIEQSCDAHQ | (SEQ ID NO:53) |
| SIEQFCNPDE | (SEQ ID NO:54) |
| PIGPSCDKPV | (SEQ ID NO:55) |
| SIVQSCGEAE | (SEQ ID NO:56) |
| TGEQSCDQHE | (SEQ ID NO:57) |
| FIEQSCDQHV | (SEQ ID NO:58) |
| PIEQSCYQHG | (SEQ ID NO:59) |
| STEQPCDQGL | (SEQ ID NO:60) |
| PSEQSCAEEE | (SEQ ID NO:61) |
| SIEQPCHQRV | (SEQ ID NO:62) |
| TTEQSCAVDE | (SEQ ID NO:63) |
| YIEQYCDQDE | (SEQ ID NO:64) |
| TSDQCCD | (SEQ ID NO:65) |
| TIWQSCD | (SEQ ID NO:66) |
| SIEQSCD* | (SEQ ID NO:67) |
| YGEQSCDQGQ | (SEQ ID NO:68) |
| SIEQSCDLHE | (SEQ ID NO:69) |
| SIEQSCSQXX | (SEQ ID NO:70) |
| SIEQSCDQDE | (SEQ ID NO:71) |
| SNEPSCXEDG | (SEQ ID NO:72) |
| SSEHSCDHDE | (SEQ ID NO:73) |
| PIKTSCDQFE | (SEQ ID NO:74) |
| YNEQSCDQDE | (SEQ ID NO:75) |
| TSDQCCDPDK | (SEQ ID NO:76) |
| SIESSCDTAE | (SEQ ID NO:77) |
| SFQQSCEQNE | (SEQ ID NO:78) |
| SSEQFCDQGK | (SEQ ID NO:79) |
| SIEQACGQGE | (SEQ ID NO:80) |
| SIEQSCGQHE | (SEQ ID NO:81) |
| SVEKPCDLVV | (SEQ ID NO:82) |
| SIEQSCG | (SEQ ID NO:9) |
| TTEQSCA | (SEQ ID NO:13) |

Additional oligopeptides comprising the following amino acid sequences demonstrating hair growth promoting activity are encompassed within the present invention.

| | |
|---|---|
| Lys-Ser-Ile-Glu-Gln-Ser-Cys-Asp-Gln-Asp-Glu; | (SEQ ID NO:83) |
| Ser-Ile-Glu-Gln-Ser-Cys-Asp-Gln-Asp-Glu; | (SEQ ID NO:84) |
| Ser-Ile-Glu-Gln-Ser-Cys-Asp-Gln-Asp; | (SEQ ID NO:85) |

-continued

| | |
|---|---|
| Ser-Ile-Glu-Gln-Ser-Cys-Asp-Gln; | (SEQ ID NO:86) |
| Ser-Ile-Glu-Gln-Ser-Cys-Asp; | (SEQ ID NO:87) |
| Ser-Ile-Glu-Gln-Ser-Cys; | (SEQ ID NO:88) |
| Ile-Glu-Gln-Ser-Cys-Asp-Gln-Asp-Glu; | (SEQ ID NO:89) |
| Glu-Gln-Ser-Cys-Asp-Gln-Asp-Glu, or; | (SEQ ID NO:90) |
| Gln-Ser-Cys-Asp-Gln-Asp-Glu; | (SEQ ID NO:91) |
| Ser-Ile-Glu-Gln-Cys-Ser-Asp-Gln; | (SEQ ID NO:92) |
| Ser-Ile-Glu-Cys-Gln-Ser-Asp-Gln; | (SEQ ID NO:93) |
| Ser-Ile-Cys-Glu-Gln-Ser-Asp-Gln; | (SEQ ID NO:94) |
| Thr-Ser-Glu-Gln-Ser-Cys-Ala; | (SEQ ID NO:95) |
| Thr-Asn-Glu-Gln-Ser-Cys-Ala; | (SEQ ID NO:96) |
| Tyr-Ser-Glu-Gln-Ser-Cys-Ala; | (SEQ ID NO:97) |
| Tyr-Asn-Glu-Gln-Ser-Cys-Ala; | (SEQ ID NO:98) |
| Thr-Ser-Glu-Gln-Cys-Ser-Ala; | (SEQ ID NO:99) |
| Thr-Asn-Glu-Gln-Cys-Ser-Ala; | (SEQ ID NO:100) |
| Tyr-Ser-Glu-Gln-Cys-Ser-Ala; | (SEQ ID NO:101) |
| Tyr-Asn-Glu-Gln-Cys-Ser-Ala; | (SEQ ID NO:102) |
| Thr-Ser-Glu-Cys-Gln-Ser-Ala; | (SEQ ID NO:103) |
| Thr-Asn-Glu-Cys-Gln-Ser-Ala; | (SEQ ID NO:104) |
| Tyr-Ser-Glu-Cys-Gln-Ser-Ala; | (SEQ ID NO:105) |
| Tyr-Asn-Glu-Cys-Gln-Ser-Ala; | (SEQ ID NO:106) |
| Thr-Ser-Cys-Glu-Gln-Ser-Ala; | (SEQ ID NO:107) |
| Thr-Asn-Cys-Glu-Gln-Ser-Ala; | (SEQ ID NO:108) |
| Tyr-Ser-Cys-Glu-Gln-Ser-Ala; | (SEQ ID NO:109) |
| Tyr-Asn-Cys-Glu-Gln-Ser-Ala; | (SEQ ID NO:110) |
| Glu-Gln-Ser-Cys-Asp; | (SEQ ID NO:111) |
| Glu Gln-Cys-Ser-Asp; | (SEQ ID NO:112) |
| Glu-Cys-Gln-Ser-Asp; and | (SEQ ID NO:113) |
| Cys Glu Gln Ser Asp. | (SEQ ID NO:114) |

Additional oligopeptides comprising the following amino acid sequences demonstrated hair growth promoting activity and are encompassed within the present invention.

| | |
|---|---|
| Ser-Ile-Glu-Gln-Ser-Xaa-Asp-Gln; | (SEQ ID NO:115) |
| Ser-Ile-Glu-Gln-Xaa-Ser-Asp-Gln; | (SEQ ID NO:116) |
| Ser-Ile-Glu-Xaa-Gln-Ser-Asp-Gln; and | (SEQ ID NO:117) |
| Ser-Ile-Xaa-Glu-Gln-Ser-Asp-Gln; | (SEQ ID NO:118) |

wherein Xaa represents a reactive substance-bound Cys or a reactive substance-bound Lys.

Table II below provides a characterization of the structure of oligopeptides having hair growth providing activity. The amino acid SIEQSCD (SEQ ID NO: 87) is the pep7 region of murine epimorphin.

TABLE II (SEQ ID NO:87)
Structure showing a hair growth promoting activity.

| Hydro-phobic/neutral | Hydro-phobic/neutral | | | Hydro-phobic/neutral | | Hydro-phobic or G or A or L |
|---|---|---|---|---|---|---|
| ↓ | ↓ | | | ↓ | | ↓ |
| S | I | [E | Q | S | C] | D |
| ① | ② | ③ | ④ | ⑤ | ⑥ | ⑦ |
| 7T | 9S | 4K | 3P | 4F | | 4A |
| 6Y | 7N | 2G | 2T | 3P | | 3G |
| 5P | 6T | 2Q | 2R | 2A | | 3E |
| 2F | 4G | R | S | C | | 3H |
| 2V | 3V | A | H | T | | 2S |
| 1G | 2F | V | E | W | | 2N |
| 1A | 2L | W | K | Y | | Y |
| | | | | | | L |

| Hydrophillic ← | | → Hydrophobic |
|---|---|---|
| Basic<br>K, R, H<br>Acidic<br>D, E | Neutral<br>N, Q, S,<br>T, Y | A, V, L, I,<br>P, F, W, M,<br>C, G |

In order to produce oligopeptides in *E. coli*, an oligopeptide library was prepared. Table III provides information about the oligopeptide library prepared. In Table III, the design value of the library is represented by the lower "theory value". The actually prepared oligopeptides are represented by the upper "appearance" value.

TABLE III (SEQ ID NO:87)

| S | —I | —E | —Q | —S | —C | —D |
|---|---|---|---|---|---|---|
| S 64<br>130 | I 49<br>110 | E 81<br>180 | Q 83<br>180 | S 80<br>180 | | D 71<br>160 |
| T 10<br>140 | S 13<br>180 | E 6.0<br>100 | P 6.0<br>70 | F 6.0<br>93 | | A 6.0<br>90 |
| Y 9.0<br>140 | N 11<br>170 | G 3.0<br>40 | P 3.0<br>30 | P 5.0<br>70 | | G 5.0<br>71 |
| P 8.0<br>110 | T 8.0<br>130 | Q 3.0<br>40 | R 3.0<br>40 | A 3.0<br>40 | | E 5.0<br>140 |
| | | | | | | G 5.0<br>78 |

Appearance (%)
To theory value (%)

In some examples an oligopeptide of the present invention is about 5 to about 104 amino acid residues in length, and in other examples about 5 to about 100 amino acid residues in length and in additional examples, an oligopeptide is about 7 to about 100 amino acid residues in length. In yet further examples, an oligopeptide is about 7 to about 104 amino acid residues in length. In additional examples, an oligopeptide is about 5 to about 40 amino acid residues in length, about 6 to about 30 amino acid residues in length, about 7 to about 20 amino acid residues in length, about 7 to about 15 amino acid residues in length, about 7 to about 12 amino acid residues in length, about 7 to about 10 amino acid residues in length, about 8 to about 20 amino acid residues in length, about 8 to about 15 amino acid residues in length, about 8 to about 12 amino acid residues in length, and about 8 to about 10 amino acid residues in length.

In some embodiments, an oligopeptide of the present invention is at least 5, at least 6, at least 7, at least 8, at least 9, at least 10, at least 11, at least 12, at least 13, at least 14, at least 15, at least 16, is at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, is at least 37, at least 38, at least 39, at least 40, at least 41, at least 42, at least 43, at least 44, at least 45, at least 46, at least 47, at least 48, at least 49 or at least about 50 amino acid residues in length. In other embodiments, an oligopeptide of the present invention is up to at least 50, up to at least 55, up to at least 60, up to at least 65, up to at least 70, up to at least 75, up to at least 80, up to at least 85, up to at least 90, up to at least 95, up to at least 100, up to at least 101, up to at least 102, up to at least 103 or up to at least 104 amino acid residues in length. It may be desirable when using larger oligopeptides to include agents that enhance or facilitate endermic absorption of oligopeptides. Such agents include, for example, agents that enhance transdermal penetration and/or delivery. Such agents are known in the art and described herein.

In some examples, the lower limit of the length of an oligopeptide of the invention is at least 5, at least 6, at least 7, at least 8, at least 9, at least 10, at least 11, at least 12, at least 13, at least 14, or at least 15 amino acid residues in length, and the upper limit is up to at least 15, up to at least 20, up to at least 25, up to at least 30, up to at least 35, up to at least 40, up to at least 45, or up to at least 50 amino acid residues in length, wherein the upper limit and lower limit are selected independently.

The type of amino acid residue in an oligopeptide of the present invention is not particularly limited, and may be any of natural type amino acid residue, non-natural type amino acid residue, or derivatives thereof. The amino acid may be L-amino acid, D-amino acid or a mixture thereof. The type of the amino acid may be any of α-amino acid, β-amino acid, γ-amino acid or δ-amino acid. α-amino acid, which is a natural type amino acid, is preferred.

The non-natural type amino acid used herein covers all of the amino acids other than 20 types of the natural type amino acids which constitute a natural protein (Gly, L-Ala, L-Val, L-Leu, L-Ile, L-Ser, L-Thr, L-Asp, L-Glu, L-Asn, L-Gln, L-Lys, L-Arg, L-Cys, L-Met, L-Phe, L-Tyr, L-Trp, L-His, L-Pro). Specific examples include (1) non-natural type amino acid wherein an atom in a natural type amino acid is substituted with another substance, (2) an optical isomer as to a side chain of natural type amino acid, (3) non-natural type amino acid obtained by introducing a substituent into a side chain of natural type amino acid, and (4) non-natural type amino acid obtained by substituting the side chain of natural type amino acid to alter hydrophobic property, reactivity, charge, size of the molecule, hydrogen bonding ability and the like.

An oligopeptide may be in free form, or may be provided as an acid addition salt or base addition salt.

Oligopeptide amino acid residues may comprise naturally occurring amino acid residues, non-naturally occurring amino acid residues, or a mixture of naturally occurring and non-naturally occurring amino acid residues. In some embodiments, an oligopeptide may be modified, such as for example, by adding a reactive substance, such as a cross-linking agent, such that the oligopeptide is capable of dimerizing or polymerizing with an oligopeptide. The present invention encompasses oligopeptide monomers, oligopeptide monomers having a reactive substance bound, and oligopeptide polymers, such as dimers, including homodimers (an oligopeptide dimerized with an identical oligopeptide) and heterodimers, (an oligopeptide dimerized with a different oligopeptide). In some embodiments, a reactive substance is bound to a Cys or a Lys within the oligopeptide and in further embodiments, a reactive substance is bound to a Cys or a Lys within the pep 7 region of an oligopeptide.

Biological activity of an oligopeptide can be measured, for example, by assaying the morphogenesis-accelerating activity against MDCKII cells derived from kidney, as described in EP 1008603A1. Briefly, MDCKII cells are added to a mixture containing a test polypeptide, collagen and appropriate culture conditions that produce a collagen gel and cells are allowed to incubate under appropriate conditions. A positive result is indicated by the formation of tubular structures in a three dimensional manner in the collagen gel.

Japanese Application publication HEI 6-25,295 also describes an assay for measuring morphogenesis activity of epithelial tissues. U.S. Pat. No. 5,726,298 describes an assay for determining epithelial growth. Briefly, pulmonary epithelium tissue isolated from fetal mice is subjected to three dimensional cultivation on nucleopore membrane and continued growth of the tubular form of the pulmonary epithelium is measured in the presence of a test molecule, such as an oligopeptide of the present invention.

Biological activity of an oligopeptide can also be measured by, for example, measuring the ability of an oligopeptide to promote hair growth or exhibit hair growth promoting activity such as by, stimulating hair generation, inducing the formation of a greater number of hair strands and/or increasing the diameter of the hair strand and/or lengthening the hair strand and/or preventing, retarding or arresting the process of hair loss, and/or by inducing new follicle in number or size or both, an assay for which is disclosed herein in Examples 7 and 8 and/or inducing hair follicle cell proliferation as measured by the in vitro assay disclosed in U.S. Pat. No. 5,616,471.

More specifically, a hair growth promoting activity can be evaluated by detecting or measuring the monoclonal antibody, or antibody fragment thereof, specific for the 220 kDa antigen of epithelial new follicle which reacts with the skin tissue, and thereby measuring the amount of 220 kDa antigen expressed on epithelial new follicles in response to administration of an oligopeptide of the present invention.

One of ordinary skill in the art can easily ascertain that the oligopeptides of the present invention have a hair growth promoting activity by test methods, such as the one described in detail in the Examples of the present specification or alterations or modifications to said test method. Other test methods include those disclosed in U.S. Pat. No. 5,616,471.

Examples of such test methods disclosed herein include but are not limited to the below.

(1) C3H and C57BL/6 mice are known to have sustained telogen for about 50 days from the 45th day after the birth to around the 95th day. Their hair cycle is easily judged based on the skin color changes, i.e., from pink in telogen to gray or black in anagen. “Anagen” refers to the active stage of a hair follicle and “telogen” refers to the resting phase of a hair follicle. A hair growth promoting activity can be evaluated by using this mice and evaluating whether or not the administration of the test substance promotes the transition from telogen to anagen.

(2) A hair growth promoting activity can be evaluated by using a monoclonal antibody, or a fragment thereof (for example, a monoclonal antibody produced by the hybridoma having an accession number FERM P-18578) which specifically recognizes an antigen present in epithelial new follicles (for example, about 220 kDa antigen). Specifically, skin tissue from an organism is cultured in the presence of a test substance, such as an oligopeptide encompassed within the present invention, and the skin tissue is collected, and reacted with a monoclonal antibody produced by the hybridoma having an accession number FERM P-18578, or a fragment thereof. A hair growth promoting activity can be evaluated by detecting or measuring the monoclonal antibody or a fragment thereof which reacted with the skin tissue, and thereby measuring the amount of the antigen expressed on epithelial new follicles. An increase in the amount of epithelial new follicles is correlated with hair growth promoting activity in humans.

Conditions suitable for dimerization as used herein refer to conditions whereby an oligopeptide of the invention binds another oligopeptide. In some embodiments, an oligopeptide binds covalently with another oligopeptide. Dimerization conditions are known in the art and include conditions whereby a sulfhydryl group of a cysteine residue in an oligopeptide forms a covalent bond with a sulfhydryl group of a cysteine residue or amino group of a lysine residue of an oligopeptide.

A reactive substance-bound Cys or reactive substance-bound Lys refers to a Cys or Lys amino acid residue that has bound to it a substance, such as for example, a cross-linking agent, that is capable of reacting and binding with a functional group such a —SH group or -NH2 group. In some embodiments, the reactive substance is a cross-linking agent. In other embodiments, the reactive substance is a bifunctional cross-linking agent. In some embodiments of the invention, an oligopeptide exhibiting morphogenic activity, such as for example, exhibiting hair growth promoting activity is in the form of a monomer and, in particular, a monomer that is capable of dimerization under suitable conditions. In other embodiments of the invention, an oligopeptide is in the form of reactive-substance bound monomer that is capable of dimerization under suitable conditions. In additional embodiments of the invention, an oligopeptide is in the form of a polymer, such as, dimers such as homodimers or heterodimers, and trimers.

Accordingly, the present invention provides oligopeptide polymers having morphogenic promoting activity, such as, hair growth promoting activity, comprising cross-linked oligopeptides wherein at least one oligopeptide of said oligopeptide polymer comprises between about 5 and about 104 amino acid residues in length and comprises the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Ala, Tyr, Thr, Pro, Phe, Val, Gly, Leu, Ile or Met, or is deleted from said oligopeptide;

X2 is an amino acid residue of Ile, Gly, Asn, Thr, Val, Ser, Phe, Leu, Ala, Pro, Cys, or Met, or is deleted from said oligopeptide;

X3 is an amino acid residue of Glu, Lys, Gln, Arg, Ala, Val, Trp, Cys, or Asp;

X4 is an amino acid residue of Gln, Pro, Glu, Thr, Arg, Ser, His, Cys, or Lys;

X5 is an amino acid residue of Ser, Trp, Phe, Thr, Cys, Tyr, Pro, Ala, Gly, Val, Leu, Ile, or Met;

X6 is an amino acid residue Cys; a reactive substance-bound Cys or a reactive substance-bound Lys; and X7 is an amino acid residue of Asp, Glu, His, Ser, Ala, Gly, Asn, Tyr, Arg, or Leu, or is deleted from said oligopeptide, with the proviso that the polymer is not a homopolymer of SEQ ID NO:1 or SEQ ID NO:2.

In some embodiments, an oligopeptide polymer having morphogenic promoting activity comprises at least one oligopeptide comprising between about 5 to about 104 amino acid residues having the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Tyr, Thr, or Pro, or is deleted from said oligopeptide;

X2 is an amino acid residue of Ile, Asn, Thr, or Ser, or is deleted from said oligopeptide;

X3 is an amino acid residue of Glu, Ala, Trp, or Asp;

X4 is an amino acid residue of Gln;

X5 is an amino acid residue of Ser, Cys, or Tyr;

X6 is an amino acid residue of Cys; a reactive substance-bound Cys or a reactive substance-bound Lys; and X7 is an amino acid residue of Asp, Ala, Gly, or Leu, or is deleted from said oligopeptide, with the proviso that the oligopeptide polymer is not a homopolymer of SEQ ID NO:2.

The present invention also provides oligopeptide polymers having morphogenic promoting activity, such as, hair growth promoting activity comprising cross-linked oligopeptides wherein at least one oligopeptide of said oligopeptide polymer comprises between about 7 and about 100 amino acid residues in length and comprises the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Ala, Tyr, Thr, Pro, Phe, Val, Gly, Ala, Leu, Ile or Met, or is deleted from said oligopeptide;

X2 is an amino acid residue of Ile, Gly, Asn, Thr, Val, Ser, Phe, Leu, Ala, Pro, Cys, or Met, or is deleted from said oligopeptide;

X3 is an amino acid residue of Glu, Lys, Gln, Arg, Ala, Val, Trp, Cys, or Asp;

X4 is an amino acid residue of Gln, Pro, Glu, Thr, Arg, Ser, His, Cys, or Lys;

X5 is an amino acid residue of Ser, Trp, Phe, Thr, Cys, Tyr, Pro, Ala, Gly, Val, Leu, Ile, or Met;

X6 is an amino acid residue of Cys; and

X7 is an amino acid residue of Asp, Glu, His, Ser, Ala, Gly, Asn, Tyr, Arg, or Leu, or is deleted from said oligopeptide.

The present invention also provides oligopeptide polymers having morphogenic promoting activity, such as, hair growth promoting activity comprising cross-linked oligopeptides wherein at least one oligopeptide of said oligopeptide polymer comprises between about 7 and about 100 amino acid residues in length and comprises the following amino acid sequence:

X1-X2-X3-X4-X5-X6-X7;

X1-X2-X3-X4-X6-X5-X7;

X1-X2-X3-X6-X4-X5-X7; or

X1-X2-X6-X3-X4-X5-X7;

wherein X1 is an amino acid residue of Ser, Tyr, Thr, or Pro, or is deleted from said oligopeptide;

X2 is an amino acid residue of Ile, Asn, Thr, or Ser, or is deleted from said oligopeptide;

X3 is an amino acid residue of Glu, Ala, Trp, or Asp;

X4 is an amino acid residue of Gln;

X5 is an amino acid residue of Ser, Cys, or Tyr;

X6 is an amino acid residue of Cys; and

X7 is an amino acid residue of Asp, Ala, Gly, or Leu, or is deleted from said oligopeptide.

In additional examples, the oligopeptide polymer comprises an oligopeptide of the present invention that comprises any one of oligopeptides SEQ ID NO:3 to SEQ ID NO:135 alone, that is as a polymer of a single oligopeptide (that is, a homopolymer) or as a polymer of a mixture of oligopeptides of the present invention (heteropolymer). In some examples of the present invention, an oligopeptide polymer is a homodimer; heterodimer; homotrimer; or heterotrimer.

The present invention encompasses modified oligopeptides. The term "modified" in the present invention includes chemical modification and biological modification. Examples of the modification include introduction of a functional group such as alkylation, esterification, halogenation, and amination, or conversion of a functional group such as oxidation, reduction, addition, and elimination, or introduction of a sugar compound (a monosaccharide, disaccharide, oligosaccharide, or polysaccharide) or a lipid compound, phosphorylation, biotinylation. However, the modifications are not limited to these examples. Accordingly, the present invention provides modified oligopeptides and methods of promoting hair growth in a mammalian subject comprising administering a composition comprising a modified oligopeptide to a mammalian subject in need of hair growth in an amount effective to promote hair growth in said mammal.

An example of a modified oligopeptide includes a biotinylated oligopeptide, and a more preferred example includes an oligopeptide of which N-terminal is bound by biotin with or without a spacer. In the above modified oligopeptide, an appropriate chemical modification may be added to the biotin as long as the desirable physiological activity is maintained. A method for producing the biotinylated oligopeptide is specifically shown in the Examples of the present specification. In order to introduce biotin to the N-terminal by means of a spacer having an appropriate length, for example, NHS-Biotin or NHS-LC-Biotin (available from Pierce) can be used.

Another preferred example of a modified oligopeptide includes an oligopeptide dimerized by sulfhydryl group of cysteine residue therein. The dimerization reaction spontaneously proceeds under air atmosphere to form a dimer. However, not all of the oligopeptides form a dimer. The dimerized oligopeptide may be a homodimer oligopeptide obtained by cross-linking the same oligopeptides, or a heterodimer oligopeptide obtained by cross-linking different 2 types of oligopeptides. A composition comprising an oligopeptide or oligopeptides of the present invention for use in promoting morphogenesis activity, such as, hair growth, may in the form of a mixture of the same or different monomers and in particular monomers that are capable of dimerizing under suitable conditions, monomer(s) having a reactive substance bound thereto and polymers, such as dimers.

A polymer of the present invention, such as a homodimer or heterodimer, can be obtained by cross-linking any oligopeptides of the present invention mentioned above, including modified oligopeptides, by a cross-linking agent.

The cross-linking agents used in the present invention preferably include a bifunctional cross-linking agent which can activate sulfhydryl group of cysteine residue in an oligopeptide and form a covalent bond with sulfhydryl group of cysteine residue in another oligopeptide.

Examples of the bifunctional cross-linking agent which can be used in the present invention include bismaleimide compounds, such as compounds wherein N atom of a maleimide group is bound to both ends of a lower alkyl group (for example, C1–C10, preferably C1–C8 alkyl group) optionally having a substituent such as a hydroxyl group. Examples of bismaleimide compounds include 1,4-bismaleimidyl-2,3-dihydroxybutane, 1,6-bismaleimidehexane, bismaleimidethane, and 1,4-bismaleimidebutane.

Further, monomer oligopeptides wherein a cross-linking agent is bound to a cysteine residue in any of the aforementioned oligopeptide (including modified oligopeptides), and methods of using such monomers to promote hair growth in a mammalian subject also fall within the scope of the present invention.

Furthermore, in addition to dimer oligopeptides, polymer oligopeptides such as trimers or more fall within the scope of the present invention. For example, the present invention encompasses polymer oligopeptides, such as trimers or more which are obtained by using a cross-linking agent which can cross-link 3 or more peptides.

The above oligopeptides (including modified oligopeptides) may be in free form, or may be provided as acid addition salts or base addition salts. Examples of the acid addition salts include mineral acid salts such as hydrochloride, sulfate, nitrate, and phosphate; organic acid salts such as para-toluenesulfonate, methanesulfonate, citrate, oxalate, maleate, and tartrate. Examples of the base addition salts include metal salts such as sodium salt, a potassium salt, a calcium salt, and a magnesium salt; an ammonium salt; organic ammonium salts such as a methyl ammonium salt, and a trimethyl ammonium salt. The oligopeptide may form a salt with amino acids such as glycine, or may form a counter ion in the molecule.

Further, these oligopeptides or salts thereof may exist in a form of a hydrate or a solvate. The above oligopeptides have plural asymmetric carbon atoms. Although the stereochemistry of each asymmetric carbon atoms is not limited, it is preferable that the amino acid reside is L-amino acid. Stereoisomers such as optical isomers or diastereomers based on the asymmetric carbon atoms, any mixtures of the stereoisomers, and racemates fall within the scope of the present invention.

The oligopeptide of the present invention can be synthesized by a conventional chemical technique for peptide synthesis, such as solid phase or liquid phase method. There are various kinds of references about protective groups for amino groups or the like and condensation agents for a condensation reaction in the field of peptide synthesis, and accordingly, these references can be referred to for the synthesis. In the solid phase method, commercially available various peptide synthesizers can be utilized. The synthesis can be efficiently carried out by performing protection and deprotection of functional groups as necessary. As for a method for introducing and removing a protective group, for example, Protective Groups in Organic Synthesis, T. W. Greene, John Wiley & Sons, Inc. 1981 and the like can be referred to.

By applying biological methods known to those of skilled in the art such as a gene expression procedure, a desired oligopeptide can be obtained by constructing a recombinant vector containing a DNA sequence encoding the above oligopeptide, preparing a microorganism (transformant) transformed by the vector, and separating optionally and purifying the oligopeptide from culture of the transformant. The method for producing the oligopeptides is not limited to these chemical and biological methods. Methods for producing modified oligopeptides including chemical modification and biological modification are well known to one of ordinary skill in the art, and any methods can be used.

The present invention also provides host cells comprising (i.e., transformed with) the nucleic acid encoding the oligopeptides described herein. Both prokaryotic and eukaryotic host cells can be used as long as sequences requisite for maintenance in that host, such as appropriate replication origin(s), are present. For convenience, selectable markers are also provided. Host systems are known in the art. Prokaryotic host cells include bacterial cells, for example, *E. coli, B. subtilis*, and mycobacteria. Among eukaryotic host cells are yeast, insect, avian, plant, *C. elegans* (or nematode) and mammalian host. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are cultured Chinese hamster ovary (CHO) cells and African green monkey cells. *Xenopus laevis* oocytes, or other cells of amphibian origin, may also be used.

Uses of the Oligopeptides of the Present Invention

Oligopeptides of the present invention are useful as an active ingredient of a medicament or pharmaceutical composition useful for the treatment and/or amelioration of symptoms of diseases or disorders of abnormal morphogenesis. The oligopeptides of the present invention can be used to induce morphogenesis, induce revascularization effect, induce regeneration effect, induce cardiovascular regeneration, and induce endothelial cell growth. The oligopeptides of the present invention can be used for the treatment of and/or amelioration of symptoms of, for example, burns or wounds or to promote hair growth or prevent hair loss. In some examples, the compositions are useful for hair growth promotion or prevention of hair loss. Accordingly, the present invention provides a composition comprising an oligopeptide of the present invention and a pharmaceutically acceptable excipient. In some examples, a composition useful for promoting hair growth further comprises an agent that enhances endermic absorption, such as a transdermal penetration enhancer and/or a transdermal delivery agent. Such agents are known in the art and described herein. The term "medicament" or "pharmaceutical composition" is used interchangeable herein. A "pharmaceutical composition" as used herein is used in the broadest sense and encompasses compositions comprising a morphogenesis promoting agent and in some examples, a hair growth promoting agent. Morphogenesis agents are used for the amelioration of the symptoms of as well as the therapeutic treatment of diseases or disorders of a mammal, including a human. Hair growth compositions are sometimes classified as a quasi-drug or cosmetic, as well as a medicament or pharmaceutical composition. The administration subject and pharmacological effect of the medicaments of the present invention, and the diseases and/or disorders to be treated by the medicament of the present invention are specifically mentioned below. "Amelioration" as used herein means the prevention, reduction or palliation of a state. Oligopeptides of the present invention and compositions comprising an oligopeptide may be used to provide revascularization effect, regeneration promoting effect, cardiovascular regeneration effect, an inductive effect on vascular endothelial cell, and the like, and are useful for the therapy and amelioration of the symptoms of prevention of chronic obstructive arteriosclerosis, Buerger's disease, sever angina pectoris, arteriosclerosis and the like. (*Exp. Cell. Res.,* 1996, Jan. 10, 222(1):189–98). Oligopeptides of the present invention may be involved in morphogenesis of pancreatic endothelium, and compositions comprising an oligopeptide may be useful for the therapy and amelioration of the symptoms of diabetes and the like (*J. Cell. Biol.,* 2001, Mar. 5; 152(5):911–22). The oligopeptides of the present invention may be involved in formation (regeneration) of liver, and compositions comprising an oligopeptide may be useful for the therapy and amelioration of the symptoms of liver metabolism failure (*Biochem. Biophys. Res. Commun.,* 1998, Sep. 18; 250(2):486–90). Oligopeptides of the present invention may be involved in formation of bone and tooth, and therefore compositions comprising an oligopeptide may be useful for the therapy and amelioration of the symptoms of periodontics, fracture, bone tumor, bone deficiency, and osteoporosis (*Arch. Oral. Biol.,* 1995, Feb; 40(2):161–4). Oligopeptides of the present invention may be involved in lung branching morphogenesis and pulmonary fibrosis, and compositions comprising an oligopeptide may be useful for the therapy and amelioration of the symptoms of lung diseases (*Biochem. Biophys. Res. Commun.,* 1997, May 19; 234(2):522 and *Am. J. Respir. Cell. Mol. Biol.,* 2000, Aug; 23(2):168–74). The oligopeptides of the present invention may be involved in crypt-villus morphogenesis, and compositions comprising an oligopeptide may be useful for the therapy and amelioration of the symptoms of intestine diseases (*Am. J. Physiol.,* 1998, Jul; 275(1 Pt1):G114–24). Oligopeptides of the present invention may be involved in maintenance of muscle structure, and compositions comprising an oligopeptide may be useful for the therapy and amelioration of the symptoms of muscular dystrophy and the like (*Histochem. J.,* 1998, Dec; 30(12):903–8). The oligopeptides of the present invention may be involved in morphogenesis of gallbladder epithelium, and compositions comprising an oligopeptide may be useful for the therapy and amelioration of the symptoms of gallbladder diseases (*Cell. Tissue. Res.,* 2000, May; 300(2):331–44). The oligopeptides of the present invention may be involved in mammary luminal morphogenesis, and compositions comprising an oligopeptide may be useful for the therapy and amelioration of the symptoms of mammary diseases (*J. Cell. Biol.,* 2001, May 14; 153(4):785–94). Most preferably among these, the oligopeptides of the present invention can be used as a hair growth promoting agent.

A composition of the present invention comprising an oligopeptide is administered to a subject in amounts effective to promote morphogenesis. In some examples, the compositions of the present invention comprising an oligopeptide are administered to a subject in amounts effective to promote hair growth. The subject may be experiencing hair loss and/or at risk for hair loss.

Accordingly, the present invention provides a method for promoting hair growth in a mammalian subject experiencing hair loss or at risk for hair loss comprising administering a composition comprising an oligopeptide of the present invention in an amount effective to promote hair growth in said mammalian subject.

As a medicament or pharmaceutical composition of the invention, one or more oligopeptides selected from among the oligopeptides disclosed herein, or their physiologically acceptable salt, may be used. The oligopeptides of the present invention may be in the form of a monomer and, in particular, a monomer that is capable of dimerization under conditions suitable for dimerization, a monomer having a reactive substance bound and as a polymer, such as a dimer, including a homodimer and heterodimer or trimer, including a homotrimer and a heterotrimer. Generally, however, it is preferable to prepare and administer a pharmaceutical composition comprising one or more of the above oligopeptides as an active ingredient by using one or more pharmaceutically acceptable pharmaceutical additives. A hair growth promoting agent containing one or more of the aforementioned oligopeptides as an active ingredient can be applied in a form of external preparations such as a cream, a spray, a coating solution, and a patch. The agent can be administered to a target site directly in a form of an injection. It is possible to provide the agent in any form suitable for the purpose of use as a hair growth promoting agent.

For example, the above oligopeptides as an active ingredient may be added to a shampoo or a rinse, or the above oligopeptide can be encapsulated into a liposome to manufacture a preparation. The composition in the aforementioned forms also falls within the scope of the present invention. In order to achieve an effective transdermal absorption of the oligopeptides of the invention through the keratin layer of skin, it is preferable to add an appropriate detergent, lipid-soluble substance of the like in a cream.

Agents that enhance transdermal penetration and transdermal delivery are described in, for example, U.S. Patent Publication, 2002 0048558A1; U.S. Pat. No. 6,376,557; U.S. Pat. No. 6,333,057; U.S. Pat. No. 6,358,541; and U.S. Pat. No. 6,299,900 and include for example, laurocapram and laurocapram derivatives, such as 1-alkylazacycloheptan-2-specified in U.S. Pat. No. 5,196,410, and oleic acid and its ester derivatives, such as methyl, ethyl, propyl, isopropyl, butyl, vinyl and glycerylmonooleate, and those given in U.S. Pat. No. 5,082,866, particularly dodecyl (N,N- dimethylamino) acetate and dodecyl (N,N-dimethylamino) propionate and in U.S. Pat. No. 4,861,764, particularly 2-n-nonyl-1-3-dioxolane. Other known dermal penetration enhancers include adapalene, tretinoin, retinalaldehyde, tazarotene, salicylic acid, azelaic acid and glycolic acid. Additional dermal penetrating agents include ethoxydiglycol, ethanol, Tween™ 80, and lecithin organogel.

For topical administration in mammals, preferably humans, the subject compositions may be provided as a wide variety of product types including, but are not limited to, lotions, creams, gels, sticks, sprays, ointments and pastes. These product types may comprise several types of formulations including, but not limited to solutions, emulsions, gels, solids, and liposomes.

Compositions useful for topical administration of the compositions of the present invention formulated as solutions typically include a pharmaceutically-acceptable aqueous or organic solvent. The terms "pharmaceutically-acceptable organic solvent" refer to a solvent which is capable of having an oligopeptide of the present invention dispersed or dissolved therein, and of possessing acceptable safety properties (e.g., irritation and sensitization characteristics). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanediol, and mixture thereof.

An oligopeptide of the present invention can be dissolved in PBS at approximately 1 mg/ml. An oligopeptide dimerized with a cross-linking agent can be dissolved at approximately 0.9 mg/ml. The solubility can be determined by measuring absorbance of peptide solution. In the case of monomer, the solubility can be determined by $(A_{215}-A_{225})\times 144$ (μg/ml) (Waddell, 1956). In the case of dimer, the value obtained by this calculation may be divided by 1.3.

If the topical compositions useful in the subject invention are formulated as an aerosol and applied to the skin as a spray-on, a propellant is added to a solution composition. Examples of propellants useful herein include, but are not limited to, the chlorinated, fluorinated or chloro-fluorinated lower molecular weight hydrocarbons.

Topical compositions useful in the subject invention may be formulated as a solution comprising an emollient. As used herein, "emollients" refer to materials used for the prevention or relief of dryness, as well as for the protection of the skin. A wide variety of suitable emollients are known and may be used herein.

Another type of product that may be formulated from a composition comprising an oligopeptide is a cream and a lotion. Lotions and creams can be formulated as emulsions as well as solutions.

Yet another type of product that may be formulated from a composition of the present invention is an ointment. An ointment may comprise a simple base of animal or vegetable oils or semi-solid hydrocarbons (oleaginous). Ointments may also comprise absorption ointment bases which absorb water to form emulsions. Ointments carriers may also be water soluble.

Another type of formulation is an emulsion. Emulsifiers may be nonionic, anionic or cationic and examples of emulsifiers are described in, for example, U.S. Pat. Nos. 3,755,560 and 4,421,769.

Single emulsions for topical preparations, such as lotions and creams, of the oil-in-water type and water-in-oil type are well-known in the art. Multiphase emulsion compositions, such as the water-in-oil-in-water type, are also known, as disclosed, for example, in U.S. Pat. No. 4,254,105. Triple emulsions are also useful for topical administration of the present invention and comprise an oil-in-water-in-silicone fluid emulsion as disclosed, for example in U.S. Pat. No. 4,960,764.

Another emulsion useful in the topical compositions is a micro-emulsion system. For example, such system comprises from about 9% to about 15% squalane, from about 25% to about 40% silicone oil; from about 8% to about 20% of a fatty alcohol; from about 15% to about 30% of polyoxyethylene sorbitan mono-fatty acid (commercially available under the trade name TWEENS) or other nonionics; and from about 7% to about 20% water.

Liposomal formulations are also useful for the compositions comprising an oligopeptide of the present invention. Such compositions can be prepared by combining a composition comprising an oligopeptide of the present invention with a phospholipid, such as dipalmitoylphosphatidyl choline, cholesterol and water according to known methods. Epidermal lipids of suitable composition for forming liposomes may be substituted for the phospholiipid. The liposome preparation is then incorporated into one of the above topical formulations (for example, a gel or an oil-in-water emulsion) in order to produce the liposome formulation. Other compositions and pharmaceutical uses of topically applied liposomes are described in, for example, Mezei (1985) Topics in Pharmaceutical Sciences, Breimer et al., eds., Elsevier Science, New York, N.Y., pp. 345–358.

The dose of a composition comprising an oligopeptide of the present invention can be selected suitably depending on the purpose of application, the form of the agent, a kind of the active ingredient and the like. For example, it is possible to determine a dose by referring to the dose specifically shown in the Examples of the present specification. For example, the dose of the active ingredient of a composition, that is, of an oligopeptide of the present invention, per day per adult is generally within the range of about 1 μg/kg/day to about 10 mg/kg/day, in some examples, about 10 μg/kg/day to about 1 mg/kg/day, in other examples, about 100 μg/kg/day to about 500 μg/kg/day, in other examples, about 200 μg/kg/day to about 400 μg/kg/day. In some examples, the lower range of a dose is at least 1 μg/kg/day, 10 μg/kg/day, 20 μg/kg/day, 30 μg/kg/day, 40 μg/kg/day, 50 μg/kg/day, 60 μg/kg/day, 70 μg/kg/day, 80 μg/kg/day, 90 μg/kg/day, 100 μg/kg/day, 150 μg/kg/day, 200 μg/kg/day, 250 μg/kg/day, 300 μg/kg/day, 350 μg/kg/day, 400 μg/kg/day, 450 μg/kg/day, and 500 μg/kg/day. In other examples, the upper range is up to 600 μg/kg/day, 700 μg/kg/day, 800 μg/kg/day, 900 μg/kg/day, 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, and 10 mg/kg/day, with the lower range and upper range being selected independently.

Antibodies

The present invention encompasses antibodies that specifically bind an oligopeptide of the present invention wherein said antibodies may be useful for the detection, quantitative determination, separation or purification of the oligopeptide by means known to those of skill in the art. Polyclonal antibodies and monoclonal antibodies, and fragments thereof, that specifically bind an oligopeptide of the present invention are encompassed within the present invention and can be made by conventional methods.

The present invention also encompasses monoclonal antibodies that specifically recognize, that is, that specifically bind, an antigen of about 220 kDa present in epithelial new follicles which is specifically expressed during the growth period of an imago or the developing period of a fetus. Such a monoclonal antibody can be used to assay for hair growth promoting activity of an oligopeptide of the present invention as described herein in the examples.

An example of such monoclonal antibodies is monoclonal antibody mAb27 which is described herein in the Examples. The hybridoma which produced monoclonal antibody mAb27 was deposited with Patent and Bio-Resource Center of National Institute of Advanced Industrial Science and Technology (Chuo-6, 1-1, Higashi 1-chome, Tsukuba-shi, Ibaraki-ken, Japan) on Nov. 2, 2001 under the deposit number of FERM P-18578.

The term "antibody" used in the present specification encompasses polyclonal antibodies as well as monoclonal antibodies and also encompasses fragments of the antibody. According to the present invention, there is provided a fragment of a monoclonal antibody which specifically recognizes the antigen of about 220 kDa present in the epithelial new follicles. The fragment of the antibody is preferably a functional fragment, and its examples are $F(ab')_2$ and Fab'.

$F(ab')_2$ and Fab' are prepared by the treatment of immunoglobulin with protease such as pepsin or papain and are antibody fragments produced by the digestion thereof at the sites which are before and after a disulfide bond existing between two H chains in a hinge region. The term "fragment of antibody" used in the present specification shall also include protein which contains an antigen-bonded site derived from a gene encoding said antibody.

For example, when IgG1 is treated with papain, cleavage takes place at the upper stream of the disulfide bond existing between the two H chains of the hinge region to give two homologous antibody fragments where L chain comprising VL (L chain variable region) and CL (L chain constant region) and H chain fragment comprising VH (H chain variable region) and CHγ1 (γ1 region in H chain constant region) are bonded by a disulfide bond at the C terminal region. Each of those two homologous antibody fragments is called Fab'. Further, when IgG is treated with pepsin, cleavage takes place at the downstream of the disulfide bond existing between the two H chains in the hinge region to give antibody fragments which are somewhat bigger than that where the above two Fab' are connected in a hinge, region. This antibody fragment is called $F(ab')_2$.

An antibody of the present invention may be used as an immobilized antibody, that is, immobilized on an insoluble carrier such as solid carrier, or may be used as a labeled antibody labeled with a labeling substance. All of such immobilized antibody and labeled antibody are within the scope of the present invention.

An immobilized antibody is an antibody in a state of being carried on an insoluble carrier by physical adsorption, chemical bond or the like. Such an immobilized antibody may be used for detection, quantitative determination, separation or purification of antigen (i.e., an oligopeptide of the present invention or an antigen of about 200 kDa present in epithelial new follicles) contained in a sample (such as hair, epithelial new follicles or an extract thereof). Examples of the insoluble carrier which can be used for immobilization of the antibody include (1) a container having an inner volume such as plate, test tube or tube, or beads, ball, filter, membrane and the like, each of which are made of water-insoluble substance such as plastics including polystyrene resin, polycarbonate resin, silicone resin or Nylon resin, or glass and; (2) an insoluble carrier used for affinity chromatography, such as cellulose based carrier, agarose based carrier, polyacrylamide based carrier, dextran based carrier, polystyrene based carrier, polyvinyl alcohol based carrier, polyamino acid based carrier or porous silica based carrier.

A labeled antibody means an antibody labeled with a labeling substance, and such a labeled antibody may be used for detection or quantitative determination of antigen (i.e., an antigen of about 220 kDa present in epithelial new follicles) contained in a sample (such as hair, follicles or an extract thereof). There is no particular limitation for the labeling substance used in the present invention, so far as its existence can be detected by bonding to an antibody by means of physical bonding, chemical bonding or the like. Examples of the labeling substance are enzyme, fluorescent substance, chemiluminescent substance, biotin, avidin or radioactive isotope. Specific examples include enzyme such as peroxidase, alkaline phosphatase, β-D-galactosidase, glucose oxidase, glucose-6-phosphate dehydrogenase, alcohol dehydrogenase, malic acid dehydrogenase, penicillinase, catalase, apoglucose oxidase, urease, luciferase or acetylcholine esterase; fluorescent substance such as fluorescein isothiocyanate, phycobilic protein, rare earth metal chelate, dansyl chloride or tetramethylol rhodamine isothiocyanate; radioisotope such as $^{3}H$, $^{14}C$, $^{125}I$ or $^{131}I$; biotin; avidin; and chemiluminescent substance. With regard to a method for bonding a labeling substance to an antibody, known methods such as a glutaraldehyde method, a maleimide method, a pyridyl disulfide method and a periodic acid method may be used.

Here, each of the radioisotope and fluorescent substance is able to generate a detectable signal by itself, while each of enzyme, chemiluminescent substance, biotin and avidin is unable to generate a detectable signal by itself and, therefore, a detectable signal is generated as a result of reaction with one or more other substance(s). For example, in the case of an enzyme, at least a substrate is necessary and, depending upon a method for measuring the enzymatic activity (colorimetric method, fluorescent method, bioluminescent method or chemiluminescent method), various substrates are used. In the case of biotin, it is usual that at least avidin or enzyme-bound avidin is react therewith. If necessary, various coloring substances may be used depending upon the said substrate.

Hybridoma Producing a Monoclonal Antibody

The present invention also provides a hybridoma which produces a monoclonal antibody that specifically recognizes an antigen of about 220 kDa present in epithelial new follicles as described herein. The monoclonal antibody of the present invention may be produced by using said hybridoma.

A process for the preparation of a hybridoma producing a monoclonal antibody of the present invention which specifically recognizes an antigen of about 220 kDa present in the epithelial new follicles, is described below.

First, a mammal is immunized using an immunogen such as protein extracted from hair collected from the skin of the growth period and/or follicles of whiskers of the growth period, whereby antibody-producing cells are prepared in the body of the animal. Although there is no particular limitation for the type of the mammal, the examples generally include mouse, rat, cattle, rabbit, goat and sheep, preferably rodents such as mouse, rat and rabbit, and more preferably, mouse or rat. Examples of the mouse are mouse of an A/J strain, a BALB/C strain, a DBA/2 strain, a C57BL/6 strain, a C3H/He strain, an SJL strain, an NZB strain or a CBA/JNCrj strain. Mouse of a BALB/C strain is preferred since the cell strain derived from myeloma of the same strain is established at the time of the preparation of hybridoma.

In the present invention, protein extracted from hair collected from the skin of the growth period and/or follicles of whiskers of the growth period may be used as the immunogen. Any material may be used as an immunogen, so far as it contains an antigen of about 220 kDa present in the epithelial new follicles which is recognized by the monoclonal antibody of the present invention.

Before immunization, the immunogen may be mixed with an adjuvant for enhancing the immune response. Examples of the adjuvant include water-in-oil type emulsion (such as incomplete Freund adjuvant), water-in-oil-in-water type emulsion, oil-in-water type emulsion, liposome, aluminum hydroxide gel, silica adjuvant, powdery bentonite and tapioca adjuvant, as well as cell body and cell wall of BCG, *Propionibacterium acnes*, etc. and somatic component such as trehalose dicholate (TDM); lipopolysaccharide (LPS) which is an endotoxin of Gram negative bacteria and lipid A fraction; β-glucan (polysaccharide); muramyl dipeptide (MDP); bestatin; synthetic compound such as levamisole; protein or peptidic substance derived from biocomponents such as thymus hormone, liquid factor of thymus hormone and taftsin; and a mixture thereof (such as complete Freund adjuvant). Such an adjuvant is effective for augmentation or suppression of immune response depending upon administration route, dose, administration period, and the like. In addition, depending upon the type of the adjuvant, difference is found in the production of antibody in blood to antigen, induction of cellular immunity, class of immunoglobulin, and the like. Therefore, it is preferred to suitably choose the adjuvant depending upon the aimed immune response. The method for the treatment with adjuvant is known in the art.

Immunization of a mammal is carried out according to methods known by those of skill in the art. For example, an antigen is injected into a mammal either subcutaneously, intracutaneously, intravenously or intraperitoneally. Since immune responses vary depending upon the type and strain of the mammal to be immunized, an immunizing schedule is appropriately designed according to the animal to be used. Administration of antigen is repeatedly carried out for several times after the first immunization. Additional immunizations may be carried out, for example, after four weeks, six weeks and half a year from the first immunization.

After immunization, blood is collected from the mammal and the obtained blood is assayed for the presence of a hair follicle-binding activity to confirm the production of antibody against the follicles in the body of the mammal. The methods for the assay include known methods such as enzyme-linked immunosorbent assay (ELISA), radioimmunoassay (RIA) and fluorescent antibody method After confirming the production of follicle-binding antibody, a boost (additional injection of immunogen) can be carried out so that the immunocyte capable of producing a specific antibody is made into a state suitable for cell fusion. Although there is no particular limitation for the amount of the immunogen to be administered in the boost, it is preferred to be about 4- to 5-fold of the initially immunized amount. Usually, a boost may be carried out using an emulsion of immunogen and incomplete Freund adjuvant. Route for the administration may be appropriately selected from subcutaneous, intracutaneous, intravenous, intraperitoneal administrations or the like.

After the final immunization, spleen cells are excised from the immunized mammal and subjected to a cell fusion with a cell strain derived from myeloma. In the cell fusion, it is preferred to use a cell strain having a high proliferation potency and it is preferred that a cell strain derived from myeloma has a compatibility to the mammal from which the spleen cells to be fused is derived. Examples of the cell strain derived from myeloma of mouse include P3U1, P3X63-Ag8.653, Sp2/O-Ag14, FO.1, S194/5, XX0BU.1, P3/NS1/1-Ag4-1 and the like.

Cell fusion may be carried out by methods known to those of skill in the art. Examples of the cell fusion method include a polyethylene glycol method, a method using Sendai virus, and a method using electric current. For general methods, see Antibodies, A Laboratory Manual by Ed Harlow David Lane, 1988, Cold Spring Harbor Laboratory.

The resulting fused cells may be proliferated by conditions known in the art. Desired fused cells are selected depending upon the binding ability of the produced antibody.

The ability of an antibody produced from the fused cells to bind a desired antigen is assayed according to methods known in the art. In the present invention, a cell strain of interest is cloned utilizing as a selection the ability of the fused cells to produce antibody which has a high binding ability and is specific to an antigen of epithelial new follicles. Binding ability of the antibody may be assayed by a method such as ELISA, RIA and fluorescent antibody method in the same way as in those mentioned already for the confirmation of production of antibody. Because of its simplicity and high sensitivity, ELISA is preferred.

Cloning of fused cells may be carried out by methods known in the art. The methods for cloning include a limiting dilution method, a soft agar method, and the like. Because of easily operation and high reproducibility, a limiting dilution method is preferred. In order to efficiently select useful cells from many fused cells obtained by cell fusion, it is preferred that selection of the cells is carried out from the initial stage of the cloning. In such a way, it is possible to finally select a fused cell strain which produces an antibody having a desired binding ability.

By culturing the monoclonal antibody producing cell strain selected as mentioned above in a large scale, a monoclonal antibody specific to follicles can be produced in large amount. The methods for a large-scale culturing of the monoclonal antibody-producing cell strain include in vivo and in vitro culturing. An example of the large-scale in vivo culturing is a method where fused cells are intraperitoneally injected into mammal to proliferate so that an antibody is produced in abdominal dropsy, that is abdominal ascites. In the in vitro culturing, fused cells are cultured in a medium and an antibody is produced in the medium.

The monoclonal antibody of the present invention can be purified from the abdominal dropsy obtained by a large-scale culturing or from supernatant fluid of the culture medium by methods known in the art. For the purification, an appropriate combination of DEAE anion-exchange chromatography, affinity chromatography, ammonium sulfate fractionation, PEG fractionation, ethanol fractionation, and the like may be used. The antibody of the present invention may be purified preferably to a purity of about 90%, more preferably to a purity of about 95% or, still more preferably, to a purity of about 98%.

Methods for Evaluation of Hair Growth Promoting Activity

The present invention further relates to a method for the evaluation of hair growth promoting activity characterized in that an immunoassay is carried out using a monoclonal antibody that specifically binds an antigen of about 220 kDa present in the epithelial new follicles, or a fragment of the antibody. This method preferably comprises at least the following steps (a)–(c).

(a) incubating skin tissue derived from living organism in the presence of a substance to be tested, such as an oligopeptide of the present invention;

(b) recovering said skin tissue, and reacting it with a monoclonal antibody that specifically binds an antigen of about 220 kDa present in the epithelial new follicles, or an antibody fragment thereof; and (c) detecting or measuring said monoclonal antibody, or fragment thereof which reacted with the skin tissue pieces.

A method for the evaluation of hair growth promoting activity that relies on a monoclonal antibody that specifically binds an antigen of about 220 kDa present in epithelial new follicles, may be any method as long as it is an assay using an antibody or, in other words, an immunoassay. That is, the present invention encompasses the use of a monoclonal antibody that specifically binds an antigen of about 220 kDa present in epithelial new follicles, or a fragment of the antibody, to measure the presence of an antigen of about 220 kDa present in the epithelial new follicles in immunoassays known by those of skill in the art, wherein the presence of the antigen of about 220 kDa present in the epithelial new follicles is correlated with hair growth. Examples of such immunoassays include western blotting, enzyme-linked immunosorbent assay (ELISA), fluoroimmunoassay, radioimmunoassay (RIA), luminoimmunoassay, immunoenzymatic assay, immunofluorescence assay, immunoturbidimetry, latex agglutination reaction, latex turbidimetry, erythrocyte agglutination reaction and particle agglutination reaction.

There is no particular limitation for the type of the test substance which is subjected to the method for the evaluation of the present invention, and the test substance may be either oligopeptides, such as oligopeptides of the present invention, or low-molecular organic compounds. For example, there may be used an oligopeptide having a partial amino acid sequence of epimorphin.

When the method for the evaluation of hair growth promoting activity according to the present invention is carried out by means of an immunoassay using labeled antibody such as enzyme-linked immunosorbent assay (ELISA), fluoroimmunoassay, radioimmunoassay (RIA) or luminoimmunoassay, it is also possible to carry out the assay by a sandwich method or a competition method. In the case of a sandwich method, at least one of solid phase antibody and labeled antibody is the monoclonal antibody of the present invention.

With regard to the solid phase carrier, there may be used the above-mentioned carriers which are described in the present specification as specific examples for the insoluble carrier in relation to the immobilized antibody. Also with regard to the labeled substance, there may be used the above-mentioned substances which are described in the present specification in relation to the labeled antibody.

A method for the measurement may be carried out by a known method ("Immunoassay for Clinical Tests—Technique and Application", Special Issue No. 53 of *Rinsho Byori*, edited by the Japanese Society of Clinical Pathology, published by Rinsho Ryori Kankokai, 1983; "Enzyme-Linked Immunosorbent Assay" edited by Eiji Ishikawa, et al., Third Edition, published by Igaku Shoin, 1987; and "Enzyme-Linked Immunosorbent Assay", Supplementary Issue No. 31 of *Tampakushitsu, Kakusan, Koso*, edited by Tsunehiro Kitagawa, et al., published by Kyoritsu Shuppan, 1987).

For example, a solid phase antibody is reacted with a sample and a labeled antibody at the same time, or a solid phase antibody is reacted with a sample, and after being washed, it is reacted with a labeled antibody, thereby forming a complex of solid phase antibody-antigen-labeled antibody. Then, unbound labeled antibody is separated by washing, and the amount of the antigen in the sample can be measured from the amount of the bound labeled antibody. Specifically, in the case of the enzyme-linked immunosorbent assay (ELISA), the labeled enzyme is reacted with a substrate under an optimum condition and the amount of the reaction product is measured by, for example, an optical method. In the case of the fluoroimmunoassay, intensity of fluorescence by a fluorescent substance labeling is measured, and in the case of the radioimmunoassay, radiation dose by a radioactive substance labeling is measured. In the case of the luminoimmunoassay, amount of luminescence in the luminous reaction system is measured.

In the method for the detection and/or the quantitative determination according to the present invention, when the production of an immune complex aggregate by immunoturbidimetry, latex agglutination reaction, latex turbidimetry, erythrocyte agglutination reaction, particle agglutination reaction or the like is measured by measuring its transmitting light or scattering light by an optical method, or is measured visually, it is possible to use phosphate buffer, glycin buffer, Tris buffer, Good buffer or the like as a solvent, and a reaction promoting agent such as polyethylene glycol or a non-specific reaction suppressing agent may be contained therein.

When an antibody is used by sensitizing it to a solid phase carrier, there may be used particles made of the material such as polystyrene, styrene-butadiene copolymer, (meth) acrylate polymer, latex, gelatin, liposome, microcapsule, erythrocyte, silica, alumina, carbon black, metal compound, metal, ceramics or magnetic substance as a solid phase carrier.

The methods for the sensitization include known method such as physical adsorption, chemical bonding or a combination thereof. A method for the measurement may be carried out by a known method. For example, in the case of the measurement by an optical method, the sample is reacted with the antibody, or the sample is reacted with the antibody which was sensitized with a solid phase carrier. Then, the transmitting light or the scattering light is measured by an end-point method or a rate method.

When the measurement is carried out visually, the sample is reacted with the antibody sensitized with a solid phase carrier in a container such as a plate or a microtiter plate, and the state of agglutination is judged visually. Instead of measuring visually, the measurement may be carried out by an instrument such as a microplate reader.

Kit for Evaluation of Hair Growth Promoting Activity

A kit of the present invention for use in evaluating hair growth promoting activity of a test substance comprises a monoclonal antibody, or a fragment thereof, which specifically recognizes the antigen of about 220 kDa present in the epithelial new follicles or a fragment thereof. The monoclonal antibody which specifically recognizes the antigen of about 220 kDa present in the epithelial new follicles, or a fragment thereof, may be in an immobilized or labeled form.

For example, when a monoclonal antibody of the present invention which specifically recognizes the antigen of about 220 kDa present in the epithelial new follicles is used as a primary antibody, the kit of the present invention may further comprises a secondary antibody for the detection of a complex formed by the antigen-antibody reaction. The kit of the present invention may still further comprise various auxiliary agents in addition to those antibodies, so that the said kit can be utilized efficiently and easily. Examples of the auxiliary agent include those which are commonly used in a kit of reagents for immunological measurement, such as a solubilizer for dissolving the solid secondary antibody, a detergent used for washing the insoluble carrier, a substrate for measuring the enzymatic activity when an enzyme is used as a labeling substance for the antibody, and a reaction stopping agent. The kit of the present invention may also comprise the instructions for carrying out the evaluation of hair growth promoting activity.

The present invention will be explained more specifically by the following Examples. However, the scope of the invention is not limited to these examples.

EXAMPLES

Example 1

Preparation of Library Vector

A vector for presenting a peptide of about 10 amino acids on a surface of *E. coli* as a fused form with a surface protein (invasin) (Nakajima et al., *Gene,* 260, 121–131(2000)) was used. All BstXI sites were removed by using mutanegenis kit (Takara), the promoter region was replaced with $P_L$ promoter, and the amino acids 2–36 of thioredoxin cDNA was ligated to the C-terminal site of invasin cDNA. Further, the region of the 33th cysteine to 36th cysteine of ligated partial thioredoxin cDNA was replaced with TCCGGTCCGCCATCACGTTGGCTCGAGCCAGGATATTGGGGTCCGTGA (SEQ ID NO:136) to prepare a vector (designated as pALinvThio4).

A double stranded cDNA encoding HA epitope was inserted in frame to the BstXI site of this vector, and the obtained vector was introduced into *E. coli* G1724. The obtained strain was examined according to a similar method as in the first and second screening in Example 3 below. As a result, the *E. coli* strain was found to bind to anti-HA antibody. It was demonstrated that the peptide of HA epitope which was inserted as a model was presented on the surface of the cell.

Example 2

Preparation of a Library Presented on the Surface of *E. coli*

The following oligonucleotides were synthesized.

(SEQ ID NO:137)

1. 5' CTG CAG AAC CAT CAC GTT GG agT atT gaG caG agT tgT gaT caG gaT gaG C CAG GAT ATT GGA TGC AT 3'

(SEQ ID NO:138)

2. 5' CTG CAG AAC CAT CAC GTT GG agT atT gaG caG agT tgT gaT caG gaT gaG C CAG GAT ATT GGA TGC AT 3' wherein T, G, a, t, g, and c indicates the followings.

T: T:G = 17:3
G: T:G = 3:17
a: A:T:G:C = 7:1:1:1
t: A:T:G:C = 1:7:1:1
g: A:T:G:C = 1:1:7:1
c: A:T:G:C = 1:1:1:7

Equal amounts of oligonucleotides 1. and 2. above were mixed, and were annealed to the primer (5' ATG CAT CCA ATA TCC TGG 3') (SEQ ID NO:139). The DNA was extended with Klenow fragment, and was cut with a restriction enzyme BstXI, and the desired band was collected by polyacrylamide gel. The collected DNAs encode a group of peptides having a partial amino acid mutation in SIEQSCDQDE (SEQ ID NO:84).

The vector pALinvThio4 was cut with BstX, and was treated with BAP (bacterial alkaline phosphatase), and was then ligated to the above-obtained library fragments.

The obtained vector was transformed into electro competent cells of *E. coli* GI724 (15011) to prepare transformants which was designated as EPM pep7-like peptide library ($3.8\times10^6$). FIG. 3 shows theory values percentage present in the library.

An aliquot of EPM pep7-like peptide library was applied onto LB agar plate, and 100 colonies were randomly picked up, and the plasmids were separately collected and analyzed. As a result, it was found that about 30% of the colonies presented a peptide wherein 1 to 3 amino acids were substituted in the amino acid sequence SIEQSCDQDE (SEQ ID NO: 84) (which contains the murine pep7 region) (FIG. 1). Further, as a result of the analysis of the contents of the above-prepared library, it was found that the position and type of the amino acids which were substituted were random (FIG. 2). FIG. 2 shows a result of the analysis of 100 clones.

Example 3

First and Second Screening

EPM pep7-like peptide library (library size of $3.6\times10^6$) was induced to be expressed for 6 hours at 30° C. by addition of 100 μg/ml of tryptophan, and was added to a 35 mm dish which was previously coated with 10 μg of rabbit anti-epimorphin antibody (polyclonal antibody which neutralizes the activity of epimorphin; Hirai et al 1998 *J. Cell. Biol.,* 140:159–169) and was blocked with blocking solution (1% skim milk, 150 mM NaCl, 1% a-methyl mannoside in IMC medium), and left for 1 hour. Washing solution (1% α-methyl mannoside in IMC medium) was added thereto, and the dish was washed at 100 rpm for 5 minutes. Washing was repeated 5 times. After washing, the bound clones were collected. An aliquot of the bound clones was plated for the measurement of recover ratio, and the remaining was cultured overnight at 30° C. in IMC medium (obtained from Invitrogen; medium for culturing *E. coli* which does not contain tryptophan).

The first screened clones after culturing overnight were induced to be expressed by addition of tryptophan in the same way as above. The dish for second screening was coated with 10 μg of rat H12 antibody which was affinity-purified with EPM pep 7, and was blocked with a blocking solution containing 25 μg of each of recombinant H1-72, H1-73Δ, H1-78, H1-79 which has no hair growth promoting activity (see below) (total 100 μg) or 4 μg of each of synthesized peptides of the variable regions thereof (total 16 μg). In the same way as in the first screening, the clones whose expression was induced were added to the dish, and were washed. Then, the bound clones were collected. An aliquot of the bound clones was plated for the measurement of recover ratio, and the remaining was cultured overnight at 30° C. in IMC medium.

In both of the first and second screenings, cells where a vector of pALinvThio4 (containing no insert) was introduced were used as control. It was revealed from the plating that the collection ratio by panning under the above condition was less than 1/100 for the first screening, and less than 1/50 for the second screening, as compared with the case of using the library. The size of the thus obtained library was $2.5\times10^5$.

Variable region peptide (mutated peptide of pep7)

← ②

| | | | In vito activity |
|---|---|---|---|
| H1 | HI-6 | SIEQSCDQDE (SEQ ID NO:84) | O |
| H1-73Δ | ① → | SICEQSDQ (SEQ ID NO:94) | X |
| H1-75Δ | | SIEQCSDQ (SEQ ID NO:92) | O |
| H1-72 | | SCIEQSDQDE (SEQ ID NO:149) | X |
| H1-74 | | SIECQSDQDE (SEQ ID NO:132) | O |
| H1-78 | | SIEQSDQCDE (SEQ ID NO:150) | X |
| H1-79 | | SIEQSDQDCE (SEQ ID NO:151) | X |

primer ① Containing start codon of ORF of H1 and EcoR1 primer ② 6 types were designed to alter pep7 region of H1, containing stop codon and SmaI

| | | |
|---|---|---|
| R73Δ | GGG CCC GGG TCA CTG ATC GCT CTG GTC ACA AAT AGA CTT CAG CTT GCC CCG GAT CCT GTT | (SEQ ID NO:140) |
| R75Δ | GGG CCC GGG TCA CTG ATC GCT ACA CTG GTC AAT AGA CTT CAG CTT GCC CCG GAT CCT GTT | (SEQ ID NO:141) |
| R72 | GGG CCC GGG TCA CTC GTC CTG ATC GCT CTG GTC AAT ACA AGA CTT CAG CTT GCC CCG GAT CCT GGT | (SEQ ID NO:142) |
| R74 | GGG CCC GGG TCA CTC GTC CTG ATC GCT CTG ACA GTC AAT AGA CTT CAG CTT GCC CCG GAT CCT GTT | (SEQ ID NO:143) |
| R78 | GGG CCC GGG TCA CTC GTC ACA CTG ATC GCT CTG GTC AAT AGA CTT CAG CTT GCC CCG GAT CCT GTT | (SEQ ID NO:144) |
| R79 | GGG CCC GGG TCA CTC ACA GTC CTG ATC GCT CTG GTC AAT AGA CTT CAG CTT GCC CCG GAT CCT GTT | (SEQ ID NO:145) |

| | | | | |
|---|---|---|---|---|
| PCRcycle | 94° C. | 30 s | | PCR → treated with restriction enzyme (EcoRI, SmaI) |
| | 70° C. | 30 s | | |
| | 72° C. | 2 min | | Vector:pET-3 was altered and His-tag was integrated |
| | | cycle | 5 times | Similar restriction enzyme treatment |
| | 94° C. | 30 s | | → dephosphorylation treatment |
| | 75° C. | 30 s | | Ligation of PCR product + Vector → transformation |
| | 72° C. | 2 min | | → to plate pf LB + Amp |
| | | cycle | 20 times | |
| | 72° C. | 7 min | | |
| | 4° C. | ∞ | | |

Example 4

Recombination into a Vector for Large Scale Preparation

① A vector for large scale preparation of a high active recombinant epimorphin, SRαEPM (Hirai et al, (1994) *Eur. J. Biochem.,* 225, 1133–1139), was cut with HindIII, and the ends were made blunt with T4 polymerase. The vector was subjected to self-ligation to remove HindIII restriction site.

② Mutation introducing kit (TAKARA) was used to replace the AAGCTG which was located immediately upstream to the sequence encoding SIEQSCDQDE (SEQ ID NO; 84) of epimorphin which was inserted in the vector obtained in the above ①, with AAGCTT (restriction site of HindIII)

③ cDNA which encodes "NGN to C terminal of 12 fragments (*Eur. J. Biochem,* 225, 1133–1139)" immediately downstream to SIEQSCDQDE (SEQ ID NO:84) of murine epimorphin was prepared by PCR in a form having a restriction site of HindIII, and this cDNA was inserted into HindIII site of the vector prepared in the above ②. The epimorphin which was inserted into the vector is composed of 12 fragments and lacks peptide 7, and HindIII restriction site is added thereto.

④ AgCTTCCATCACgTTggTCTAgACCAggATATTggA (SEQ ID NO:146) AggTAgTgCAACCAgATCTggTC-CTATAACCTTCgA (SEQ ID NO:147) was prepared by chemically synthesizing each strand and then annealing them at 70–50° C., and was introduced into HindIII site prepared in the above ③ to convert Hind III restriction site to Hind III-BstXI-XbaI-BstXI-Hind III.

⑤ A group of plasmids were collected from *E. coli* group (overnight culture at 30° C.) obtained by the second screening, and cDNAs encoding pep7-like peptide groups, which was obtained by cutting at BstXI site, were inserted into BstXI XbaI BstX site of the vector prepared in the above ④.

⑥ An aliquot of the obtained plasmid groups was cloned into *E. coli* HB101, and 15 clones were examined. As a result, it was found that all clones have a sequence which encodes epimorphin 12 fragments wherein one or more amino acids in the pep7 region are substituted with another amino acid.

⑦ The group of plasmids obtained in the above ⑤ was treated with NspV/PvuII to obtain a group of genes of epimorphin fragment containing mutated pep7. These fragments were inserted into the NspV-SmaI site of the vector pet12 (Hirai et al. *J. Cell. Biol.,* 2001, 153, 785–794 for large scale preparation of epimorphin 12 fragments having 6 His at N-terminal (referred to as library for large scale preparation).

⑧ An aliquot of the thus obtained plasmid group was cloned in *E. coli* BL21, and the protein expression and the internal sequence of each clone were examined. As a result, all clones showed an induction of protein expression by IPTG, and epimorphin fragments wherein pep7 region is substituted with a different peptide and which lacks the region from C terminal to PvuII site of H12 were confirmed. A library of $2.5\times10^5$ for large scale expression was constructed.

Example 5

Preparation of pep7-Like Peptide

① The library for large scale preparation was introduced into *E. coli* BL-21, and applied onto LB-agarose (containing Amp) plate. On the next day, the library was cloned from the plate to each well of 96-well plate containing LB, and at the same time, a master plate was prepared. The plates were incubated overnight at 32° C., and then was treated with 1 mM (final concentration) of IPTG for 2 hours. Then, His-tag proteins of each well were collected in a form which was bound with Ni-NTA (Qiagen) according to the manual of Qiagen. The details are disclosed below.

The plate was centrifuged at 2000 rpm for 15 minutes, and the medium was discarded. 50 µl of 2 mg/ml lysozyme was added to each well, and the plate was incubated for 1 hour. The operation of freezing with liquid nitrogen and melting at room temperature was repeated twice. The wells were treated with DNAse, and all proteins were dissolved by 150 µl of 8M urea (pH8.0). Ni-NTA gel (Qiagen) equilibrated with 8M urea was added, and the wells were incubated for 30 minutes. The plate was centrifuged at 2000 rpm for 1 minute and the supernatant was discarded. The wells were washed twice with PBS, and once with water.

② Trypsin (sequence grade; Promega) was added to each well at a final concentration of 1 µg/ml, and the plate was incubated overnight at 37° C.

③ After the plate was treated at 95° C. for 5 minutes, the solution was collected, and the same amount of 2×DH10 (a mixed medium of DMEM and Ham12 (Gibco) supplemented with 10% FCS) was added thereto to prepare the samples. By the analysis with liquid chromatography, it was confirmed that the difference between the samples was the mutation of pep7 regions. Also, the sequence of each clone was analyzed using the master plate.

Example 6

Preparation of a Monoclonal Antibody which is Specific for New Follicle

Hairs were cut off from the skin of B57BL mouse of growing stage (48 to 50 day), and were incubated overnight at 37° C. in PBS containing 8M urea, 2% SDS and 100 mM DTT, thereby the protein was extracted. Further, whisker follicles of B57BL mouse (where hair ball portion is stained with pigment; growing stage) were collected with a stereoscopic microscope, and were homogenized in PBS. The above 2 samples (0.5 mg of protein weight) were mixed, and mixed with the same amount of the complete adjuvant to prepare micelle.

The above-obtained micelle (0.2 mg) was subcutaneously (3 sites) administered to a rat (Wister) for immunization. After the first immunization, the booster was performed in the same way as in the above. After 2 weeks, the second booster was performed in the same way as in the above. On the third day after the second booster, a spleen was removed from the immunized rat, and the blood cells were collected by mesh. Antibody producing cells were contained in these blood cells. All amount of the above-collected blood cells were mixed with mouse myeloma P3U1 using polyethyleneglycol 1500, and were suspended in Dulbecco/Hum F12 mixed medium. 100 µl of the culture were inoculated in each well of 96-well plate. On the next day, the same amount (100 µl) of HAT medium (Sigma) was added to each well. After 2 days, 150 µl of the medium was removed under aspiration from each well, and 150 µl of the fresh medium was added to each well. The 96-well plate was placed in $CO_2$ incubator at 37° C.

The follicles of the growing whisker of B57BL mouse were dissolved in 8M urea by ultrasonic treatment. A nitrocellulose membrane was immersed in this solution for 5 minutes, and was washed well with PBS. Biorad dot blotter equipped with the above membrane was used to perform the first screening of the hybridoma supernatant which was recovered from each well of the above 96-well plate. First, the above prepared nitrocellulose membrane was blocked with Tris buffer containing 5% skim milk (TBST), and then 100 µl of the hybridoma supernatant was added to each well where the nitrocellulose membrane constitutes the bottom. After incubation for 1 hour, the wells were washed with Tris buffer, and the second antibody, horseradish peroxidase labeled anti-rat IgG (1 µg/ml TBST), was added. ECL agent (AmershamPharmacia), which is a coloring substrate, was added, and 50 antibodies in total which reacted with the growing whisker follicle were selected by detection of coloring (first screening).

Among the 50 antibodies selected in the above first screening, the antibodies which specifically reacted with the frozen segment (10 µm) of the growing whisker follicle were selected (second screening). Specifically, the frozen segment of the growing whisker follicle was placed on a slide glass, and the hybridoma supernatant selected in the first screening was added thereto, and the coloring was developed with the second antibody. More specifically, the frozen segment of the growing whisker follicle which was prepared by Cryosdat (Bright) was treated with methanol at −20° C., and was blocked with TBST for 1 hour, and then was reacted with the hybridoma supernatant for 1 hour. The sample was washed with Tris buffer, and was reacted with FITC-labeled anti-rat IgG (100 µg/ml in TBST). The sample was washed with Tris buffer, and was covered with a cover glass. The observation was carried out under fluorescent microscope.

As a result of the second screening, 8 antibodies were selected. These antibodies did not react with epidermis, and specifically reacted with follicle. These 8 antibodies were cloned by the limiting dilution.

The reactivity of these 8 antibodies was examined by Western Blotting using growing whisker follicle (anagen phase) or resting (telogen) whisker follicle as a sample, and using slide samples of the skins having follicles derived from 14 day fetal mouse. As a result, mAb27 was obtained as a monoclonal antibody which specifically reacted with growing whisker follicle and plastic follicle (new follicle), and did not react with resting whisker follicle. The hybridoma which produced monoclonal antibody mAb27 was deposited with Patent and Bio-Resource Center of National Institute of Advanced Industrial Science and Technology (Chuo-6, 1-1, Higashi 1-chome, Tsukuba-shi, Ibaraki-ken, Japan) on Nov. 2, 2001 under the deposit number of FERM P-18578.

Figure 12:
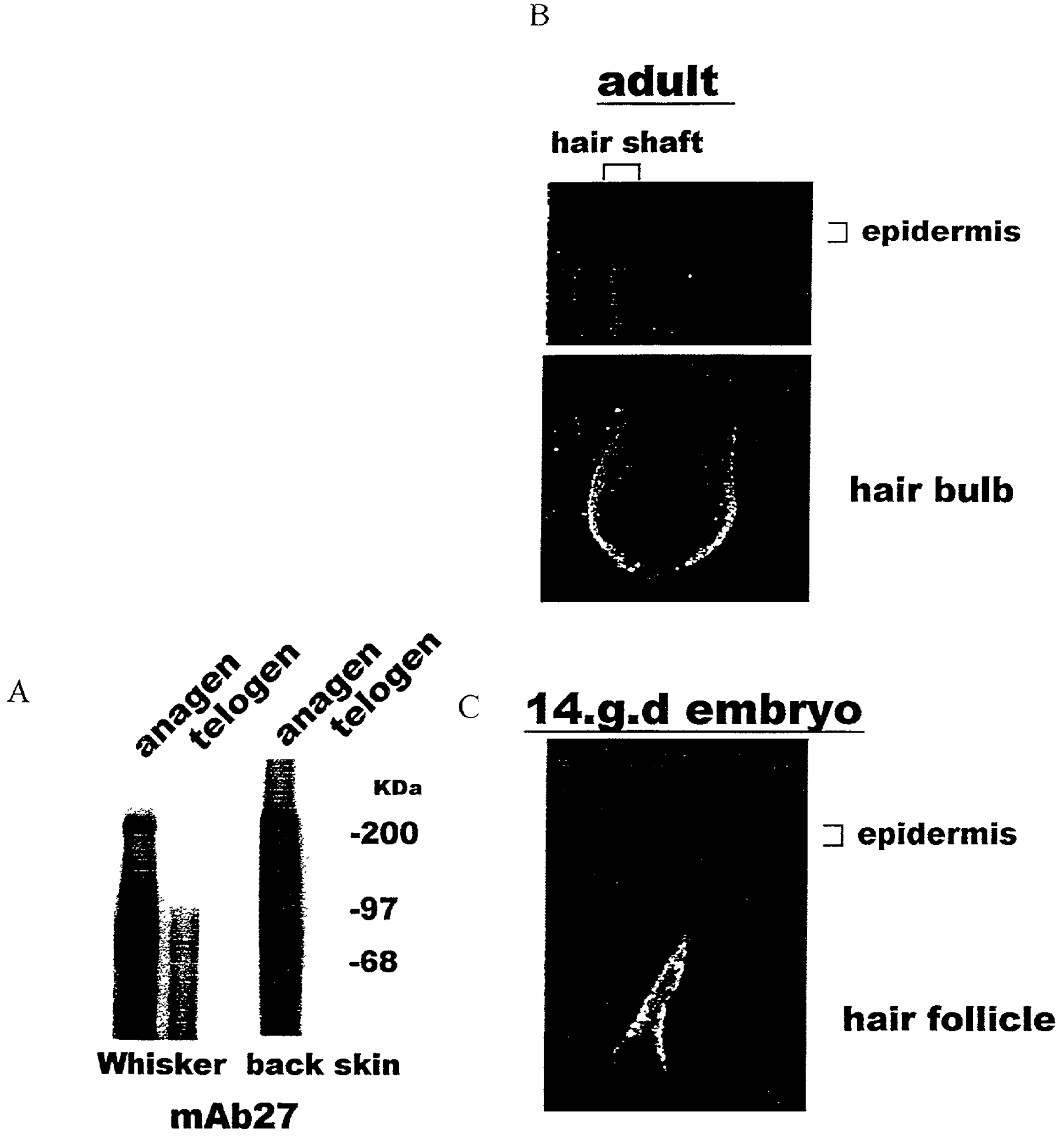
FIG. 12 (A) shows the result of detection of the antigen of mAb27 by Western blotting. Each of the lanes from left to right shows the result of the analysis where each protein extracted from the anagen and telogen stage of whisker and the anagen and telogen stage of back skin was subjected to electrophoresis and Western blotting, and then the antigen was detected by using the monoclonal antibody mAb27.

FIG. 12 (A) shows the result of detection of the antigen of mAb27 by Western blotting. Each of the lanes from left to right shows the result of the analysis where each protein extracted from anagen and telogen of whisker and anagen and telogen of back skin was subjected to electrophoresis and Western blotting, and then the antigen was detected by using the monoclonal antibody mAb27 of the present invention.

Specifically, the solution obtained by milling whisker follicle with ultrasonic treatment in 8M urea was used as an antigen without dilution. The electrophoresis was carried out under a condition of a constant electric current of 30 mA in SDS-PAGE (acrylamide 4 to 20%). Running buffer is 14.4 g/L of glycine, 1 g/L of Tris, and 1 g/L of SDS. After electrophoresis, the sample was transferred to PVDF membrane, and was incubated in Tris buffer containing 5% skim milk (TBST) for 1 hour. Then, the sample was reacted with mAb27 (100 μl of hybridoma supernatant) for 1 hour, and washed well with TBS, and was reacted with peroxidase-labeled anti-rat IgG (Amersham) (dissolved at 1 mg/ml in TBST) as a second antibody. After washing well, the intensity of the reaction of mAb27 was measured by using ECL kit (Amersham).

As a result, it was found that the monoclonal antibody mAb27 of the present invention detected an antigen of about 220 kDa specifically present in an anagen sample.

FIG. 12 (B) shows the result of histological staining using hair of adult and FIG. 12 (C) maxilla of 14th day mouse embryo. The procedure is same as in the procedure of the second screening of the antibodies in Example 1.

As a result, it was found that, in the case of using the monoclonal antibody mAb27 of the present invention, epidermis was not stained and only hair bulb was stained in hair of adult, and epidermis was not stained and only hair follicle was stained in maxilla of 14th day mouse embryo.

From the results shown in FIGS. 12 (A)-(C), it was demonstrated that the monoclonal antibody mAb27 of the present invention specifically recognized an antigen of about 220 kDa present in new follicle.

Example 7

Evaluation of Hair-Growth Promoting Activity

The skin of the back of ICR mouse (pregnancy 14 days) was pealed off by pincette, and was collected in HCMF. The collected skin was transferred to a plate, and was cut into pieces using 2 knives with grip. The cut skin was transferred to 15 ml centrifuge tube, and was centrifuged at 1000 rpm for 1 second. 0.50 μl of DNase (2 mg/ml) was added to the precipitate, and the mixture was homogenized. 10 ml of DH1 medium was added and the mixture was centrifuged. 10 ml of DH10 medium was added to the precipitate, and the mixture was suspended. After the mixture was suspended to be homogenized using a tip, 100 μl of the suspension was applied onto each 96-well plate.

Onto the suspension in 96 well plates, 50 μl of each sample obtained in Example 5 ③ above was added respectively, and the plates were incubated at 37° C. for 2 days in $CO_2$ incubator. During incubation, PBS was filled in the gaps between wells for avoiding drying, and the plate was sealed. After incubation, 100 μl of 8M urea was added.

A paper and a nitrocellulose membrane which have been immersed in TBS were set on Dot blotter (96 well) produced by BioRad. Such equipment was prepared in 3 sets. 10 μl was applied to 2 membranes where one (panel A) is used for monoclonal antibody mAb27, and the other is used for anti-E-cadherin (TAKARA) which detects all epitheliums. After blotting the solution into membrane by aspiration, the membranes were removed and dried at room temperature for 10 minutes. The membranes were washed once with TBS, and blocked with skim milk at room temperature for 1 hour. Then, the membranes were incubated with the primary antibody, monoclonal antibody mAb 27 (the culture supernatant of hybridoma was diluted to 1/30) or anti-E-cadherin antibody (1/2000 diluted, TAKARA) at room temperature for 1 hour. The membranes were washed twice with TBS for each 10 minutes. Then, peroxidase labeled anti-rat IgG or peroxidase labeled anti-rabbit IgG (Amersham) (1/1000 diluted) was reacted as the second antibody, and the membranes were washed twice with TBS for each 10 minutes. The intensity of the reaction was examined using ECL plus (Amersham).

Example 8

Data Analysis

The autora-film of those detected by ECL was uptaken using Fuji Photo Film luminoimage analyzer (LAS-1000plus). The amount of the antigen of monoclonal antibody mAb27 was measured from panel A as an index of induction of new follicle, and the amount of E-cadherin was measured from panel B as an index of total numbers of epithelial cells.

The ratio of the measured amounts obtained from panel A and panel B was analyzed by computer, and the degree of the induction of hair-growth per epithelial cell was analyzed.

As a result of the analysis of 960 samples in total, samples were obtained where the measured amount from panel A is higher than the measured amount from panel B (i.e., samples having a high ability of inducing new follicle). The pep7-like sequences of 65 samples among such samples are shown herein in Table I. The requirements of the structure of the amino acid sequences of these 65 clones are also shown in Table II.

The samples where the measured amount from panel A is higher than the measured amount from panel B, are shown in Table III. The amino acid sequences of these samples are:

```
Tyr Asn Glu Gln Ser Cys Asp Arg Glu Glu (SEQ ID NO:
                                         17)

Thr Ser Asp Gln Cys Cys Asp Pro Asp Lys (SEQ ID NO:
                                         76)

Pro Ser Glu Gln Ser Cys Ala Glu Glu Glu (SEQ ID NO:
                                         61)

Ser Asn Glu Gln Ser Cys Ala Val Ala Glu (SEQ ID NO:
                                         29)

Thr Thr Glu Gln Ser Cys Ala Val Asp Glu (SEQ ID NO:
                                         63)

Ser Ile Glu Gln Ser Cys Gly Gln His Glu (SEQ ID NO:
                                         81)

Ser Ser Ala Gln Ser Cys Leu Gln Asp Thr (SEQ ID NO:
                                         48)

Tyr Ile Glu Gln Tyr Cys Asp Gln Asp Glu (SEQ ID NO:
                                         64)

Thr Ile Trp Gln Ser Cys Asp Gln Glu Glu (SEQ ID NO:
                                         32)
```

The activity of these peptides is about 3 times higher than the peptide of amino acid sequence Ser Ile Glu Gln Ser Cys Asp (SEQ ID NO:87), from the pep7 region of murine epimorphin.

Among the 65 clones, there is a peptide of 7 amino acid residues having an amino acid sequence of Ser-Ile-Glu-Gln-Ser-Cys-Asp (SEQ ID NO:87). Therefore, this 7 amino acid residues is considered to be a region necessary for hair growth promoting activity.

In the 65 clones, Cys residue is not substituted with another amino acid, and therefore, a Cys residue is important in the oligopeptides of the present invention. Monomers comprising a Cys amino acid residue would be capable of dimerizing under suitable conditions.

In the 65 clones, the amino acid sequence of Glu-Gln-Ser-Cys-Asp (SEQ ID NO:119) is relatively highly conserved (i.e., conserved in 23 clones), and the amino acid sequence of Glu-Gln-Ser-Cys (SEQ ID NO:120) is further highly conserved (i.e., conserved in 30 clones).

In the Examples, 65 peptide clones having a high ability to induce a new follicle were obtained from 960 samples. $2.5\times10^5$ peptide clones were obtained in the second screening as shown in Example 3, and peptides having the same ability other than the above 65 clones are considered to be contained therein. In some examples, 3 amino acid residues among 7 amino acid residues may be substituted. If the candidate amino acid for respective amino acid is composed of 8 types, the total number of combination is estimated as ${}_7C_3\times8^3=17920$. The ratio of 17920 clones in the library of $2.5\times10^5$ is 7.1%. On the other hand, the ratio of 65 clones in the population of 960 samples is 6.8%. The aforementioned assumption is well consistent with the result of the Examples of the present application (the ratio of the peptides which is positive in the screening).

The following oligopeptides based on the sequence provided in Table II (shown in one letter amino acid code) are predicted to exhibit hair-growth promoting activity:

```
SIDQSCD    (SEQ ID NO:121)
SIEESCD    (SEQ ID NO:122)
SIEQACD    (SEQ ID NO:123)
SIEQSCR    (SEQ ID NO:124)
SIEQFCH    (SEQ ID NO:125)
SFDQSCD    (SEQ ID NO:126)
SFEESCD    (SEQ ID NO:127)
SFEQACD    (SEQ ID NO:128)
SFEQSCR    (SEQ ID NO:129)
SFEQFCH    (SEQ ID NO:130)
```

Example 9

Altered Oligopeptides

Oligopeptides (A), (B), (C) and (D) represented by the following amino acid sequences were synthesized by solid phase method using Fmoc.

```
                                   (SEQ ID NO:131)
A.   Ser-Ile-Glu-Gln-Cys-Ser-Asp-Gln-Asp-Glu

                                   (SEQ ID NO:132)
B.   Ser-Ile-Glu-Cys-Gln-Ser-Asp-Gln-Asp-Glu
```

-continued

```
                                   (SEQ ID NO:133)
C.   Ser-Ile-Cys-Glu-Gln-Ser-Asp-Gln-Asp-Glu

                                   (SEQ ID NO:93)
D.   Ser-Ile-Glu-Cys-Gln-Ser-Asp-Gln
```

The synthesized oligopeptides were dimerized using a cross-linking agent (bismaleimide hexane, trade name BMH, produced by Pierce) to prepare a homodimer. Specifically, the synthesis was carried out according to the instructions of this cross-linking agent.

The obtained reaction mixture contained not only homodimer oligopeptide, but also monomer oligopeptide to which a cross-linking agent was bound.

In the same way as in the above, oligopeptides Ser-Ile-Glu-Gln-Ser-Cys-Asp (SEQ ID NO:87) and Ser-Ile-Glu-Gln-Cys-Ser-Asp (SEQ ID NO:4) were used in an equal amount to prepare heterodimer oligopeptide. The obtained reaction mixture contained not only a heterodimer oligopeptide, but also monomer oligopeptide to which a cross-linking agent was bound.

Each of the synthesized oligopeptides (A), (B) and (C) was purified by a high performance liquid chromatography (HPLC), and it was confirmed by HPLC and Mass that the purity was 90% or more.

The conditions of HPLC are mentioned below.

Column: ODS-UG3 (Monomeric ODS, Nomura Kagaku), 1.0 mm in inside diameter, 100 mm in length Measurement: room temperature (25° C.)

Detection: UV 214 nm, 280 nm

Eluting solvent: gradient of solvent A and solvent B (solvent A: 0.1% trifluoroacetic acid; solvent B: 90% acetonitrile/0.1% trifluoroacetic acid, linear concentration gradient from 5 minutes after (solvent B: 0%) to 55 minutes (solvent B: 55%)

Flow rate: 75 ml/ml

Retention time of oligopeptides 21.52 minutes (dimer), 20.59 minutes (monomer)

Example 10

Evaluation of Hair Growth Promoting Activity of Altered Oligopeptides

The skin tissues of maxilla of ICR mice (pregnancy 12 days) were collected by stereoscopic microscope, and left and right sides were respectively recovered from 5 mice. 5 pieces of each of the thus collected left (for control) and right (for test oligopeptides) skins from 5 mice were respectively placed on 1 nuclepore membrane (pore diameter 8 μm; diameter 13 mm), and were set in such a way that the outside upturns by observing the samples with stereoscopic microscope. 500 μl of Dulbecco's MEM/Ham F12 medium containing 1% BSA was added to 2 wells of 24 well dish. The test oligopeptide in a solvent (PBS) was added in a final concentration of 20 μCM to one well, and solvent (PBS) was added in the same amount to the other well as a control. The oligopeptides synthesized in Example 9 were used as the test oligopeptides.

Each membrane having skin tissues thereon was launched on the solution in the above wells, and was incubated at 37° C. for 6 days. 5 pieces of tissue were recovered from the membrane into 100 μl of SDS sample buffer (SDS 0.02 g/ml, glycerol 0.2 g/ml, pH6.8), and dissolved by ultrasonic treatment. The control membrane was also treated similarly. The solution obtained by such a treatment was subjected to electrophoresis (35 mA, 1.5 hour) in SDS-PAGE (acrylamide 4–20%), and transferred to PVDF membrane, and incubated in Tris buffer containing 5% skim milk (TBST) for 1 hour. The membrane was reacted with mAb 27 (10 μg/ml in TBST) obtained in Example 2 for 1 hour, and was washed well with TBS. Then, peroxidase labeled anti-rat IgG (Amersham) (1/1000 diluted in TBST) was reacted as the second antibody, and the membrane was washed well with TBS. The intensity of the reaction of mAb 27 was examined using ECL kit (Amersham).

Figure 4:
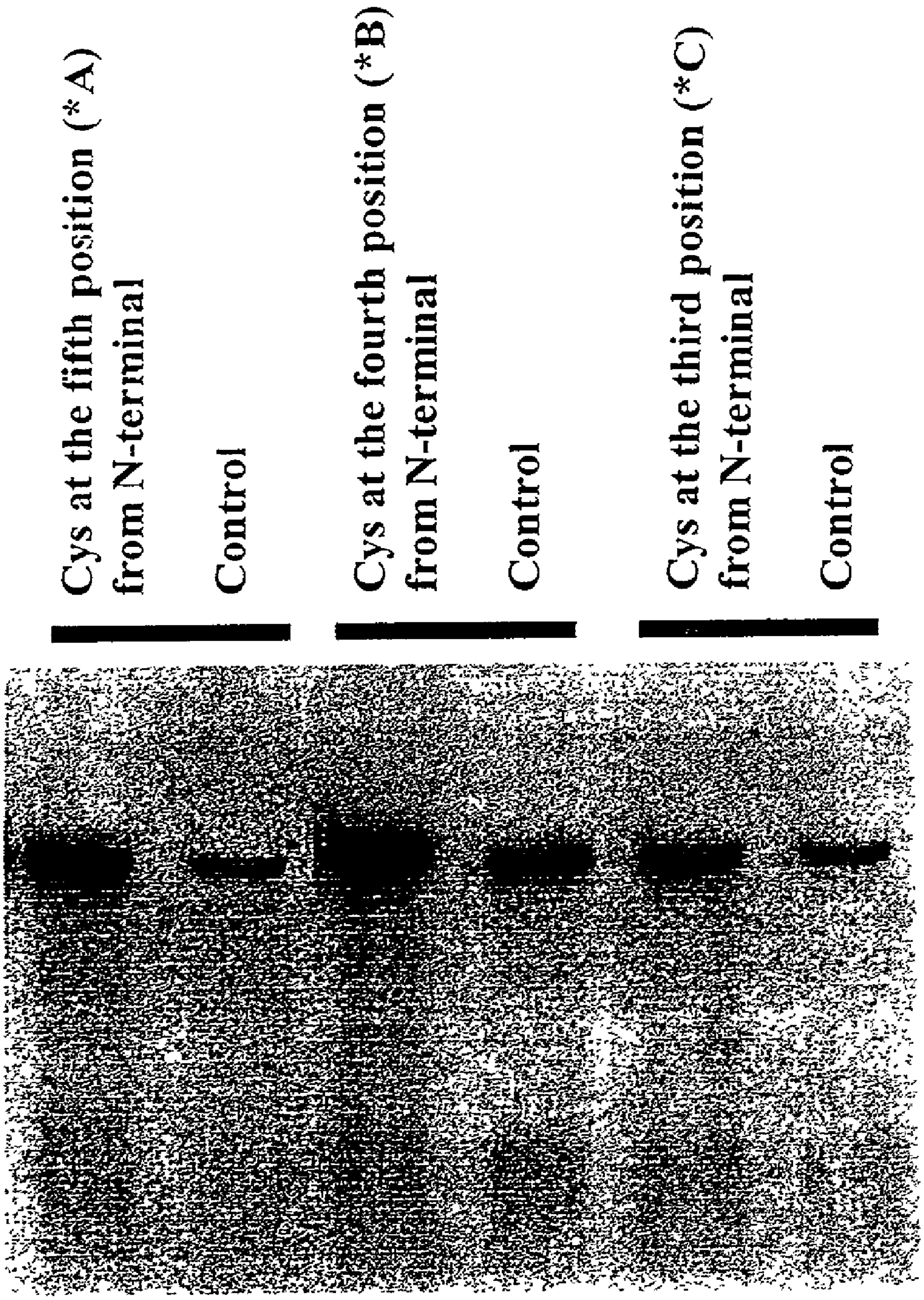
FIG. 4 shows the result of an analysis for hair growth promoting activity using homodimer oligopeptides as described in Examples 9–10.
Figure 5:
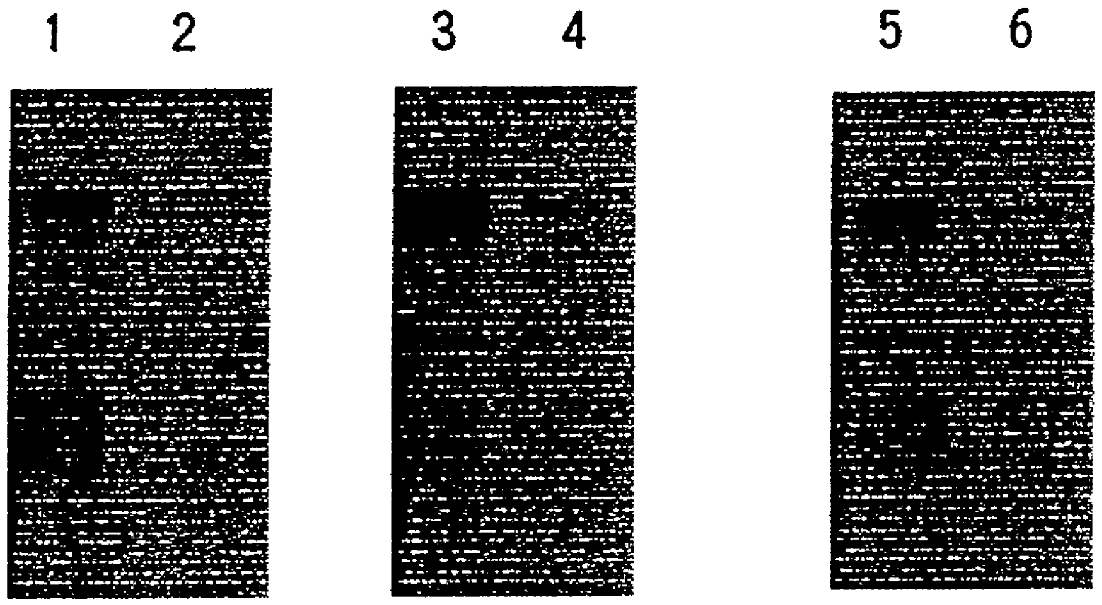
FIG. 5 shows the result of a test for hair growth promoting activity using heterodimer oligopeptide and homodimer oligopeptides as described in Examples 9–10.

The obtained results are shown in FIG. 4 and FIG. 5.

The test oligopeptides in each lane of FIG. 4 are as follows.

First from left: Ser-Ile-Glu-Gln-Cys-Ser-Asp-Gln-Asp-Glu (A) (SEQ ID NO:131)

Second from left: Control

Third from left: Ser-Ile-Glu-Cys-Gln-Ser-Asp-Gln-Asp-Glu (B) (SEQ ID NO:132)

Fourth from left: Control

Fifth from left: Ser-Ile-Cys-Glu-Gln-Ser-Asp-Gln-Asp-Glu (C) (SEQ ID NO:133)

Sixth from left: Control

As is understood from the results of FIG. 4, the bands in the first, third and fifth lane from the left were stronger than the bands in the second, fourth and sixth lane from the left respectively. These results demonstrate that the test oligopeptides (A), (B) and (C) have a hair growth promoting activity.

The test oligopeptides in each lane of FIG. 5 are as follows.

First from left: a mixture obtained by mixing oligopeptide (A) and oligopeptide (B) after treating them.

Second from left: Control

Third from left: a mixture obtained by treating oligopeptide (A) and oligopeptide (B) after mixing them.

Fourth from left: Control

Fifth from left: Ser-Ile-Glu-Cys-Gln-Ser-Asp-Gln (D) (SEQ ID NO:93) (having two amino acids at the C-terminus of (b) removed).

Sixth from left: Control

As is understood from the results of FIG. 5, similar activities were observed in the mixture obtained by mixing oligopeptide (A) and oligopeptide (B) after treating them, and the mixture obtained by treating oligopeptide (A) and oligopeptide (B) after mixing them. Therefore, it was demonstrated that heterodimer oligopeptide had also a hair growth promoting activity. It was also found that oligopeptide (D) with 2 amino acids at C-terminal being deleted had a hair growth promoting activity.

Example 11

Various oligopeptides wherein the cysteine residue in the oligopeptides:

```
Ser Ile Asp Gln Ser Cys Asp   (SEQ ID NO:121)

Ser Ile Glu Glu Ser Cys Asp   (SEQ ID NO:122)
```

-continued

```
Ser Ile Glu Gln Ala Cys Asp   (SEQ ID NO:123)

Ser Ile Glu Gln Ser Cys Arg   (SEQ ID NO:124)

Ser Ile Glu Gln Phe Cys His   (SEQ ID NO:125)

Ser Phe Asp Gln Ser Cys Asp   (SEQ ID NO:126)

Ser Phe Glu Glu Ser Cys Asp   (SEQ ID NO:127)

Ser Phe Glu Gln Ala Cys Asp   (SEQ ID NO:128)

Ser Phe Glu Gln Ser Cys Arg   (SEQ ID NO:129)

Ser Phe Glu Gln Phe Cys His   (SEQ ID NO:130)
```

was moved upstream by 1, 2 or 3 amino acids, were synthesized as in Example 9, and were evaluated as to hair-growth promoting activity in the same way as in the above.

As a result, the activity is observed. That is, it was found that the amino acid sequence of Ser-Ile-Glu-Gln-Cys-Ser-Asp (SEQ ID NO:4), Ser-Ile-Glu-Cys-Gln-Ser-Asp (SEQ ID NO:5) or Ser-Ile-Cys-Glu-Gln-Ser-Asp (SEQ ID NO:6) wherein the position of Cys is altered, showed a hair growth promoting activity. Each amino acid in these peptides can also be substituted as in the case of Ser-Ile-Glu-Gln-Ser-Cys-Asp (SEQ ID NO:87). For example, the peptide of the amino acid sequence Ser Asn Glu Pro Cys Ser Asp Gln Gly Gly (SEQ ID NO:24) is obtained by substituting Ile and Gln with Asn and Pro respectively in the peptide of amino acid sequence of Ser-Ile-Glu-Gln-Cys-Ser-Asp (SEQ ID NO:4), and it is considered that the peptide having such substitutions will show a hair growth promoting activity, as is the case shown in the present specification.

Example 12

Preparation of Modified Oligopeptides

Figures 10A, 10B, 10C:
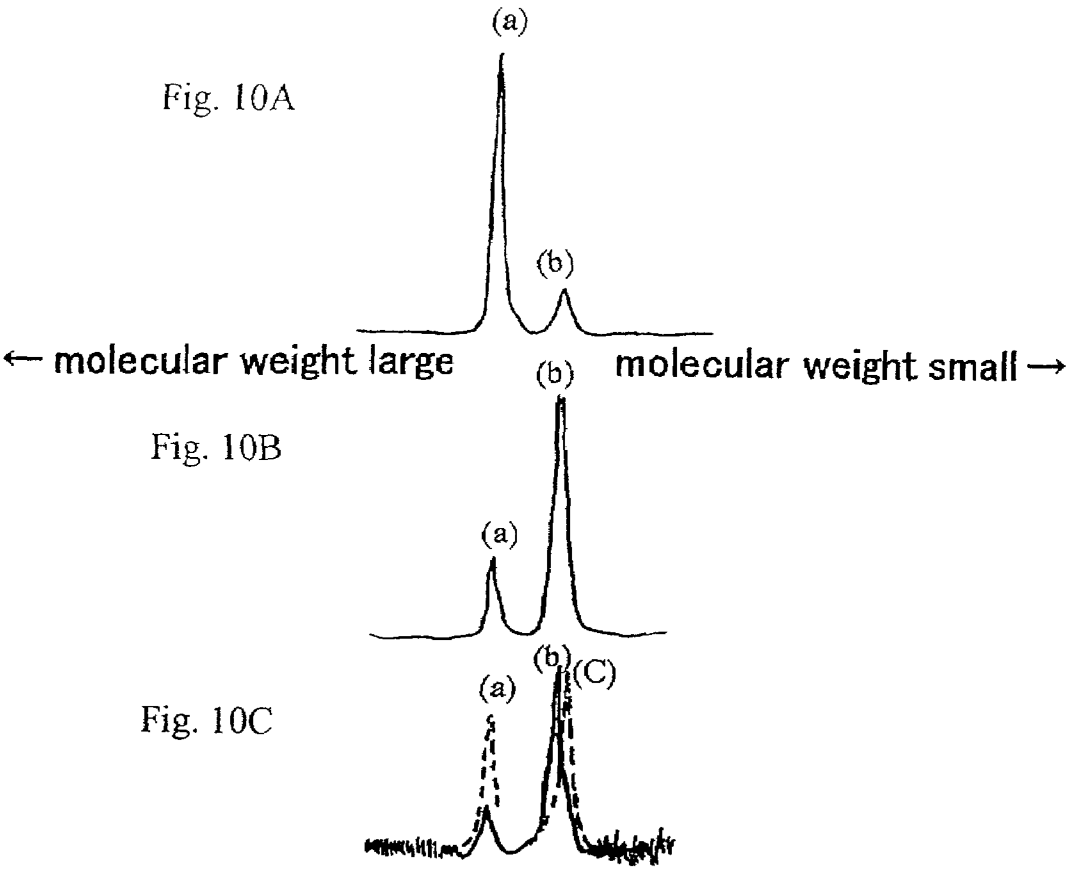
FIGS. 10A–10C show the result obtained by analyzing the reaction product of the oligopeptide and the cross-linking agent with gel permeation column as disclosed in the Example 12.

An oligopeptide represented by the following amino acid sequence was synthesized by solid phase method using Fmoc. Ser-Ile-Glu-Gln-Ser-Cys-Asp-Gln-Asp-Glu (SEQ ID NO:84) (comprising murine pep7 region). Then, the synthesized oligopeptide was reacted with a cross-linking agent (bismaleimide hexane, trade name BMH, produced by Pierce) according to the instructions of this cross-linking agent. The reactions were carried out in various ratios of the oligopeptide and the cross-linking agent. FIGS. 10A–10C shows the result obtained by analyzing the reaction product of the oligopeptide and the cross-linking agent with gel permeation column (Amersham Pharmacia, Superdex™ peptide PC 3.2/30, 250 mM NaCL, 20 mM Na-phosphate buffer (pH7.2) was used as a developing solution).

The upper diagram (A) in FIG. 10 shows the result obtained by reacting the oligopeptide with bismaleimide in a ratio of 7:3 and separating with liquid chromatography (Amersham Pharmacia, Smart system). Peak (a) represents a peptide dimer, and peak (b) represents a peptide dimer having a reactive maleimide. Peak (a) corresponds to the time when 1.2 ml was eluted, and peak (b) corresponds to the time when 1.4 ml was eluted.

The middle diagram (B) in FIG. 10 shows the result obtained by reacting the oligopeptide with bismaleimide in a ratio of 2:5. Peak (a) represents a peptide dimer, and peak (b) represents a peptide dimer having a reactive maleimide. Since bismaleimide hexane exists in excess, the peptide dimer having a reactive maleimide (b) has been formed in larger amount than the peptide dimer (a).

The lower diagram (C) in FIG. 10 shows the result of the sample obtained by adding an non-modified oligopeptide Ser-Ile-Glu-Gln-Ser-Cys-Asp-Gln-Asp-Glu (SEQ ID NO:84) in excess to the sample of the above (B) (i.e., the sample obtained by reacting the oligopeptide with bismaleimide in a ratio of 2:5). From the result where Peak (b) decreases and peak (a) increases, it is understood that a part of (c) which was added is reacted with (b) to form a dimer (a).

Example 13

Evaluation of Hair Growth Promoting Activity of Various Oligopeptides (1) Preparation of Various Oligopeptides Oligopeptides (A) and (B) represented by the following amino acid sequences were synthesized by solid phase method using Fmoc (hereinafter, these are referred to as the unmodified oligopeptides).

```
                                    (SEQ ID NO:84)
(A)     Ser-Ile-Glu-Gln-Ser-Cys-Asp-Gln-Asp-Glu

                                   (SEQ ID NO:134)
(B)     Ser-Ile-Glu-Gln-Ser-Lys-Asp-Gln-Asp-Glu
```

The synthesized oligopeptide (A) was reacted with a cross-linking agent (bismaleimide hexane, trade name BMH, produced by Pierce) according to the instructions of this cross-linking agent. Also, the synthesized oligopeptide (B) was reacted with a cross-linking agent DSG (disuccinimidyl glutarate). Using a fraction collector, the monomer to which the cross-linking agent was bound was fractioned and collected.

(2) Evaluation of Hair Growth Promoting Activity

The skin tissues of maxilla of ICR mice (pregnancy 12 days) were collected by stereoscopic microscope, and left and right sides were respectively recovered from 5 mice. 5 pieces of each of the thus collected left (for control) and right (for test oligopeptides) skins from 5 mice were respectively placed on 1 nuclepore membrane (pore diameter 8 μm; diameter 13 mm), and were set in such a way that the outside upturns by observing the samples with stereoscopic microscope. 500 μl of Dalbecco's MEM/Ham F12 medium containing 1% BSA was added to 2 wells of 24 well dish. The test oligopeptide in a solvent (PBS) was added in a final concentration of 20 μM to one well, and solvent (PBS) was added in the same amount to the other well as a control. The unmodified and modified oligopeptides synthesized in the above (1) were used as the test oligopeptides.

Each membrane having skin tissues thereon was launched on the solution in the above wells, and was incubated at 37° C. for 6 days. 5 pieces of tissue were recovered from the membrane into 100 μl of SDS sample buffer (SDS 0.02 g/ml, glycerol 0.2 g/ml, pH6.8), and dissolved by ultrasonic treatment. The control membrane was also treated similarly. The solution obtained by such a treatment was subjected to electrophoresis (35 mA, 1.5 hour) in SDS-PAGE (acrylamide 4–20%), and transferred to PVDF membrane, and incubated in Tris buffer containing 5% skim milk (TBST) for 1 hour. The membrane was reacted with mAb 27 (10 μg/ml in TBST) obtained in Example 6 for 1 hour, and was washed well with TBS. Then, peroxidase labeled anti-rat IgG (Amersham) (1/1000 diluted in TBST) was reacted as the second antibody, and the membrane was washed well with TBS. The intensity of the reaction of mAb 27 was examined using ECL kit (Amersham).

Figure 11:
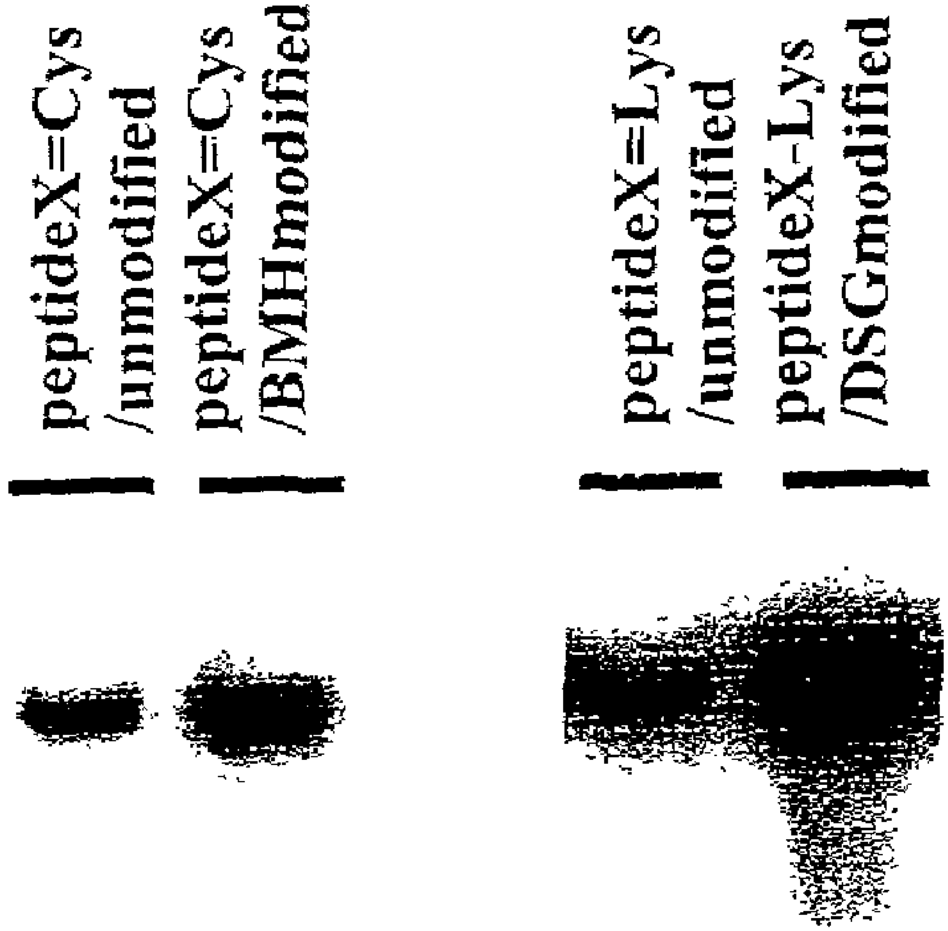
FIG. 11 shows the result of the evaluation of the hair growth promoting activity of the modified and unmodified oligopeptides as disclosed in Example 13. The oligopeptide in one letter code is SIEQSXDQDE (SEQ ID NO: 156), wherein X is an unmodified or modified Cys or Lys as indicated.

The results obtained are shown in FIG. 11.

The test oligopeptides in each lane of FIG. 11 are as follows.

First from left: Unmodified oligopeptide (A)

Second from left: BMH modified oligopeptide (A)

Third from left: Unmodified oligopeptide (B)

Fourth from left: DSG modified oligopeptide (B)

As is understood from the results of FIG. 11, the bands in the second and fourth lane from the left (modified oligopeptides) were stronger than the bands in the first and third lane from the left (unmodified oligopeptides) respectively. These results demonstrate that the modified oligopeptides have a hair growth promoting activity, especially a higher hair growth promoting activity than that of the corresponding unmodified oligopeptide.

Moreover, by using the oligopeptides having an altered amino acid sequence and various cross-linking agents, the hair growth promoting activity was evaluated in the same manner as in the above.

As a result, it was demonstrated that all of the modified oligopeptides which were obtained by modifying Ser-Ile-Glu-Gln-Ser-Cys-Asp-Gln-Asp-Glu (SEQ ID NO:84); Ser-Ile-Cys-Glu-Gln-Ser-Asp-Gln-Asp-Glu (SEQ ID NO:133); or Ser-Ile-Glu-Gln-Ser-Cys-Asp-Gln (SEQ ID NO:86) with bismaleimide hexane (BMH), 1,4-bismaleimide butane (BMB) or bismaleimide ethane (BMOE), showed a hair growth promoting activity.

Example 14

Preparation of Oligopeptides

An oligopeptide represented by the following amino acid sequence Ser-Ile-Glu-Gln-Ser-Cys-Asp-Gln-Asp-Glu (SEQ ID NO:84) (comprising murine pep7 region) was synthesized by solid phase method using Fmoc. Also, a modified oligopeptide (referred to herein as "b7") having a modification by biotin at the N-terminus of the above sequence was prepared.

The synthesized oligopeptides were purified by a high performance liquid chromatography (HPLC), and it was confirmed by HPLC and Mass that the purity was 90% or more.

The conditions of HPLC are disclosed below.

Column: ODS-UG3 (Monomeric ODS, Nomura Kagaku), 1.0 mm in inside diameter, 100 mm in length Measurement: room temperature (25° C.)

Detection: UV 214 nm, 280 nm

Eluenting solvent: gradient of solvent A and solvent B (solvent A: 0.1% trifluoroacetic acid; solvent B: 90% acetonitrile/0.1% trifluoroacetic acid, linear concentration gradient from 5 minutes after (solvent B: 0%) to 55 minutes (solvent B: 55%)

Flow rate: 75 ml/ml

Retention time of oligopeptides:

Ser-Ile-Glu-Gln-Ser-Cys-Asp-Gln-Asp-Glu (SEQ ID NO:84): 21.52 minutes (dimer), 20.59 minutes (monomer)

b7; 29.89 minutes (monomer), 32.85 minutes (dimer)

The above-prepared oligopeptides were dissolved in phosphate buffered saline (PBS) in 0.3 mg/ml, and the same amount of 100% ethanol was added to this solution to prepare 50% ethanol/PBS solution (0.15 mg/ml). The cross-linking of the oligopeptide was carried out as follows. BMH dissolved in dimethylsulfoxide (651) was slowly added with stirring in a final concentration 33 μg/μl to the 1 mg/ml oligopeptide solution (5 ml) in PBS, and the mixture was reacted overnight at 4° C. To this solution, 6.6 ml of PBS and a solution of cysteine hydrochloride dissolved in PBS at 5 ml so as to give a final concentration of 5 mg/ml were added and mixed to prepare a S-S bridged oligopeptide (referred to as "ss7") solution (containing monomer to which a cross-linking agent was bound, as well as dimer) at a final concentration of 0.3 mg/ml. The retention time is 33.01 minutes by HPLC as performed under the conditions disclosed above. A control solution was prepared by reacting in the same manner with the addition of the reagents except for using PBS instead of the oligopeptide solution. A solution of the cross-linked oligopeptide was also added with the same volume of ethanol to prepare a 50% ethanol/PBS solution at the final concentration of 0.15 mg/ml. This S-S bridged oligopeptide was used for the evaluation of hair growth promoting activity in Examples 15 and Example 16.

Example 15

Evaluation of Hair Growth Promoting Activity by In Vivo Method

C3H and C57BL/6 mice are known to have sustained telogen for about 50 days from the 45th day after the birth to around the 95th day. Their hair cycle is easily judged based on the skin color changes, i.e., from pink in telogen to gray or black in anagen. A test for evaluating whether or not the administration the oligopeptides of the present invention promotes the transition from telogen to anagen was carried out using the mice. Seven weeks old (48 to 50-day old, female) C57BL/6 mice were purchased and hair of the back (about 3×2.5 $cm^2$) was carefully shaved with electric clippers for animals so as not to injure the skin, and the hair cycle was confirmed to be in telogen from the skin color. The oligopeptide solution prepared above was applied to five mice in each group, once a day and 5 days in a week in the amount of 0.2 ml until 38th day from the start of the test. The application was carried out by using a syringe without needle. Dipeptide (Ile-Lys) and tripeptide (Glu-Ile-Lys) of which N-terminal is biotinylated were mixed, and then added with the cross-linking agent to prepare a control solution.

Figure 6A:
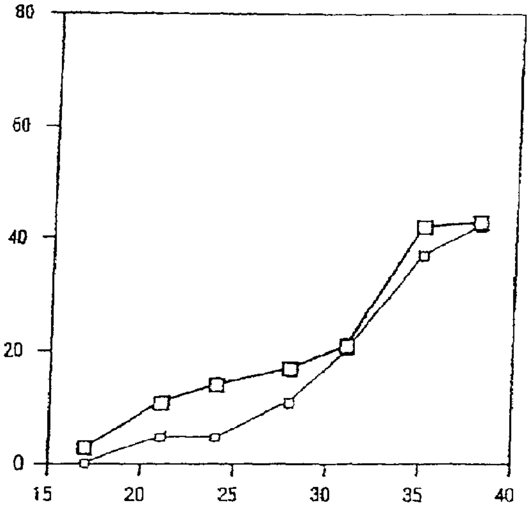
FIGS. 6A–6B show a hair growth promoting activity of an oligopeptide of the present invention (represented by the amino acid sequence Ser-Ile-Glu-Gln-Ser-Cys-Asp-Gln-Asp-Glu (SEQ ID NO: 84)).
Figure 6B:
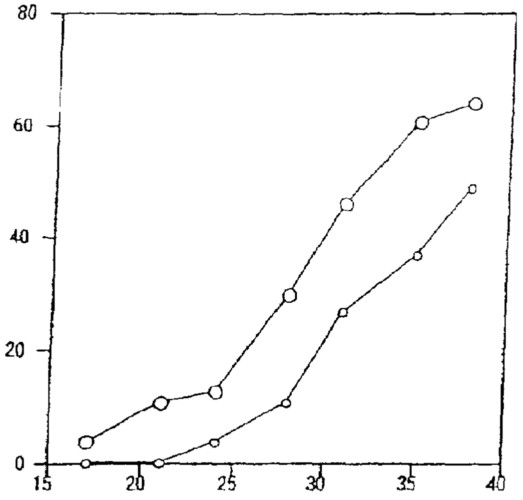
Figure 7:
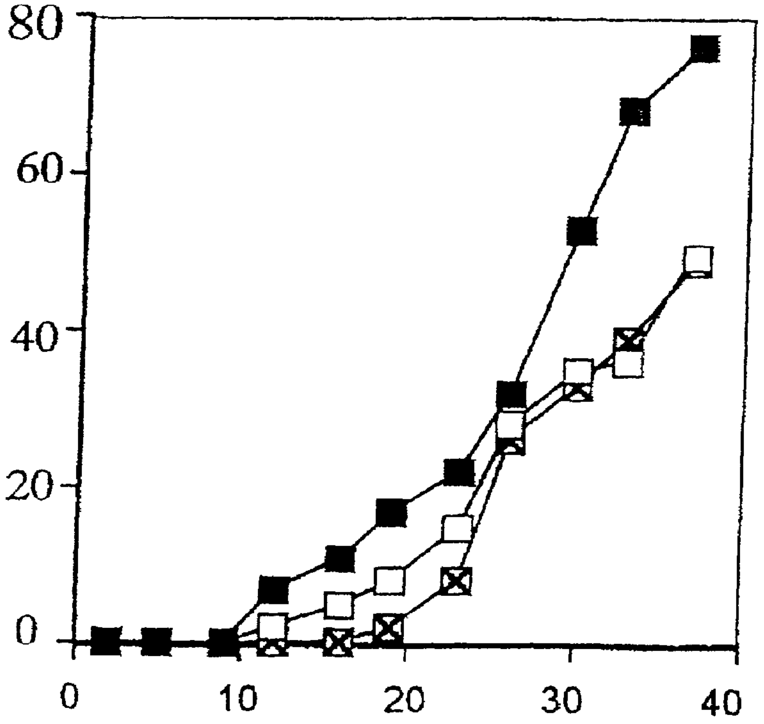
FIG. 7 shows a hair growth promoting activity of the oligopeptide of the present invention (S-S bridged and biotinylated oligopeptide: ss7). In the figure, ■ indicates the S-S bridged and biotinylated oligopeptide, □ indicates the result obtained from the first control (same as the control in FIG. 6) and ⊠shows the result of the second control (random 7-mer oligopeptide). The vertical axis indicates hair growth score, and the horizontal axis indicates the day from the start of application.

Plural persons (two persons) observed the mice twice a week by naked eye for evaluation, and gave a 6-graded score depending on a ratio of hair restoration area based on the hair shaved area. At the same time, photographs were taken. Hair growth scores were calculated as follows. At first, the following score was given depending on a ratio of areas where the skin color changes to gray or black in the hair shaved area; 0–20%: 1, 20–40%: 2, 40–60%: 3, 60–80%:4, 80–100%: 5. The sum of the above scores in each group was determined as the hair growth score. The maximum value of the hair growth score of each group was 50 for each of the persons for judgment, and the maximum value of hair growth score was 100 because the judgment was made by two persons. In the group wherein the S-S bridged oligopeptide (containing monomer to which a cross-linking agent was bound, as well as dimer) and biotynalated oligopeptide was applied, the transition to anagen was 7 days or more earlier than the control group, and the hair restoration was promoted at any time until the hair grew and restored almost completely. In the group wherein the biotinylated oligopeptide was applied, the hair restoration was promoted until about 30 days from the start of the test as compared with the control group similarly to the S-S bridged group. The results are shown in FIGS. 6 and 7. As shown by these results, the oligopeptide represented by the amino acid sequence Ser-Ile-Glu-Gln-Ser-Cys-Asp-Gln-Asp-Glu (SEQ ID NO: 84) has hair growth promoting activity.

Example 16

Evaluation of Hair Growth Promoting Activity Using the Monoclonal Antibody of the Present Invention The skin tissues of maxilla of ICR mice (pregnancy 12 days) were collected by stereoscopic microscope, and left and right sides were respectively recovered from 5 mice. 5 pieces of each of the thus collected left (for control) and right (for test oligopeptides) skins from 5 mice were respectively placed on 1 nuclepore membrane (pore diameter 8 μm; diameter 13 mm), and were set in such a way that the outside upturns by observing the samples with stereoscopic microscope. 5001 of Dalbecco's MEM/Ham F12 medium containing 1% BSA was added to 2 wells of 24 well dish. The test oligopeptide in a solvent (PBS) was added in a final concentration of 20 μM to one well, and solvent (PBS) was added in the same amount to the other well as a control. The S-S bridged oligopeptide prepared in the above Example was used as the test oligopeptide.

Each membrane having skin tissues thereon was launched on the solution in the above wells, and was incubated at 37° C. for 6 days. 5 pieces of tissue were recovered from the membrane into 100 μl of SDS sample buffer (SDS 0.02 g/ml, glycerol 0.2 g/ml, pH6.8), and dissolved by ultrasonic treatment. The control membrane was also treated similarly. The solution obtained by such a treatment was subjected to electrophoresis (35 mA, 1.5 hour) in SDS-PAGE (acrylamide 4–20%), and transferred to PVDF membrane, and incubated in Tris buffer containing 5% skim milk (TBST) for 1 hour. The membrane was reacted with mAb 27 (10 μg/ml in TBST) obtained in Example 6 for 1 hour, and was washed well with TBS. Then, peroxidase labeled anti-rat IgG (Amersham) (1/1000 diluted in TBST) was reacted as the second antibody, and the membrane was washed well with TBS. The intensity of the reaction of mAb 27 was examined using ECL kit (Amersham).

Figure 13:
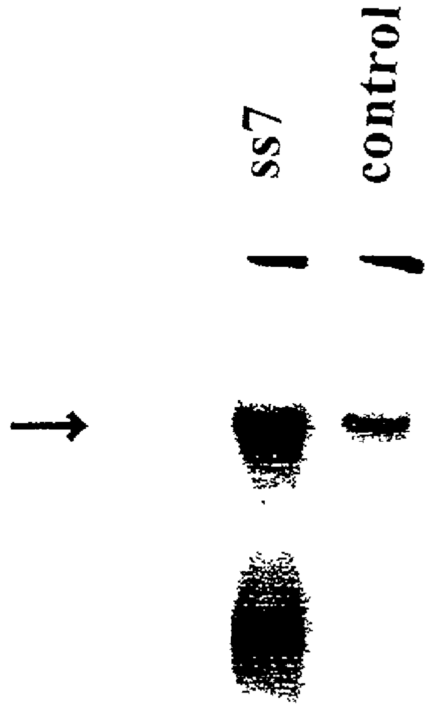
FIG. 13 shows the result of the evaluation of a hair growth promoting activity of oligopeptide using a monoclonal antibody mAb27.

The obtained results are shown in FIG. 13.

In FIG. 13, left lane shows the result of the sample where the S-S bridged oligopeptide (ss7) prepared in Example 14 was added, and right lane (control) shows the sample where only solvent was added. As is understood from the results of FIG. 13, a stronger band was detected in the sample where the S-S bridged oligopeptide (ss7) was added, than in the control. This suggests that the expressed amount of an antigen recognized by mAb27 is increased.

This Example demonstrates that ss7 has hair growth promoting activity. From this example, it is understood that ss7 increases the expressed amount of the antigen of mAb27. From the examples, it is understood that the antigen of mAb27 is specific for anagen of follicle. Therefore, the increase of antigen of mAb27 is considered to be an index which represents a hair growth promoting activity. That is, a hair growth promoting activity can be evaluated by examining the expression of the antigen of about 220 kDa present in new follicle using mAb27.

The monoclonal antibody of the present invention can specifically recognize an antigen present in epithelial new follicle, and is useful for the evaluation of hair growth promoting activity.

Example 17

Oligopeptide b7ΔC1, b7ΔC2, b7ΔC3, b7ΔC4, and b7ΔC5 were synthesized by deleting one, two, three, four, or five amino acids from the C-terminal of b7, respectively, and then blocking sulfhydryl group. Oligopeptide b7ΔN1, b7ΔN2, and b7ΔN3 were synthesized by deleting one, two, or three amino acids from the N-terminal of b7. b7ΔC1 refers to the oligopeptide sequence (SIEQSCDQD) (SEQ ID NO:85); b7ΔC2 refers to the oligopeptide sequence (SIEQSCDQ) (SEQ ID NO:86); b7ΔC3 refers to the oligopeptide sequence (SIEQSCD) (SEQ ID NO: 87); b7ΔC4 refers to the oligopeptide sequence (SIEQSC) (SEQ ID NO: 88); b7ΔC5 refers to the oligopeptide sequence (SIEQS) (SEQ ID NO:135); b7ΔN1 refers to the oligopeptide sequence (IEQSCDQDE) (SEQ ID NO: 89); b7ΔN2 refers to the oligopeptide sequence (EQSCDQDE) (SEQ ID NO: 90); and b7ΔN3 refers to the oligopeptide sequence (QSCDQDE) (SEQ ID NO:91). Oligopeptide bk7 (without block of sulfhydryl group) represented by the amino acid sequence Lys-Ser-Ile-Glu-Gln-Ser-Cys-Asp-Gln-Asp-Glu (SEQ ID NO: 83) was synthesized whose N-terminal was bound with lysine.

Human keratinocytes (NHEK cell, Clonetics, available from Sanko Jyun-yaku, Ltd.) were cultivated in a medium for proliferation (Clontics) comprising 30 μg/ml BPE, 0.1 ng/ml human EGF, 5 μg/ml insulin, 0.5 μg/ml hydrocortisone, 50 μg/ml gentamycin, and 50 ng/ml amphoterin. These cells were re-suspended at the concentration of $1\times10^4$ cells/ml in a medium wherein EGF, insulin, and hydrocortisone were removed from the above medium for proliferation, and then 100 μl of the suspension was placed on each well of a 96-well plate. At the same time of the plating of the cells, 5 μl of 1 mg/ml oligopeptide was added to the suspension so as to be final concentration of 50 μg/ml. After cultivation for 16–20 hours, the amount of IL-8 in the culture supernatants was measured by ELISA kit (ENDOGEN). Table IV shows the correlation between inducing activity on IL-8 secretion by NHEK cells and hair growth promoting activity.

TABLE IV

| Oligopeptide | IL-8 inducing activity | Hair growth Activity |
|---|---|---|
| b7 | ◎ | ○ |
| cross-linked b7 | ◎ | ◎ |
| ss7 | ◎ | ◎ |
| control | X | X |

b7 refers to b7 is SIEQSCDQDE (SEQ ID NO: 4). ssb7 refers to cross-linked b7. ss7 refers to S-S bridged and biotinylated oligopeptide.

Figure 8:
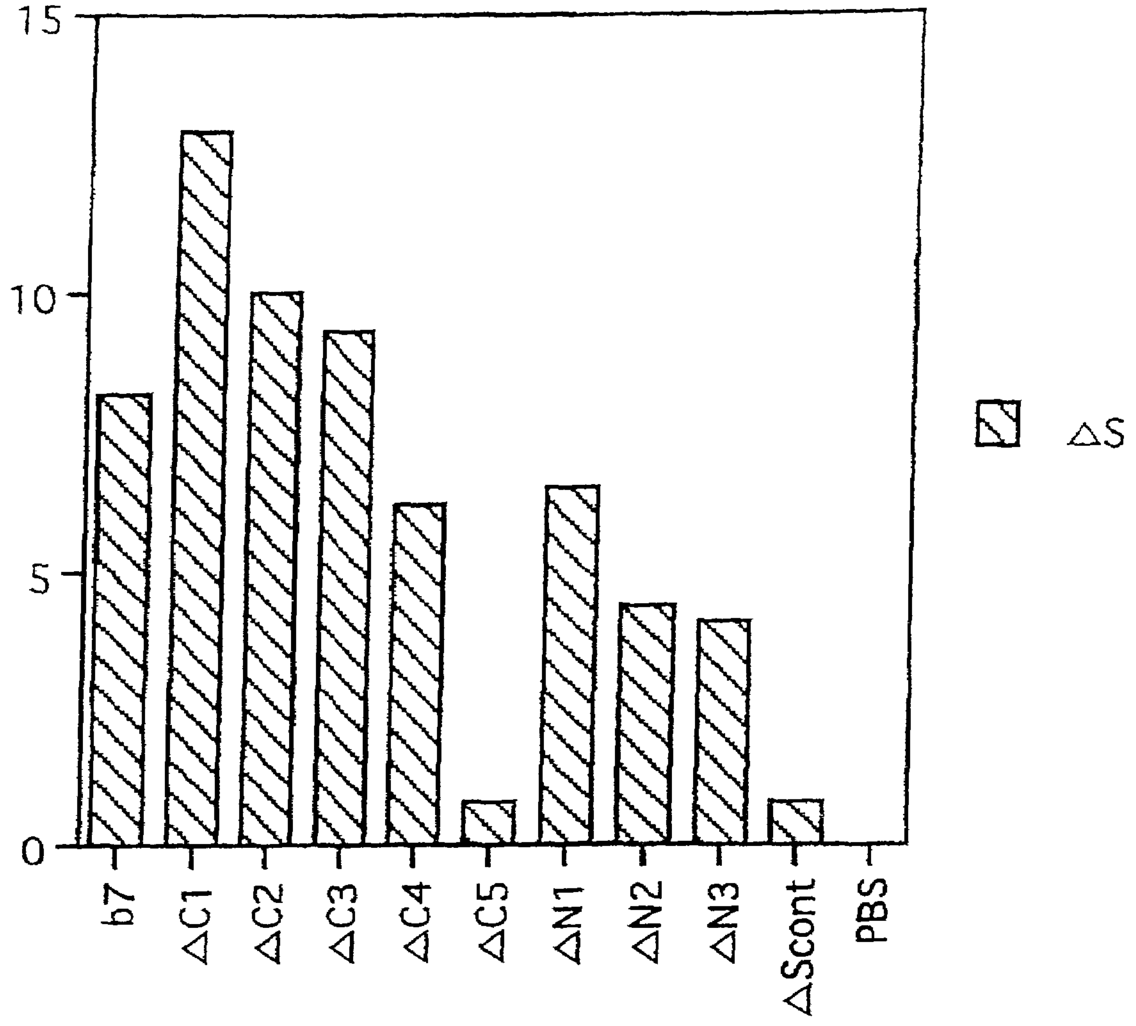
FIG. 8 shows the result of evaluation of b7ΔC1, b7ΔC2, b7ΔC3, b7ΔC4, b7ΔC5, b7ΔN1, b7ΔN2, and b7ΔN3 on IL-8 inducing activity. b7ΔC1 refers to the oligopeptide sequence (SIEQSCDQD) (SEQ ID NO: 85); b7ΔC2 refers to the oligopeptide sequence (SIEQSCDQ) (SEQ ID NO: 86); b7ΔC3 refers to the oligopeptide sequence (SIEQSCD) (SEQ ID NO: 87); b7ΔC4 refers to the oligopeptide sequence (SIEQSC) (SEQ ID NO: 88); b7ΔC5 refers to the oligopeptide sequence (SIEQS) (SEQ ID NO: 135); b7ΔN1 refers to the oligopeptide sequence (IEQSCDQDE) (SEQ ID NO: 89); b7ΔN2 refers to the oligopeptide sequence (EQSCDQDE) (SEQ ID NO: 90); and b7ΔN3 refers to the oligopeptide sequence (QSCDQDE) (SEQ ID NO: 91). In the figure, Scont indicates the result of blocking reagent, PBS indicates the result of phosphate buffered saline, and the vertical axis indicates the relative value of the secretion amount of IL-8.
Figure 9:
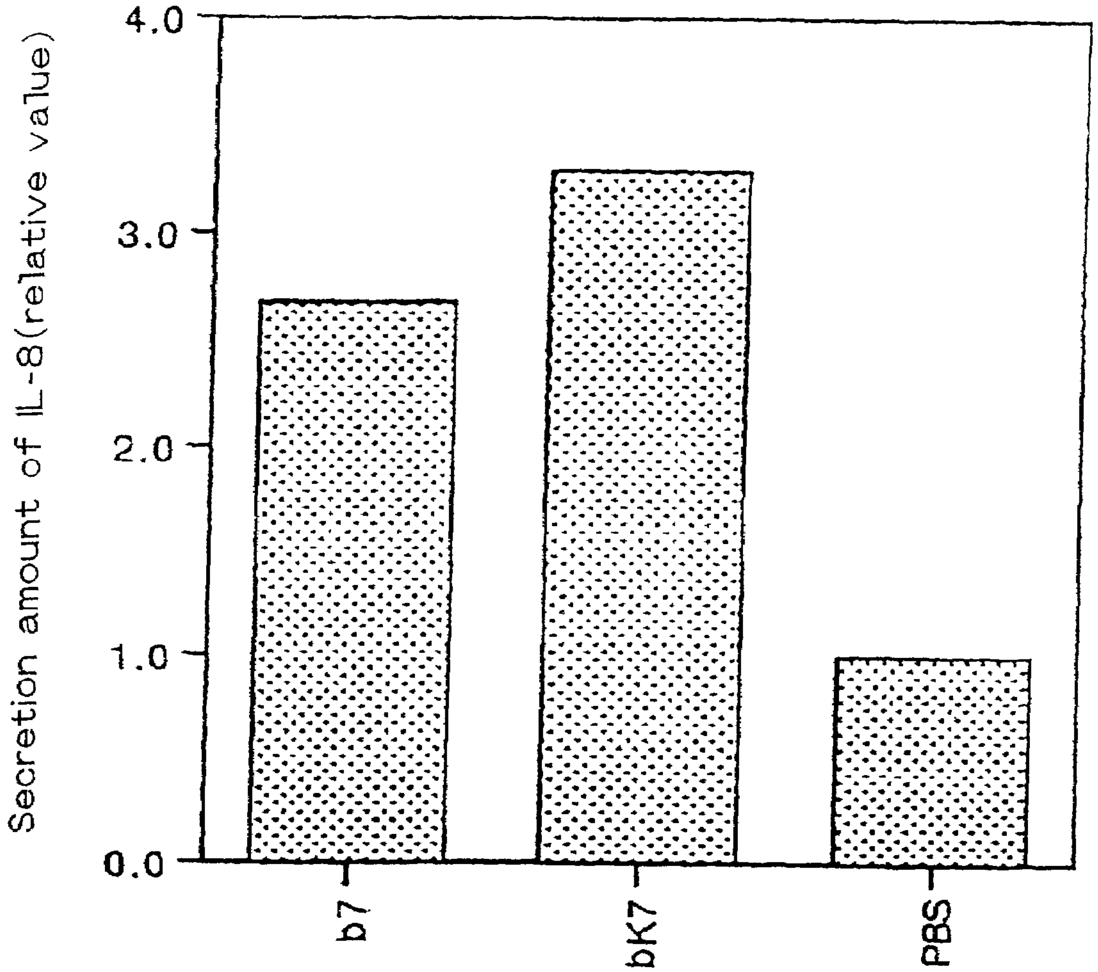
FIG. 9 shows the results of evaluation of oligopeptide bk7 obtained by binding biotin to the N-terminal of the oligopeptide represented by the amino acid sequence Lys-Ser-Ile-Glu-Gln-Ser-Cys-Asp-Gln-Asp-Glu (SEQ ID NO: 83) and oligopeptide b7 (SIEQSCDQDE) (SEQ ID NO: 84) on IL-8 inducing activity, as described in Examples 17 and 18. In the figure, PBS indicates the result of phosphate buffered saline, and the vertical axis indicates the relative value of the secretion amount of IL-8.

The results obtained by evaluation of oligopeptides b7ΔC1, b7ΔC2, b7ΔC3, b7ΔC4, b7ΔC5, b7ΔN1, b7ΔN2, and b7ΔN3 on IL-8 inducing activity are shown in FIG. 8. When one or more amino acids were deleted from the N-terminal, the secretion amount of IL-8 was slightly decreased, and when one or more amino acids were deleted from the C-terminal, the secretion amount of IL-8 was maintained until deletion of four amino acids. When five amino acids were deleted, the secretion amount of IL-8 was significantly decreased. From these results, it is revealed that almost the same hair growth activity as that of oligopeptide b7 can be expected by the deletion of up to four amino acids from the C-terminal, or the deletion of up to three amino acids from the N-terminal of the b7 region. As shown in FIG. 9, 11-mer oligopeptide bk7 had also almost the same IL-8 inducing activity as that of oligopeptide b7.

Example 18

The N-terminus of oligopeptide murine pep7 was biotinylated using NHS-biotin or NHC-biotin (Pierce) in accordance with the instructions of the attached manual. When NHS-biotin was used, —O—CO—$(CH_2)_4$—(13.5 Å) was introduced as a spacer between the N-terminus and the biotin, and when NHS-LC-biotin was used, —O—CO—$(CH_2)_5$—NH—CO—$(CH_2)_4$—(22.4 Å) was introduced as a spacer between the N-terminal and the biotin. The secretion amount of IL-8 was determined using these biotinylated oligopeptides in the same manner as in Example 17. These oligopeptides had almost the same IL-8 inducing activity as that of oligopeptide b7. These results show that the oligopeptide of which N-terminal is directly biotinylated has almost the same hair growth promoting activity as that of the oligopeptide of which N-terminal is biotinylated by means of a spacer, and both of them are active as compared to the b7 region without biotin at the N-terminus.

The invention claimed is:

1. An isolated oligopeptide of between 6 and 40 amino acid residues in length having hair growth promoting activity, comprising an amino acid sequence selected from the group consisting of the following:

(SEQ ID NO:83)
Lys-Ser-Ile-Glu-Gln-Ser-Cys-Asp-Gln-Asp-Glu;

(SEQ ID NO:84)
Ser-Ile-Glu-Gln-Ser-Cys-Asp-Gln-Asp-Glu;

-continued (SEQ ID NO:85)
Ser-Ile-Glu-Gln-Ser-Cys-Asp-Gln-Asp;

(SEQ ID NO:86)
Ser-Ile-Glu-Gln-Ser-Cys-Asp-Gln;

(SEQ ID NO:87)
Ser-Ile-Glu-Gln-Ser-Cys-Asp;

(SEQ ID NO:88)
Ser-Ile-Glu-Gln-Ser-Cys;

-continued (SEQ ID NO:89)
Ile-Glu-Gln-Ser-Cys-Asp-Gln-Asp-Glu;

(SEQ ID NO:90)
Glu-Gln-Ser-Cys-Asp-Gln-Asp-Glu; and (SEQ ID NO:91)
Gln-Ser-Cys-Asp-Gln-Asp-Glu.

2. An isolated oligopeptide of between 8 and 104 amino acid residues in length having hair growth promoting activity comprising an amino acid sequence selected from the group consisting of:

(SEQ ID NO:116)
Ser-Ile-Glu-Gln-Xaa-Ser-Asp-Gln;

(SEQ ID NO:117)
Ser-Ile-Glu-Xaa-Gln-Ser-Asp-Gln; and (SEQ ID NO:118)
Ser-Ile-Xaa-Glu-Gln-Ser-Asp-Gln, wherein Xaa is Cys or a reactive substance-bound Cys.

3. The oligopeptide of claim 2 comprising an amino acid sequence selected from the group consisting of:

(SEQ ID NO:92)
Ser-Ile-Glu-Gln-Cys-Ser-Asp-Gln;

(SEQ ID NO:93)
Ser-Ile-Glu-Cys-Gln-Ser-Asp-Gln; and (SEQ ID NO:94)
Ser-Ile-Cys-Glu-Gln-Ser-Asp-Gln.

4. The oligopeptide of claim 1 comprising the following amino acid sequence:

Ser Ile Glu Gln Ser Cys Gly Gln His Glu (SEQ ID NO: 81).

5. The oligopeptide of claim 1, 2, or 3, wherein the amino acid sequence comprises natural amino acid residues, non-natural amino acid residues, or a mixture of both.

6. A composition comprising the oligopeptide of claim 1.

7. A composition comprising the oligopeptide of claim 2.

8. A composition comprising the oligopeptide of claim 3.

9. A composition comprising the oligopeptide of claim 4.

10. The composition of claim 6, 7, 8, or 9 further comprising a pharmaceutically acceptable excipient.

11. A method of promoting hair growth in a mammal comprising administering a composition of claim 6 in an amount effective to promote hair growth in said mammal.

12. A method of promoting hair growth in a mammal comprising administering a composition of claim 7 in an amount effective to promote hair growth in said mammal.

13. A method of promoting hair growth in a mammal comprising administering a composition of claim 8 in an amount effective to promote hair growth in said mammal.

14. A method of promoting hair growth in a mammal comprising administering a composition of claim 9 in an amount effective to promote hair growth in said mammal.

15. The oligopeptide of claim 1, wherein said oligopeptide comprises Lys-Ser-Ile-Glu-Gln-Ser-Cys-Asp-Gln-Asp-Glu (SEQ ID NO: 83).

16. The oligopeptide of claim 1, wherein said oligopeptide comprises

Ser-Ile-Glu-Gln-Ser-Cys-Asp-Gln-Asp-Glu (SEQ ID NO: 84).

17. The oligopeptide of claim 1, wherein said oligopeptide comprises

Ser-Ile-Glu-Gln-Ser-Cys-Asp-Gln-Asp (SEQ ID NO: 85).

18. The oligopeptide of claim 1, wherein said oligopeptide comprises

Ser-Ile-Glu-Gln-Ser-Cys-Asp-Gln (SEQ ID NO: 86).

19. The oligopeptide of claim 1, wherein said oligopeptide comprises

Ser-Ile-Glu-Gln-Ser-Cys-Asp (SEQ ID NO: 87).

20. The oligopeptide of claim 1, wherein said oligopeptide comprises Ser-Ile-Glu-Gln-Ser-Cys (SEQ ID NO: 88).

21. The oligopeptide of claim 1, wherein said oligopeptide comprises

Ile-Glu-Gln-Ser-Cys-Asp-Gln-Asp-Glu (SEQ ID NO: 89).

22. The oligopeptide of claim 1, wherein said oligopeptide comprises

Glu-Gln-Ser-Cys-Asp-Gln-Asp-Glu (SEQ ID NO: 90).

23. The oligopeptide of claim 1, wherein said oligopeptide comprises

Gln-Ser-Cys-Asp-Gln-Asp-Glu (SEQ ID NO: 91).

24. The oligopeptide of claim 2, wherein said oligopeptide comprises

Ser-Ile-Glu-Gln-Xaa-Ser-Asp-Gln (SEQ ID NO: 116), wherein Xaa is Cys or a reactive substance-bound Cys.

25. The oligopeptide of claim 2, wherein said oligopeptide comprises

Ser-Ile-Glu-Xaa-Gln-Ser-Asp-Gln (SEQ ID NO: 117), wherein Xaa is Cys or a reactive substance-bound Cys.

26. The oligopeptide of claim 2, wherein said oligopeptide comprises

Ser-Ile-Xaa-Glu-Gln-Ser-Asp-Gln (SEQ ID NO: 118), wherein Xaa is Cys or a reactive substance-bound Cys.

27. A composition comprising the oligopeptide of claim 15, 16, 17, 18, 19, 20, 21, 22, or 23.

28. The composition of claim 27 further comprising a pharmaceutically acceptable excipient.

29. A composition comprising the oligopeptide of claim 24, 25, or 26.

30. The composition of claim 29 further comprising a pharmaceutically acceptable excipient.

31. The isolated oligopeptide of claim 24, 25, or 26 wherein said oligopeptide is between 8 and 100 amino acid residues in length.

32. The isolated oligopeptide of claim 24, 25, or 26 wherein said oligopeptide is between 8 and 75 amino acid residues in length.

33. The isolated oligopeptide of claim 24, 25, or 26 wherein said oligopeptide is between 8 and 50 amino acid residues in length.

34. The isolated oligopeptide of claim 24, 25, or 26 wherein said oligopeptide is between 8 and 25 amino acid residues in length.

35. A method of promoting hair growth in a mammal comprising administering a composition of claim 27 in an amount effective to promote hair growth in said mammal.

36. A method of promoting hair growth in a mammal comprising administering a composition of claim 29 in an amount effective to promote hair growth in said mammal.

37. The isolated oligopeptide of claim 20 wherein said oligopeptide is between 6 and 40 amino acid residues in length.

38. The isolated oligopeptide of claim 20 wherein said oligopeptide is between 6 and 30 amino acid residues in length.

39. The isolated oligopeptide of claim 20 wherein said oligopeptide is between 6 and 25 amino acid residues in length.

40. The isolated oligopeptide of claim 20 wherein said oligopeptide is between 7 and 20 amino acid residues in length.

41. The isolated oligopeptide of claim 20 wherein said oligopeptide is between 7 and 15 amino acid residues in length.

42. The isolated oligopeptide of claim 20 wherein said oligopeptide is between 6 and 11 amino acid residues in length.

* * * * *